US011702656B2

(12) United States Patent
Fu et al.

(10) Patent No.: US 11,702,656 B2
(45) Date of Patent: Jul. 18, 2023

(54) REPROGRAMMING OF NON-NEURONAL CELLS INTO NEURONS AND METHODS AND COMPOSITIONS TO TREAT NEURODEGENERATIVE DISEASES AND DISORDERS

(71) Applicant: The Regents of the University of California, Oakland, CA (US)

(72) Inventors: Xiang-Dong Fu, Rancho Santa Fe, CA (US); Hao Qian, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/986,798

(22) Filed: Aug. 6, 2020

(65) Prior Publication Data

US 2020/0377891 A1    Dec. 3, 2020

Related U.S. Application Data

(63) Continuation of application No. PCT/US2019/027027, filed on Apr. 11, 2019.

(60) Provisional application No. 62/718,774, filed on Aug. 14, 2018, provisional application No. 62/656,322, filed on Apr. 11, 2018.

(51) Int. Cl.
| | |
|---|---|
| C12N 15/113 | (2010.01) |
| A61P 25/28 | (2006.01) |
| C12N 5/0793 | (2010.01) |
| C12N 15/86 | (2006.01) |
| A61P 25/16 | (2006.01) |

(52) U.S. Cl.
CPC ............ *C12N 15/113* (2013.01); *A61P 25/16* (2018.01); *C12N 5/0619* (2013.01); *C12N 2310/11* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| | | |
|---|---|---|
| 2013/0203835 A1 | 8/2013 | Manley et al. |
| 2015/0250900 A1 | 9/2015 | Chen et al. |
| 2015/0299698 A1 | 10/2015 | Fu et al. |
| 2017/0002317 A1 | 1/2017 | Kamath et al. |
| 2017/0354707 A1 | 12/2017 | Chen et al. |

FOREIGN PATENT DOCUMENTS

| | | | |
|---|---|---|---|
| WO | 2011/091048 A1 | | 7/2011 |
| WO | 2012/118988 A1 | | 9/2012 |
| WO | WO 2014/071157 A1 | * | 5/2014 |
| WO | 2017/079547 A2 | | 5/2017 |

OTHER PUBLICATIONS

Lazic and Barker, Cell-based therapies for disorders of the CNS, Expert Opin. Ther. Patents (2005) 15(10): 1361-1376.*
Kahle et al., The emerging utility of animal models of chronic neurodegenerative disease, Emerging Therapeutic Targets (2001) 5(1): 125-32.*
Richardson and Burns, Mouse Models of Alzheimer's Disease: A Quest for Plaques and Tangles, ILAT Journal, 2002, vol. 43 (2), p. 89-99.*
Molnar and Nemeth, Gene therapy in neurology: review of ongoing clinical trials, Clin. Invest. (2012) 2(6), 639-652.*
Manno et al, Successful transduction of liver in hemophilia by AAV-Factor IX and limitations imposed by the host immune response, Nature Medicine, 2006, pp. 342-349 and 592.*
Salmon et al, Safety profile of recombinant adeno-associated viral vectors: focus on alipogene tiparvovec (Glybera), Expert Rev. Clin. Pharmacol., 2014,7(1), 53-65.*
Hurdy, Therapeutic AAV Gene Transfer to the Nervous System: A Clinical Reality, Neuron 101, Mar. 6, 2019, 839-862.*
Fumoto et al, Targeted Gene Delivery: Importance of Administration Routes, Chapter 1, Intech, 2013, pp. 3-31.*
Foust et al, Intravascular AAV9 preferentially targets neonatal-neurons and adult-astrocytes in CNS, Nat Biotechnol. Jan. 2009 ; 27(1): 59-65.*
Liang et al, Inhibition of polypyrimidine tract-binding protein 3 induces apoptosis and cell cycle arrest, and enhances the cytotoxicity of 5-fluorouracil in gastric cancer cells, British Journal of Cancer (2017) 116, 903-911.*
Salti et al, Expression of Early Developmental Markers Predicts the Efficiency of Embryonic Stem Cell Differentiation into Midbrain Dopaminergic Neurons, Stem Cells and Development, 2013, pp. 397-411.*
Qian et al, Reversing a model of Parkinson's disease with in situ converted nigral neurons, Nature, 2020, pp. 550-556 plus supplemental pp. 1-21.*
Van Laar and Van Laar, Antisense Oligonucleotide Therapies, Practical Neurology, 2019, pp. 1-8.*
Grodin et al, Continuous intranigral infusion is not associated with observable behavioral deficits or marked pathology: a preclinical safety study, J Neurosurg 126:pp. 1-2, 2017 summary page.*
Caiazzo et al., "Direct generation of functional dopaminergic neurons from mouse and human fibroblasts," Nature, vol. 476, pp. 224-227, 2011.
Coutinho-Mansfield et al., "PTB/PTB switch: a post-transcriptional mechanism for programming neuronal differentiation," Genes & Development, vol. 21, pp. 1573-2577, 2007.
Damier et al., "The substantia nigra of the human brain: II Patterns of loss of dopamine-containing neurons in Parkinson's disease," Brain, vol. 122, pp. 1437-1448, 1999.
Heffernan et al., "Design and screening of a glial cell-specific, cell penetrating peptide for therapeutic applications in multiple sclerosis," PLoS One, vol. 7, e45501, pp. 1-12, 2012.

(Continued)

*Primary Examiner* — Maria Marvich
(74) *Attorney, Agent, or Firm* — Gavrilovich, Dodd & Linsey LLP

(57) ABSTRACT

Provided herein is a method of reprogramming a non-neuronal cell to a neuron. Aspects of the present disclosure relate to using cell reprogramming agent suppresses the expression or activity of PTB to convert a non-neuronal cell into a neuron. Also provided herein is a method of treating neurodegenerative disease by reprogramming non-neuronal cells in vivo to functional neurons.

15 Claims, 28 Drawing Sheets

Specification includes a Sequence Listing.

(56) References Cited

OTHER PUBLICATIONS

Leipzig et al., "Functional immobilization of interferon-gamma induces neuronal differentiation of neural stem cells," J. Biomed. Mater. Res., 93A:625-633, 2009.

Makeyev et al., "The MicroRNA miR-124 promotes neuronal differentiation by triggering brain-specific alternative pre-mRNA splicing," Mol Cell., 27(3):435-448, 2007.

Silber et al., "miR-124 and MiR-137 inhibit proliferation of glioblastoma multiforme cells and induce differentiation of brain tumor stem cells," BMC Medicine, 6:1-17, 2008.

Stefani et al., "Small non-coding RNAs in animal development," Nature Reviews, 9:219-230, 2008.

Surmeier et al., "Selective neuronal vulnerability in Parkinson disease," Nat Rev Neurosci., vol. 18, pp. 101-113, Jan. 20, 2017.

Watanabe et al., "Conversion of myoblasts to physiologically active neuronal phenotype," Genes & Development, 18:889-900, 2004.

Xue et al., "Direct conversion of fibroblasts to neurons by reprogramming PTB-regulated microRNA circuits," Cell, vol. 152, pp. 82-96, 2013.

Xue et al., "Sequential regulatory loops as key gatekeepers for neuronal reprogramming in human cells," Nat. Neurosci, vol. 19, pp. 807-815, Apr. 25, 2016.

Zheng et al., "PSD-95 is post-trascriptionally repressed during early neural development by PTBP1 and PTBP2," Nature Neuroscience, 15:381-389, Jan. 15, 2012.

Wittman-Regis, Agnes, International Preliminary Report on Patentability and Written Opinion, PCT/US2019/027027, The International Bureau of WIPO, Oct. 22, 2020.

Ding et al., "Mash1 efficiently reprograms rat astrocytes into neurons", Neural Regeneration Research, Jan. 2014, vol. 9, Issue 1, pp. 25-32.

Ghasemi-Kasman Maryam et al., "MicroRNA-Mediated In Vitro and In Vivo Direct Conversion of Astrocytes to Neuroblasts", Plos One, vol. 10, No. 6, Jun. 1, 2015, p. e0127878.

Niu, Wenze et al., "In vivo reprogramming of astrocytes to neuroblasts in the adult brain", Nature Cell Biology, vol. 15, No. 10, Sep. 22, 2013, pp. 1164-1175.

Stappert, Laura et al., "The role of microRNAs in human neural stem cells, neuronal differentiation and subtype specification", Cell and Tissue Research, vol. 359, No. 1, Aug. 30, 2014, pp. 47-64.

Torper et al., "Generation of induced neurons via direct conversion in vivo", Proceedings of the National Academy of Sciences, vol. 110, No. 17, Mar. 25, 2013, pp. 7038-7043.

\* cited by examiner

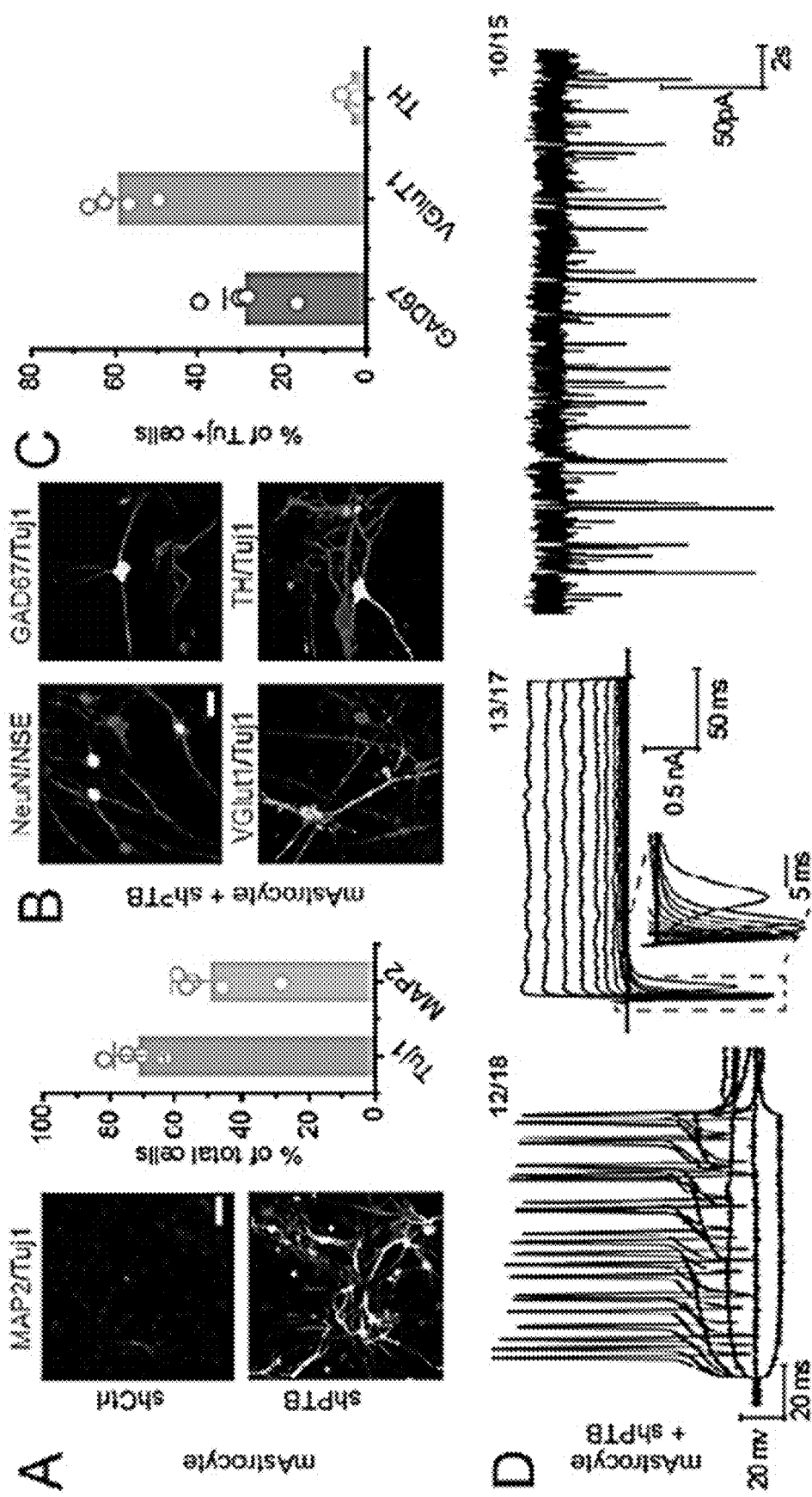
FIG. 5A-D

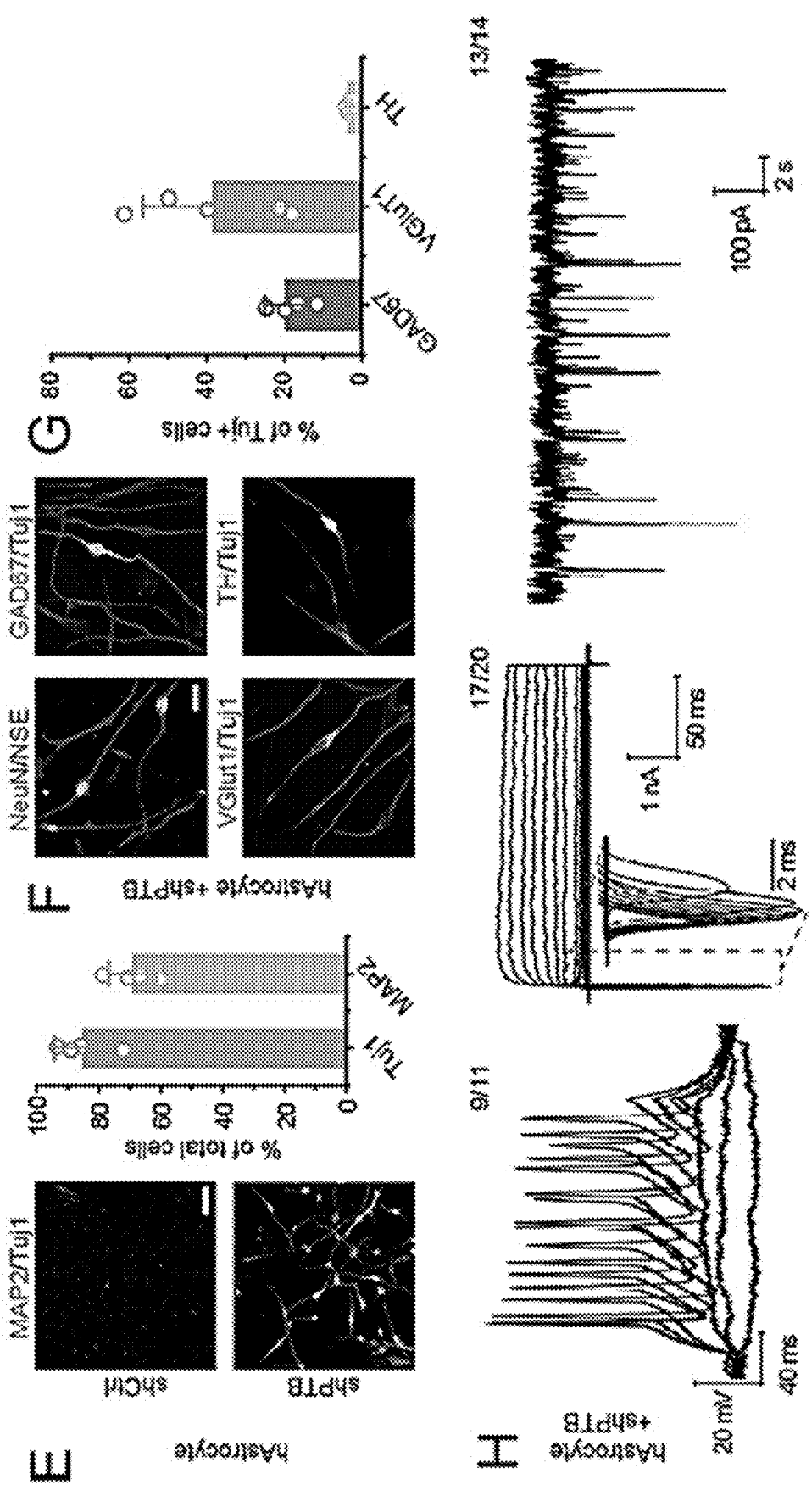
FIG. 5E-H

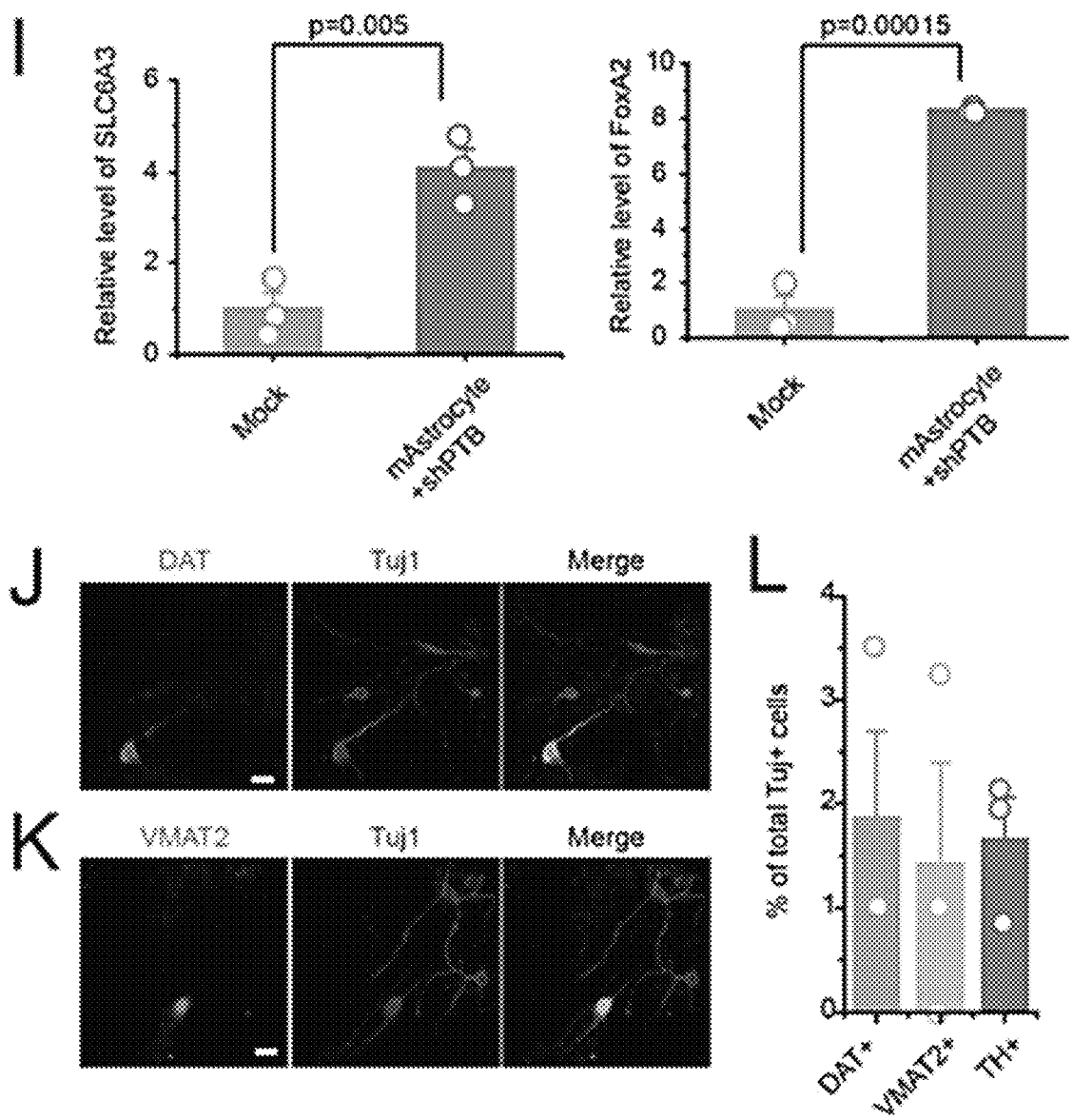
FIG. 5I-L

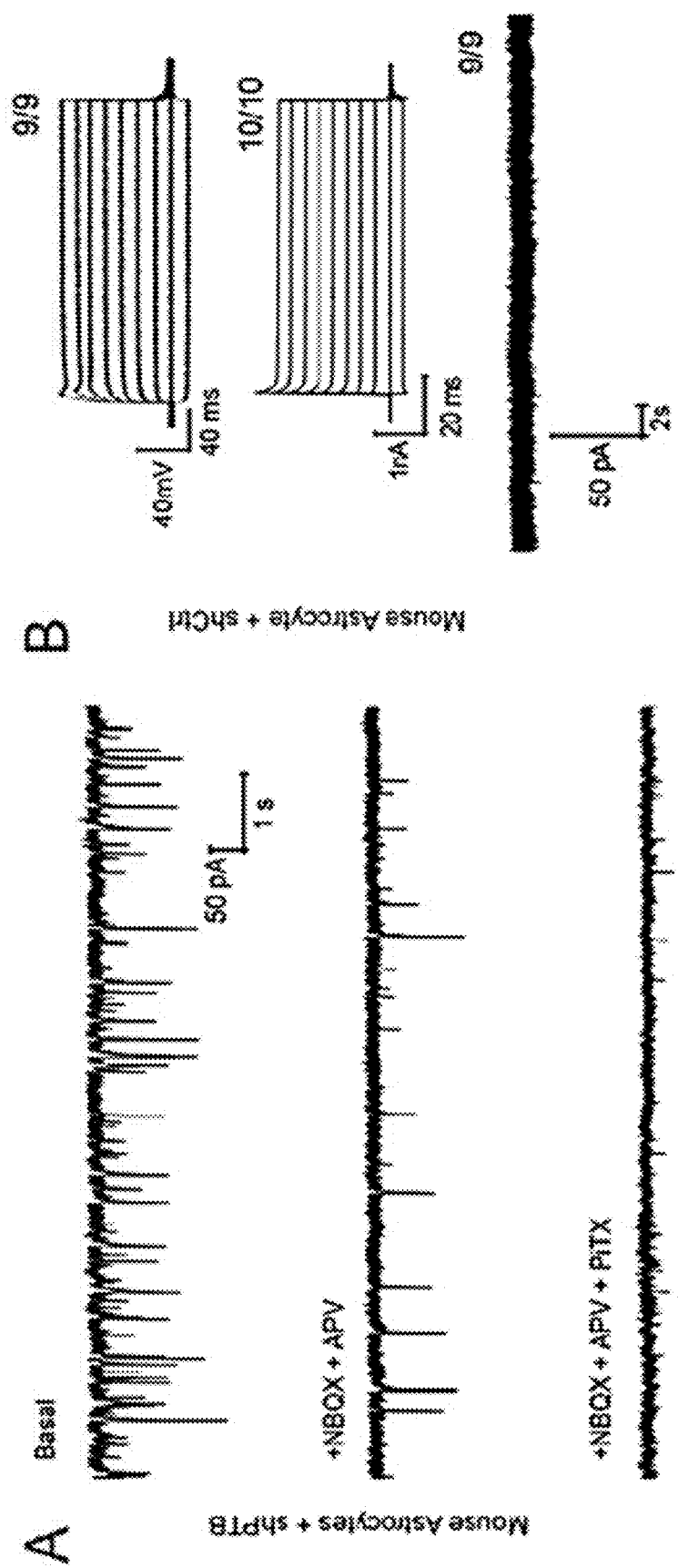
FIG. 6A-B

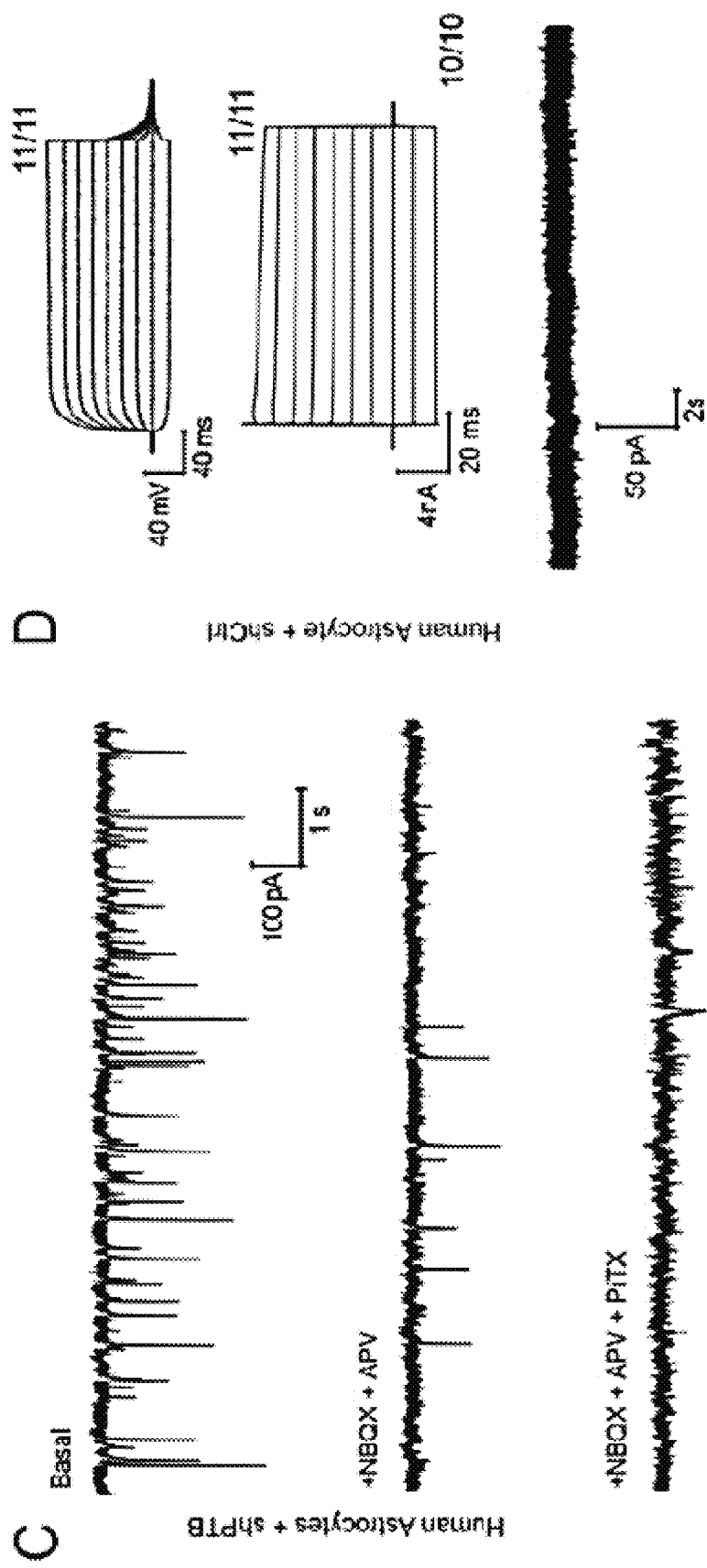
FIG. 6C-D

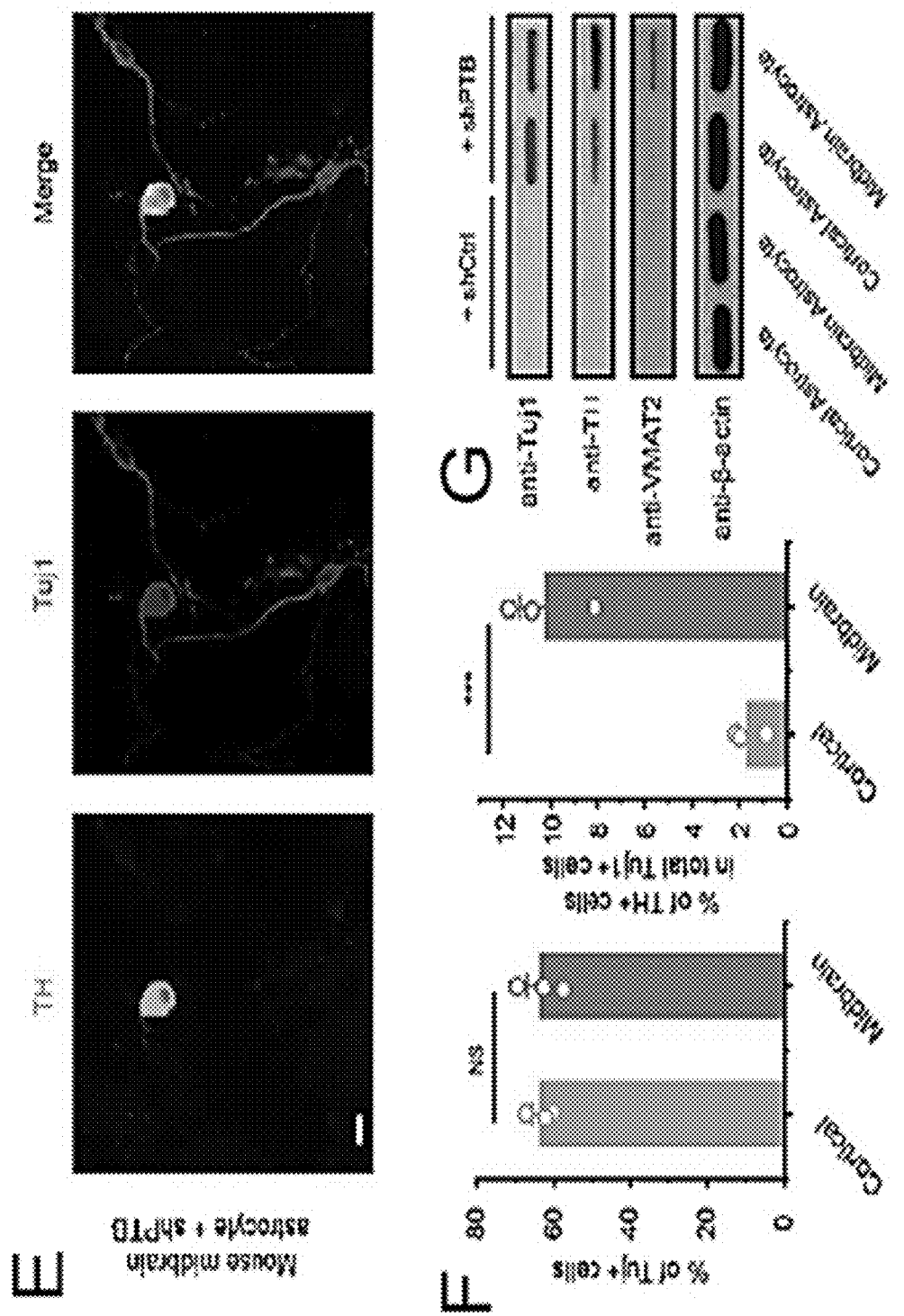
FIG. 6E-G

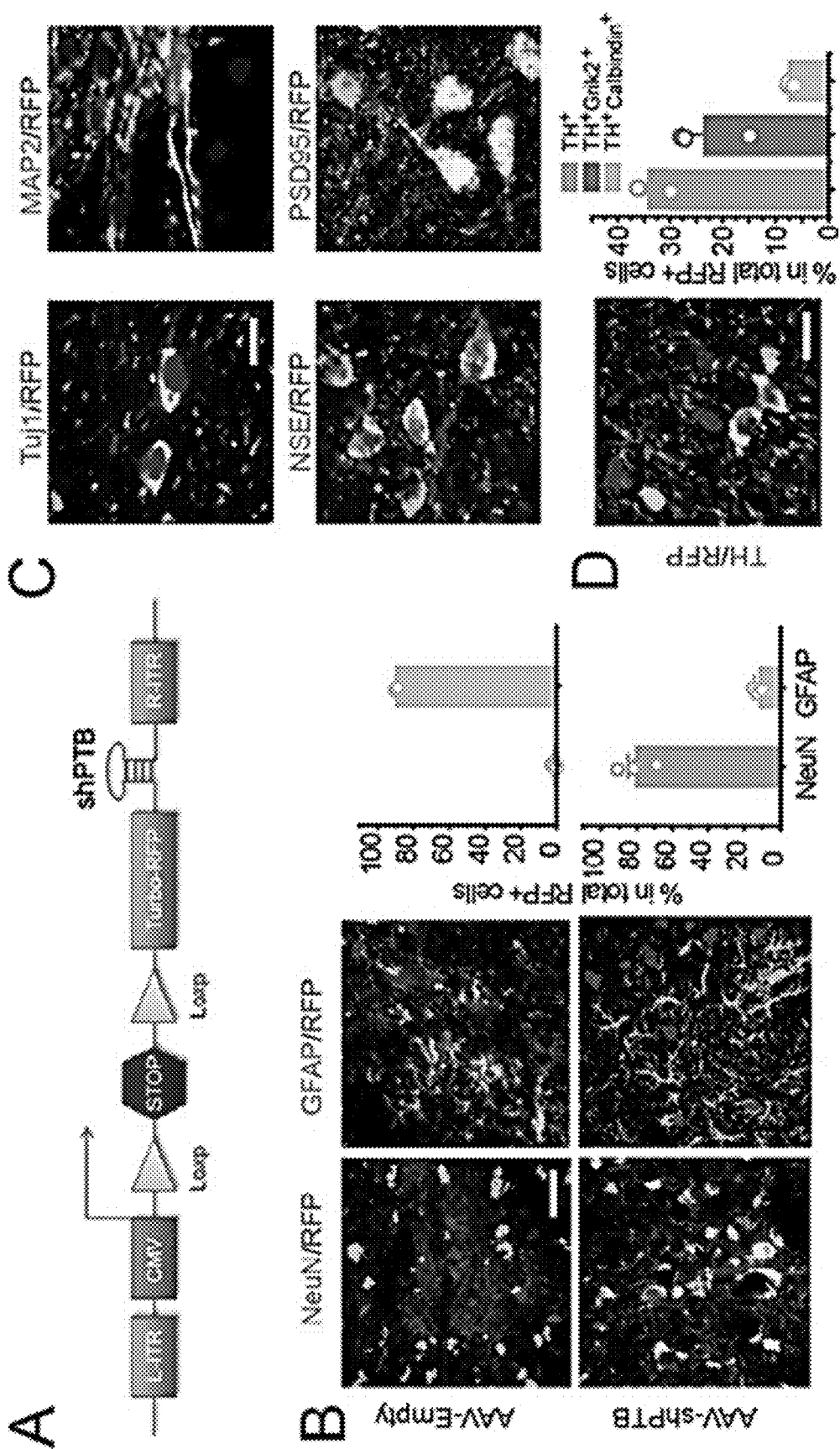
FIG. 7A-D

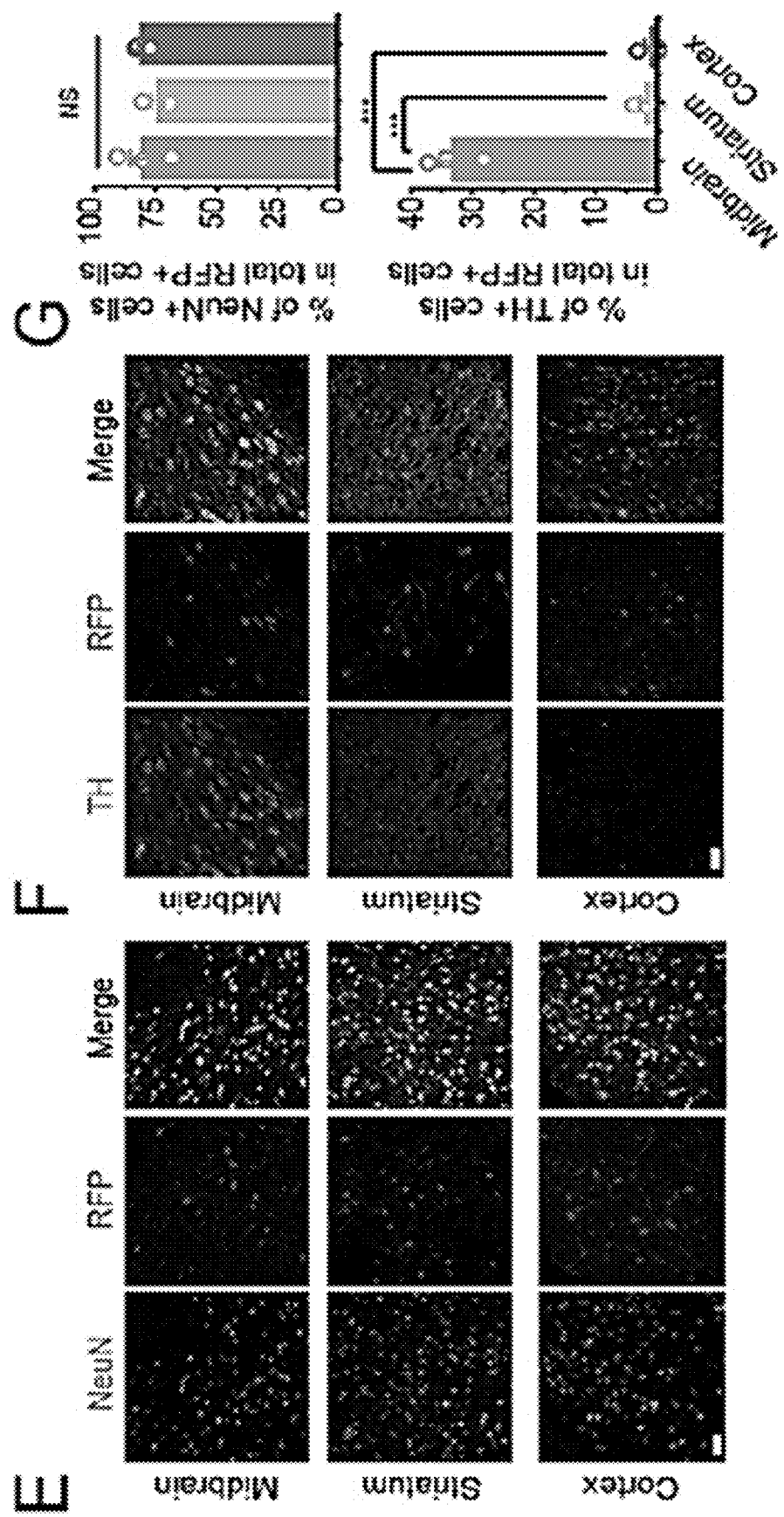
FIG. 7E-G

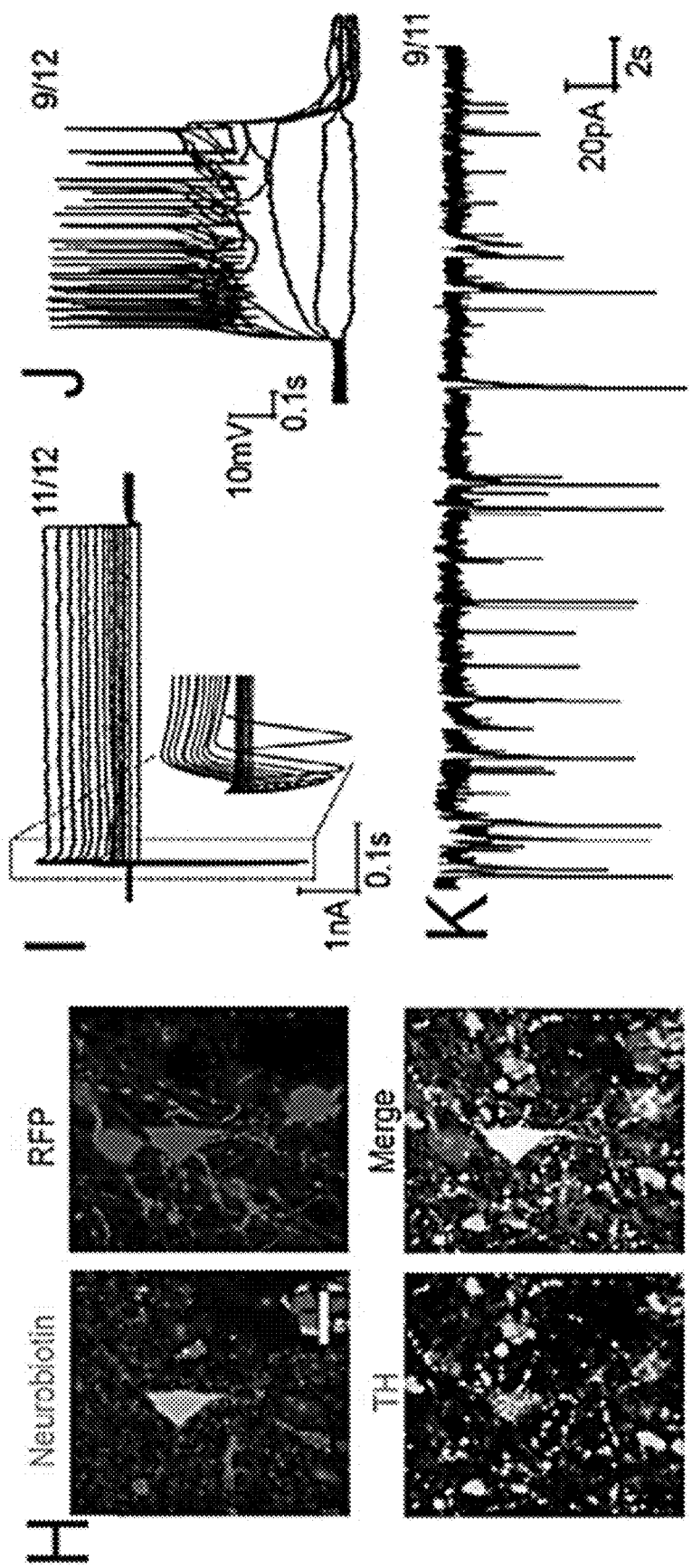
*FIG. 7H-K*

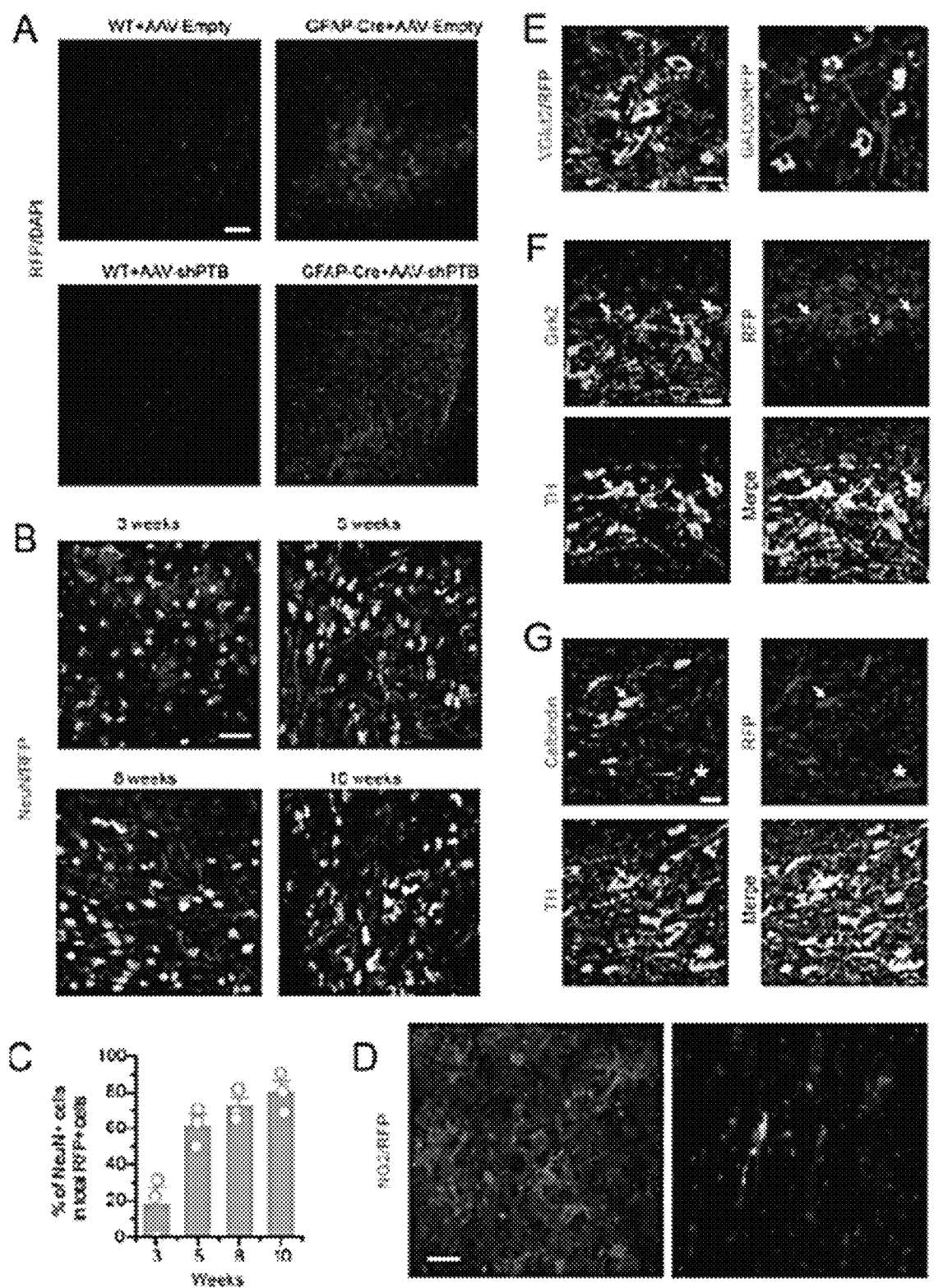
FIG. 8A-G

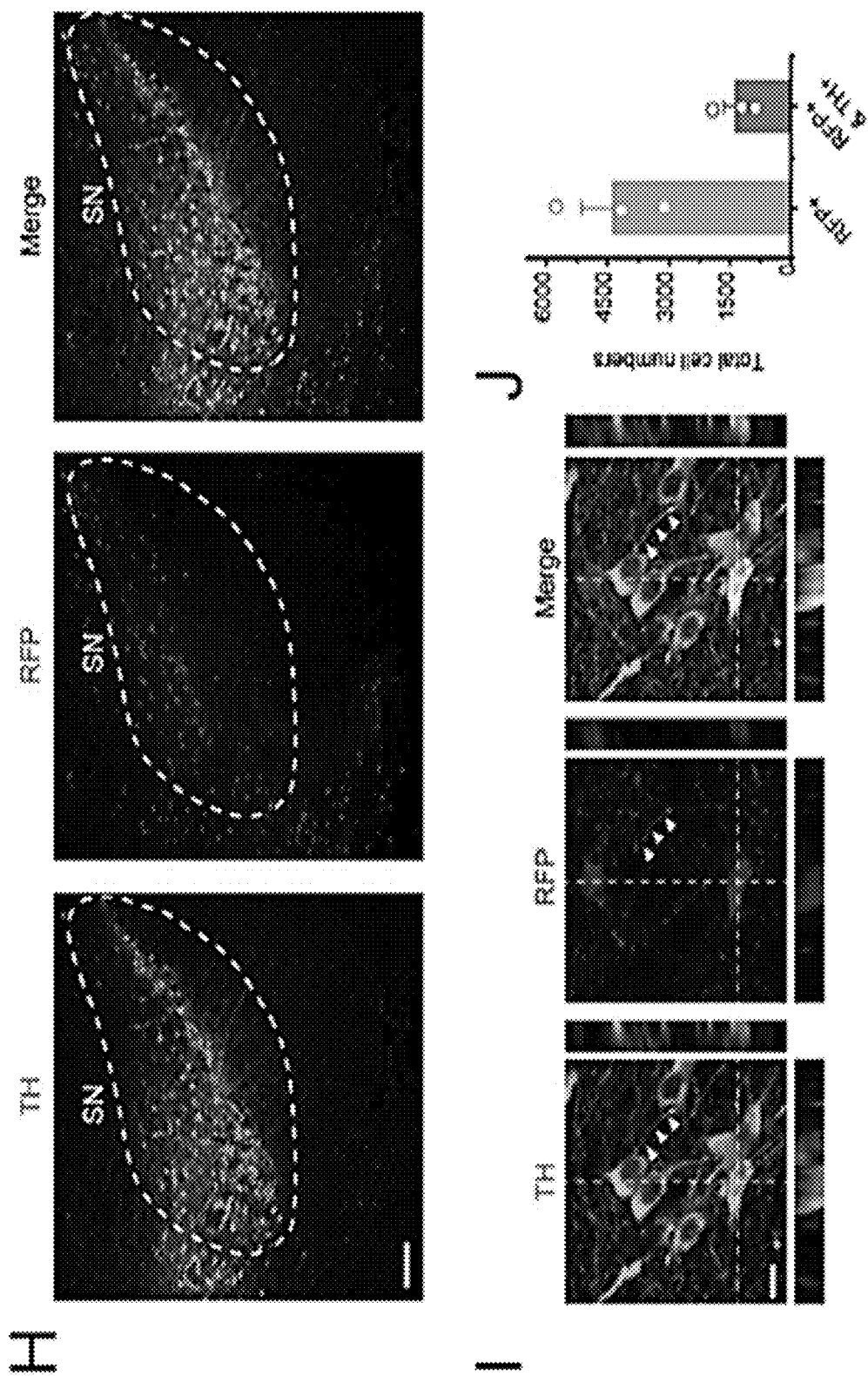
*FIG. 8H-J*

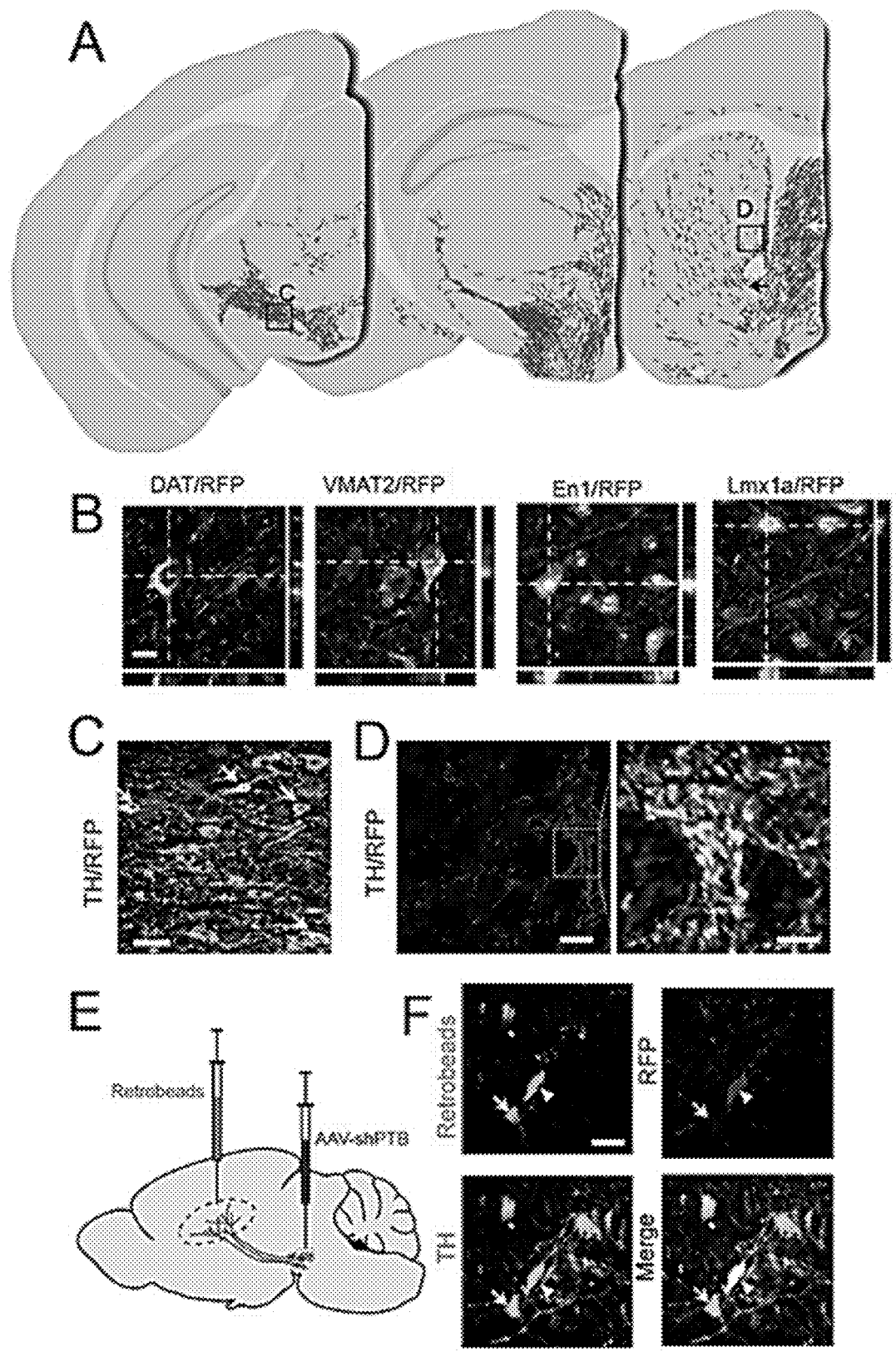
*FIG. 9A-F*

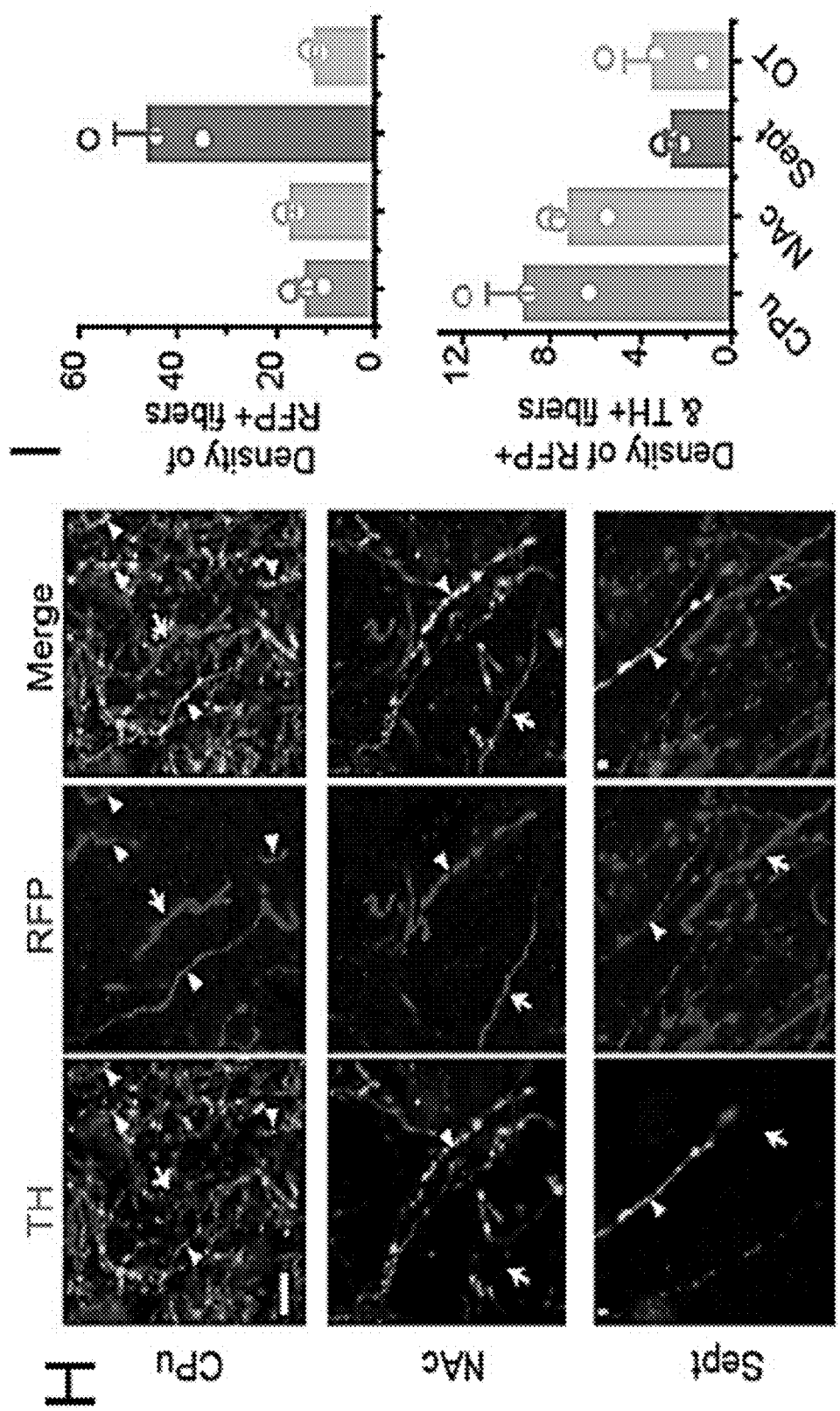
FIG. 9H-I

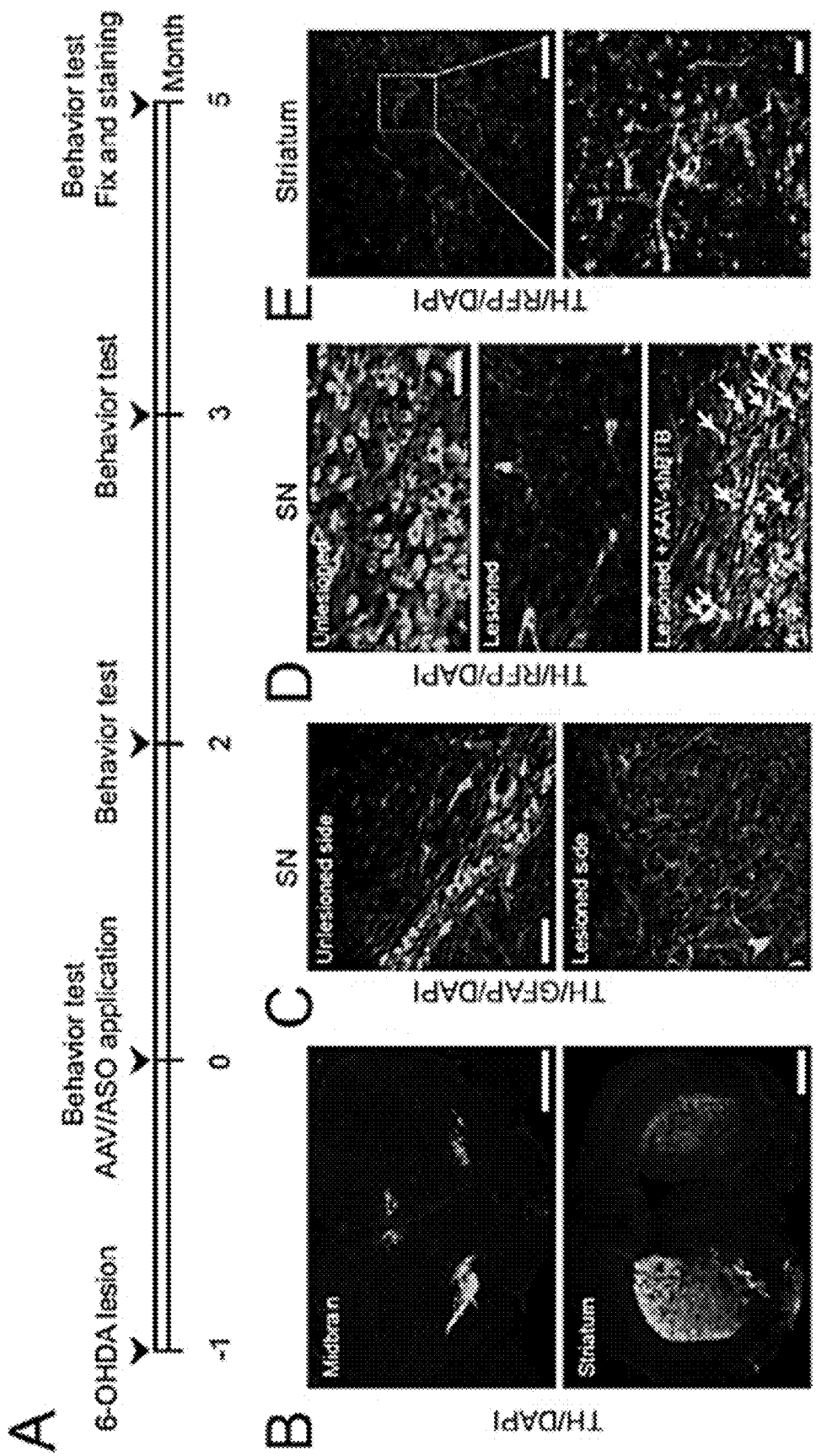
FIG. 11A-E

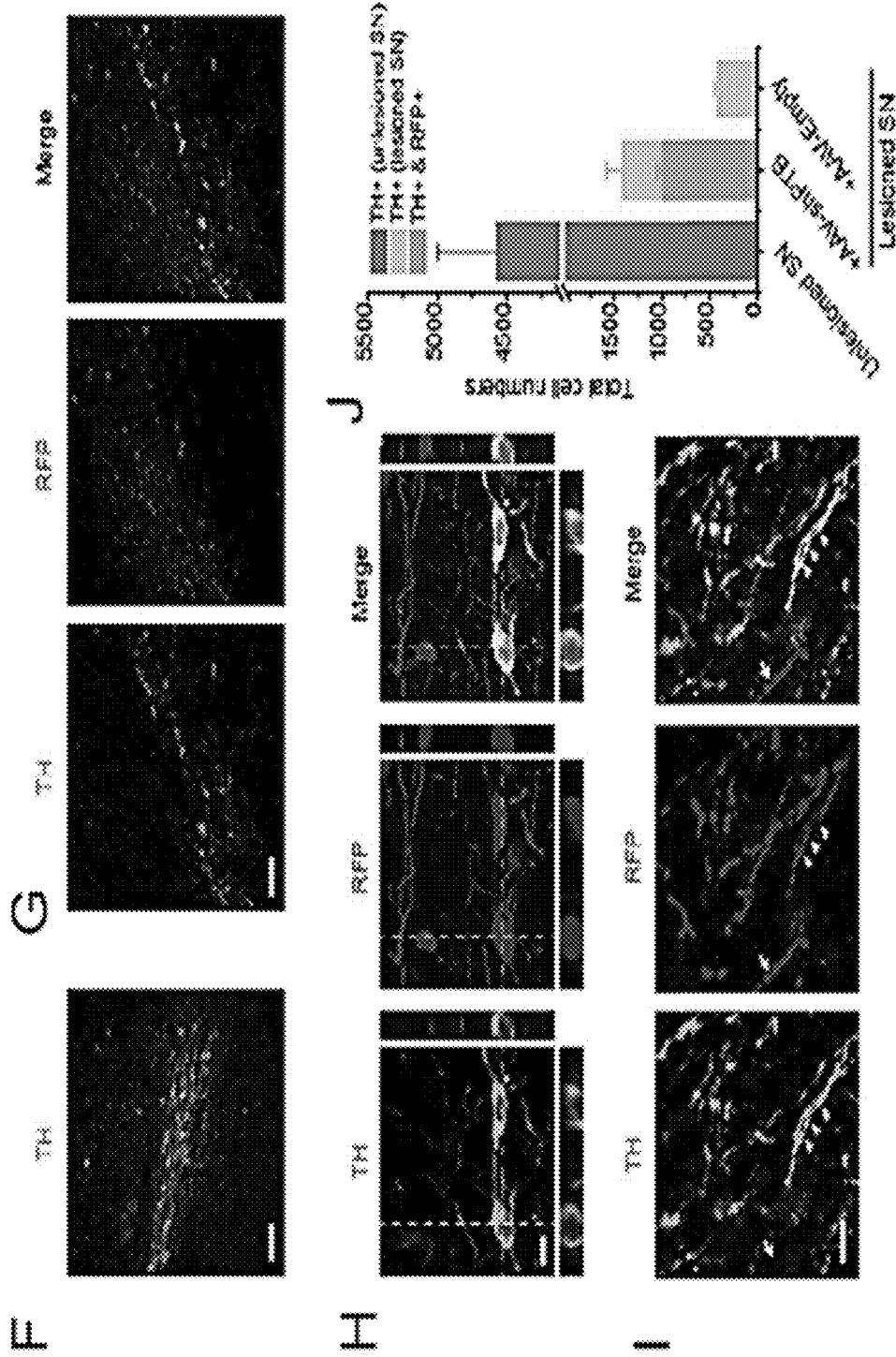
FIG. 11F-J

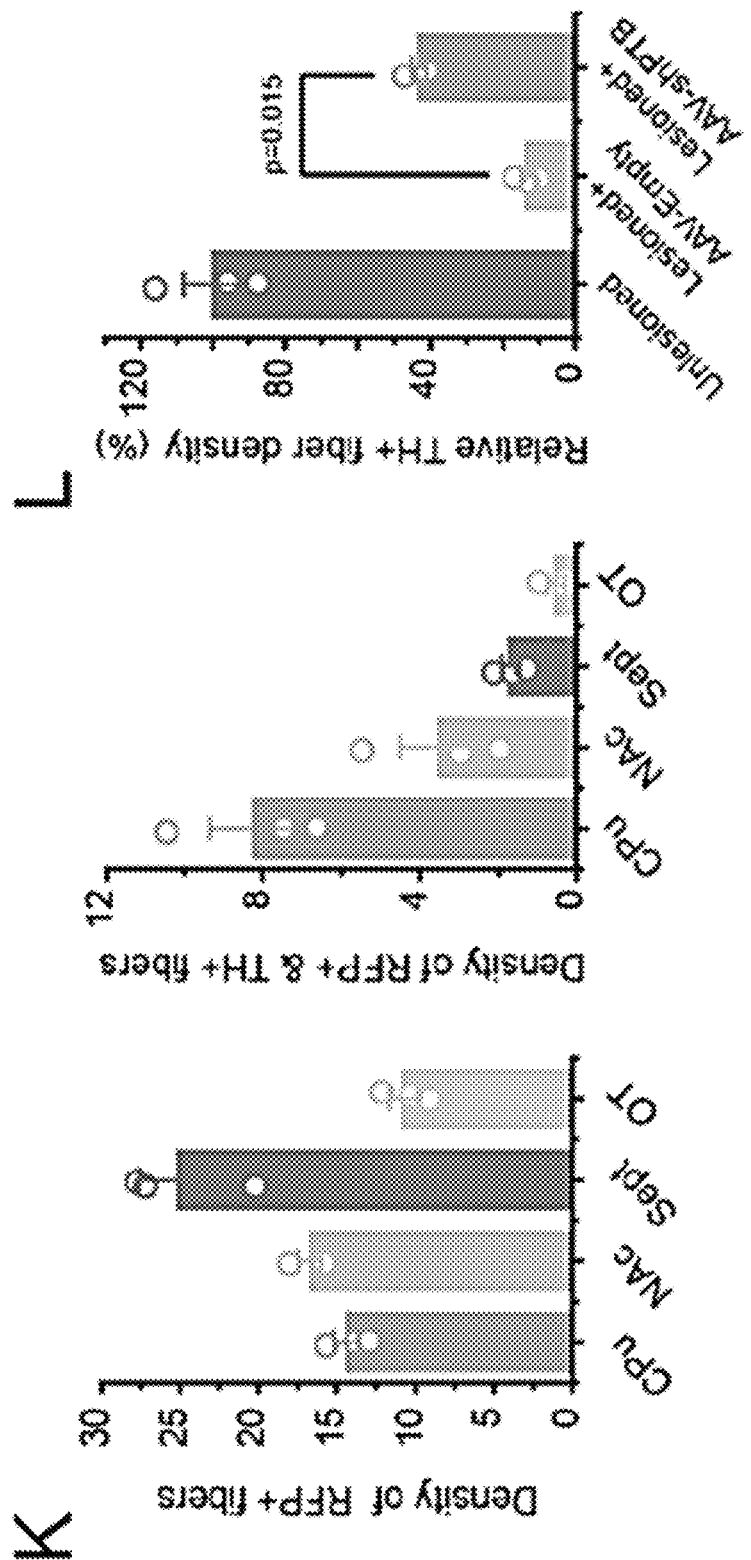
FIG. 11K-L

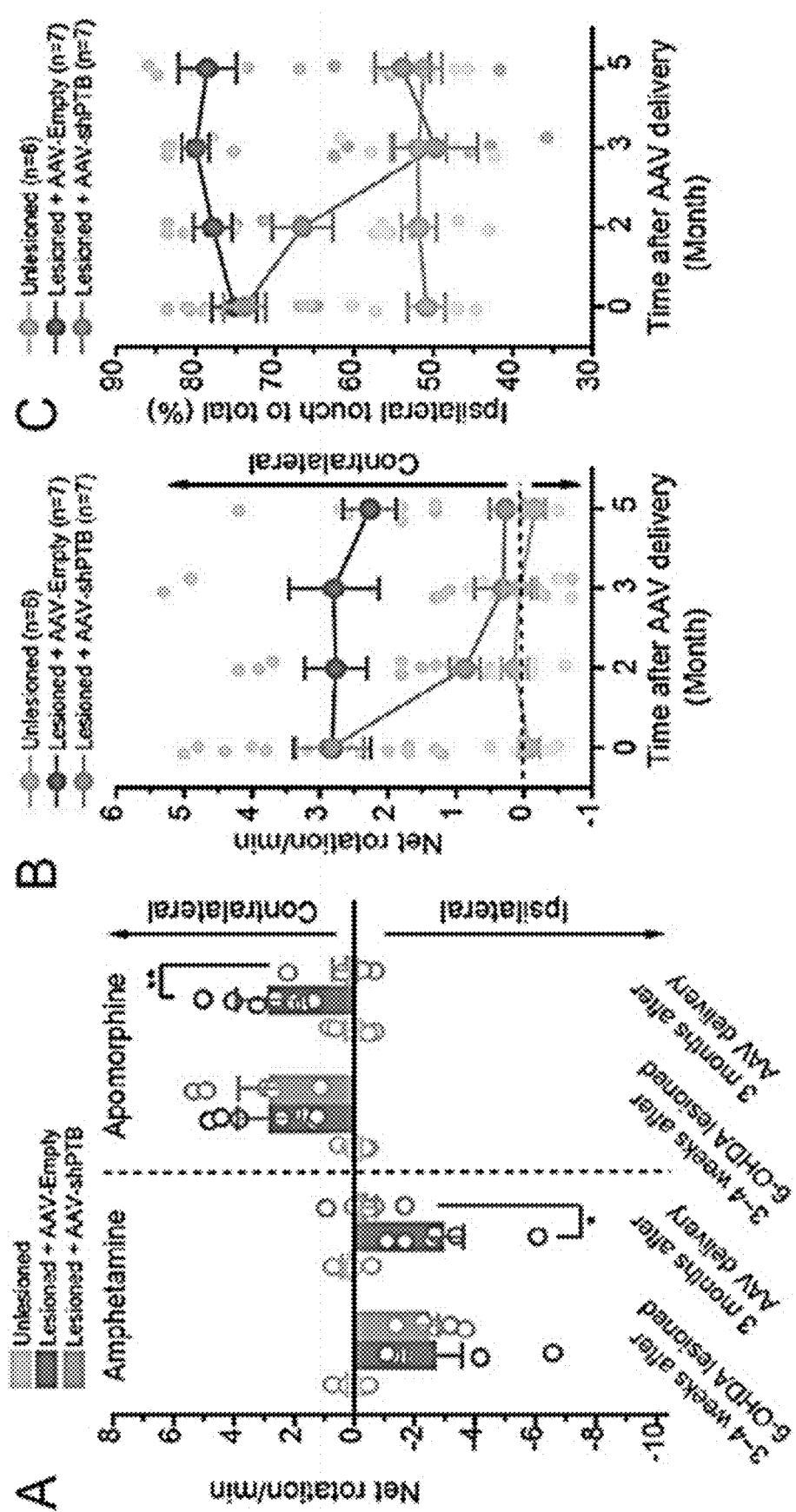
FIG. 12A-C

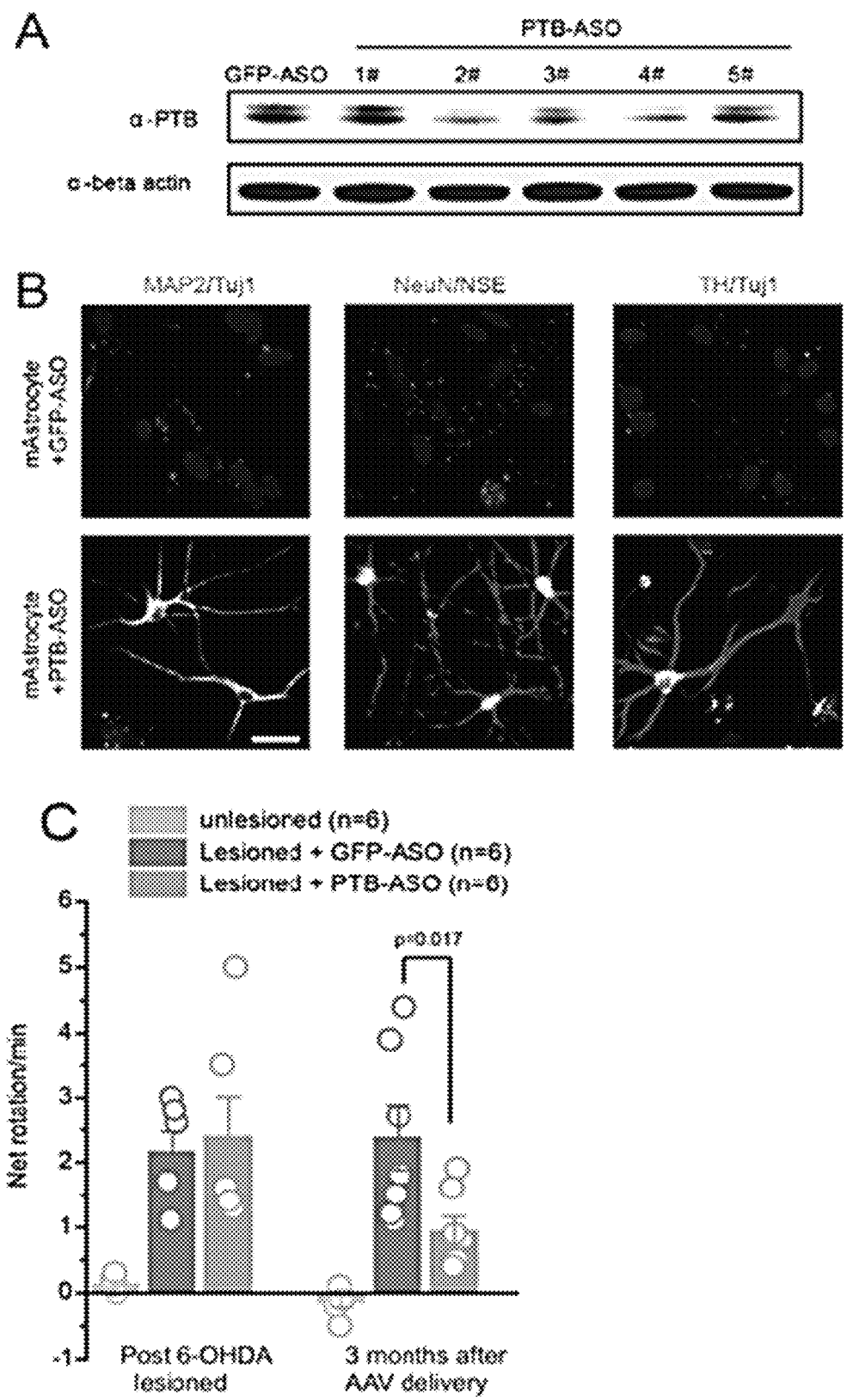
FIG. 13A-C

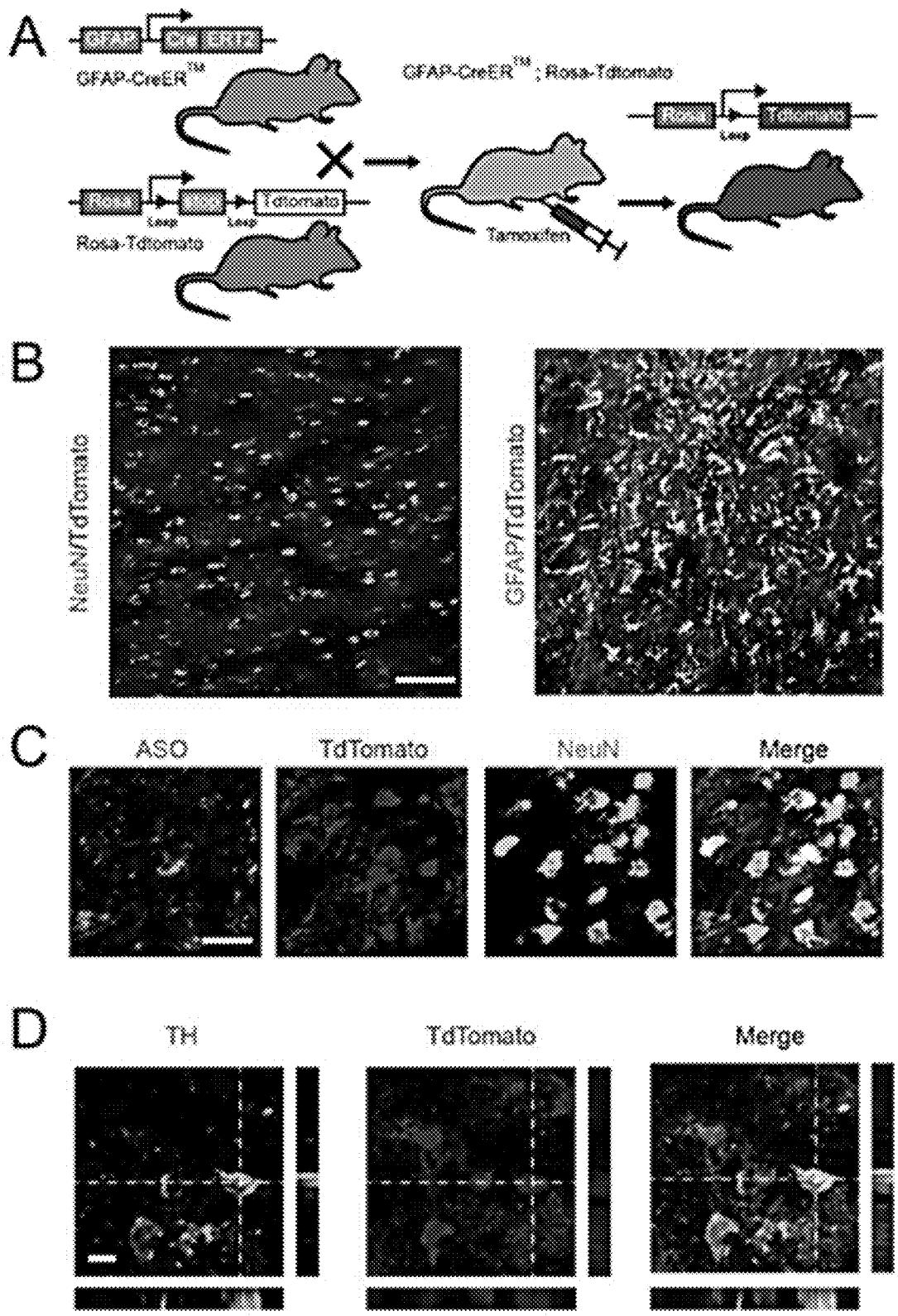
*FIG. 14A-D*

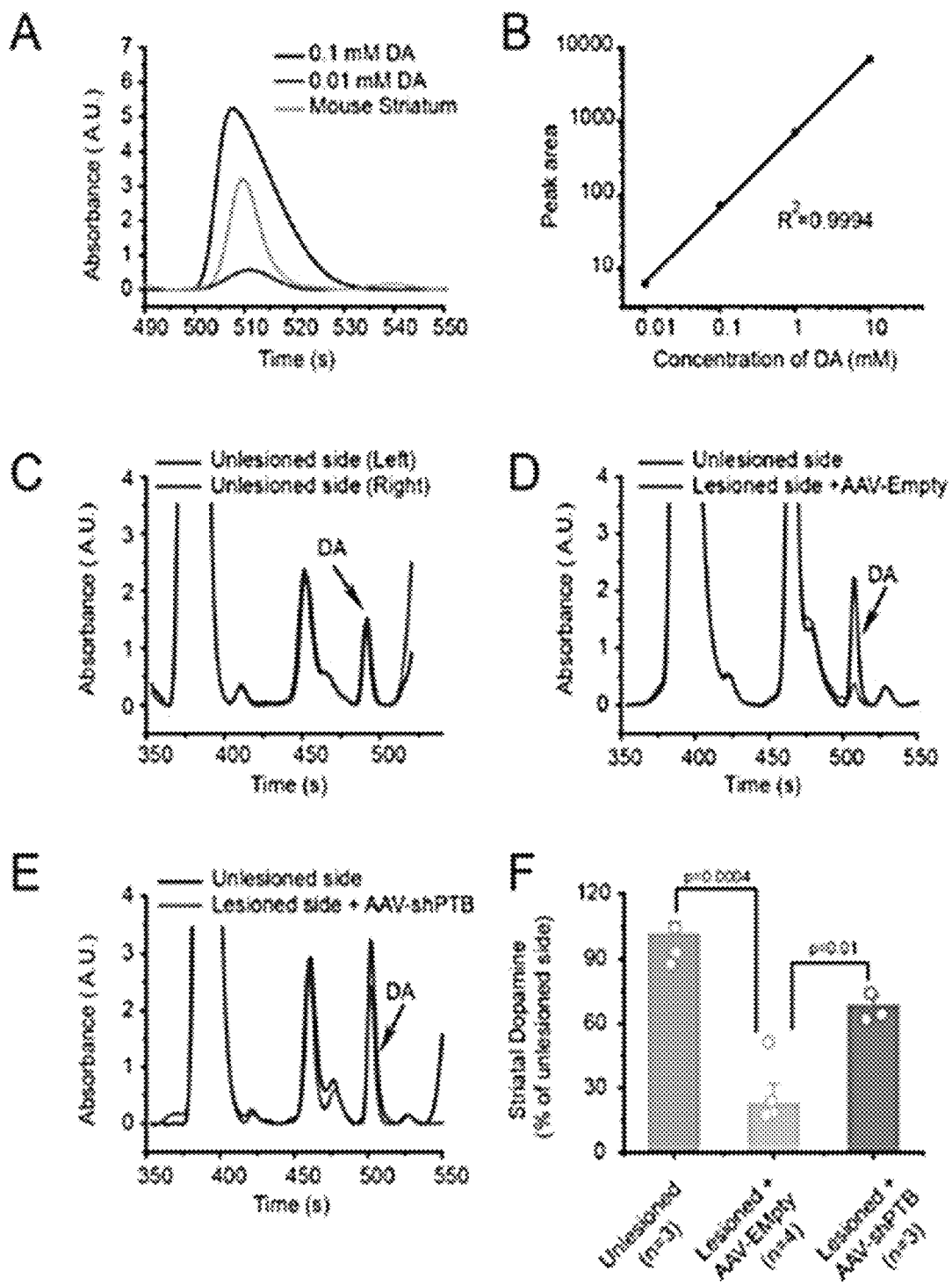
*FIG. 15A-F*

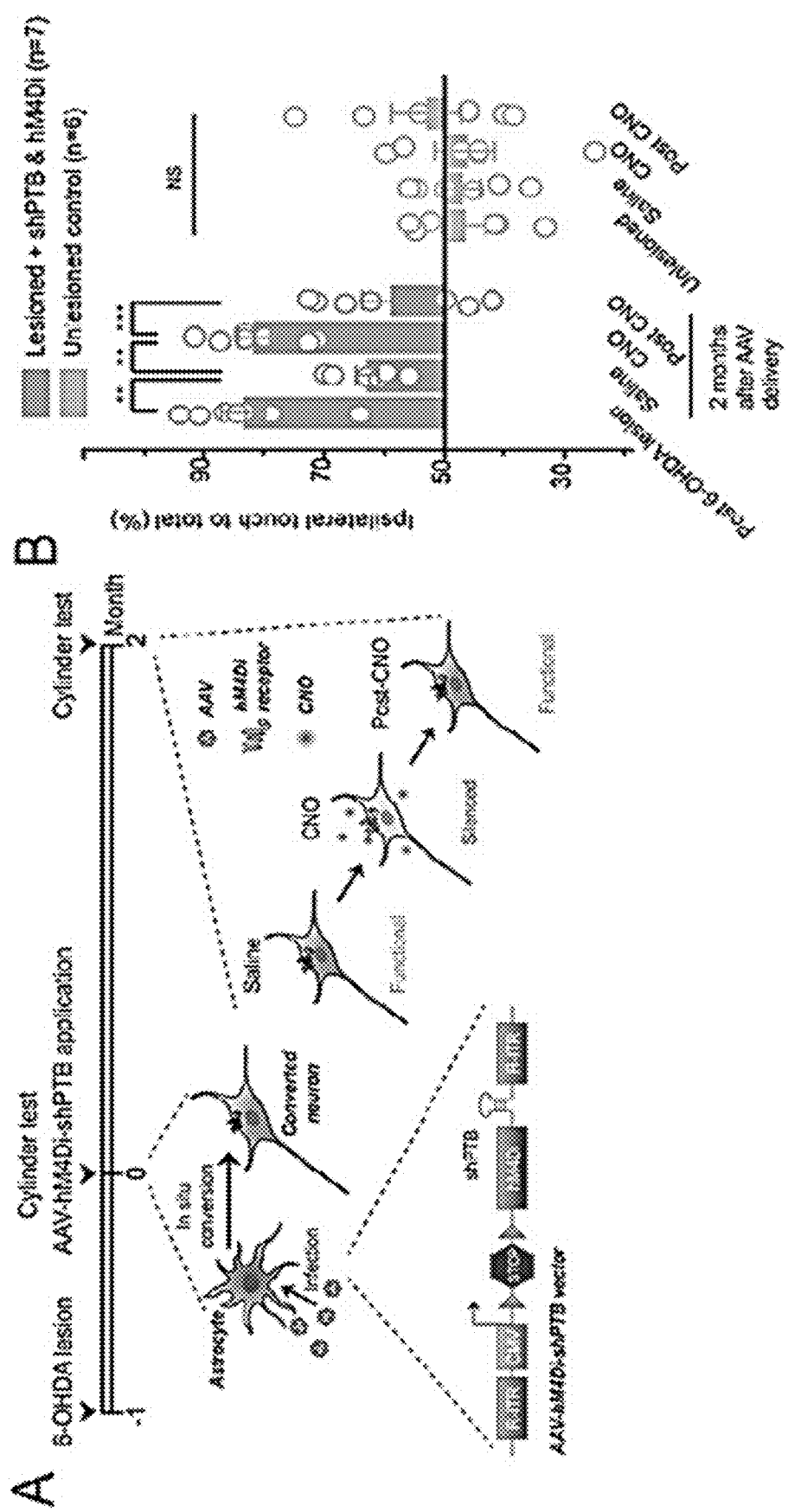
*FIG. 16A-B*

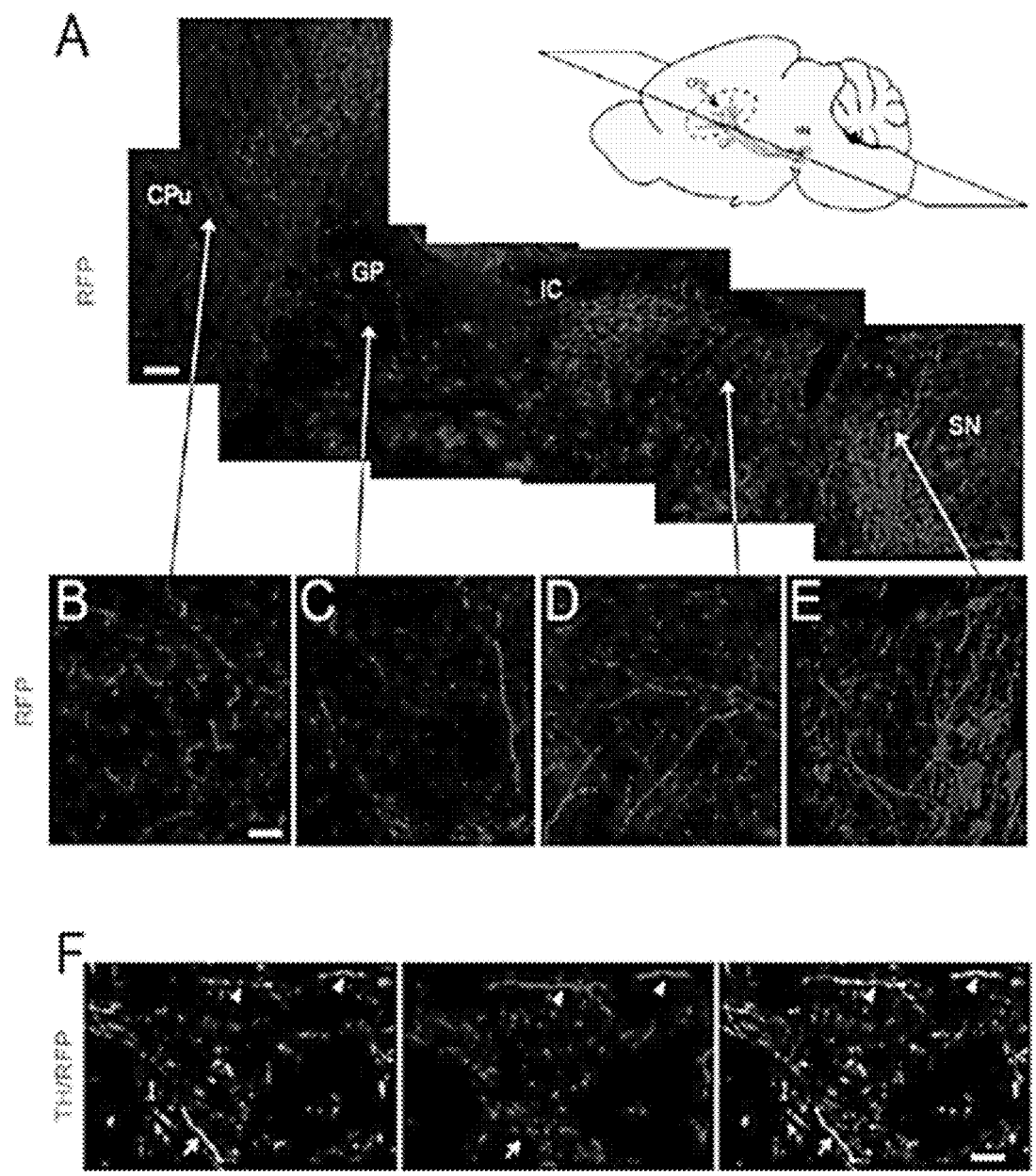
FIG. 17A-F

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Mouse shPTB

<400> SEQUENCE: 1
gggtgaagat cctgttcaat a        21

<210> SEQ ID NO 2
<211> LENGTH: 21
<212> TYPE: DNA
<213> ORGANISM: Artificial Sequence
<220> FEATURE:
<223> OTHER INFORMATION: Human shPTB

<400> SEQUENCE: 2
gcgtgaagat cctgttcaat a        21

<210> SEQ ID NO 3
<211> LENGTH: 21
<212> TYPE: DNA
<213> ORGANISM: Artificial Sequence
<220> FEATURE:
<223> OTHER INFORMATION: Antisense Oligonucleotide to Turbo GFP

<400> SEQUENCE: 3
gttggtgctc ttcatcttgt t        21

<210> SEQ ID NO 4
<211> LENGTH: 20
<212> TYPE: DNA
<213> ORGANISM: Artificial Sequence
<220> FEATURE:
<223> OTHER INFORMATION: U6-Forward Primer

<400> SEQUENCE: 4
acgcaaattc gtgaagcgtt        20

<210> SEQ ID NO 5
<211> LENGTH: 20
<212> TYPE: DNA
<213> ORGANISM: Artificial Sequence
<220> FEATURE:
<223> OTHER INFORMATION: miR-124 Forward Primer

<400> SEQUENCE: 5
taaggcacgc ggtgaatgcc        20

<210> SEQ ID NO 6
<211> LENGTH: 26
<212> TYPE: DNA
<213> ORGANISM: Artificial Sequence
<220> FEATURE:
<223> OTHER INFORMATION: miR-9 Forward Primer

<400> SEQUENCE: 6
gcgctctttg gttatctagc tgtatg        26

REPROGRAMMING OF NON-NEURONAL CELLS INTO NEURONS AND METHODS AND COMPOSITIONS TO TREAT NEURODEGENERATIVE DISEASES AND DISORDERS

CROSS REFERENCE TO RELATED APPLICATIONS

This application is a continuation of and claims priority to PCT/US2019/027027, filed Apr. 11, 2019, which application claims priority under 35 U.S.C. § 119 from Provisional Application Ser. No. 62/656,322, filed Apr. 11, 2018, and Provisional Application Ser. No. 62/718,774, filed Aug. 14, 2018, the disclosures of which are incorporated herein by reference.

GOVERNMENT LICENSE RIGHTS

This invention was made with government support under GM052872 and HG004659 awarded by the National Institutes of Health. The government has certain rights in the invention.

TECHNICAL FIELD

The disclosure relates to methods and composition for differentiating non-neuronal cells to neuronal cells and methods of treating neurodegenerative diseases and disorders.

INCORPORATION BY REFERENCE OF SEQUENCE LISTING

Accompanying this filing is a Sequence Listing entitled "Sequence_ST25.txt", created on Apr. 11, 2019 and having 1,595 bytes of data, machine formatted on IBM-PC, MS-Windows operating system. The sequence listing is hereby incorporated herein by reference in its entirety for all purposes.

BACKGROUND

Regenerative medicine has great promise for addressing disorders of cell loss. One approach employs cell replacement, while another utilizes cellular trans-differentiation. Cell replacement has enjoyed remarkable success in treating hematopoietic disorders; but in other diseases, this approach has either shown limited efficacy or is associated with risk of triggering immune responses and/or tumor formation. In contrast, trans-differentiation can take advantage of the existing cellular plasticity of endogenous cells to generate new cell types. The challenge is to identify efficient strategies to convert cells from one cell type to another, not only in culture but more importantly in their in vivo native contexts.

SUMMARY

The disclosure provides a neuronal cell produced by conversion of an astrocyte to a neuronal cell by: contacting the astrocyte with an inhibitory nucleic acid molecule that inhibits the expression of polypyrimidine-tract-binding (PTB) protein. In one embodiment or a further embodiment of the foregoing, the neuronal cell is produced in vitro. In one embodiment or a further embodiment of the foregoing, the neuronal cell is produced in vivo. In one embodiment or a further embodiment of the foregoing, the inhibitory nucleic acid molecule is an RNAi molecule. In one embodiment or a further embodiment of the foregoing, the RNAi molecule is a shRNA. In one embodiment or a further embodiment of the foregoing, the inhibitory nucleic acid molecule is an antisense molecule. In one embodiment or a further embodiment of the foregoing, the inhibitory nucleic acid molecule is in a virus or viral vector. In one embodiment or a further embodiment of the foregoing, the virus or viral vector is adenovirus, AAV, retrovirus, or lentivirus. In one embodiment or a further embodiment of the foregoing, the astrocyte is a human astrocyte.

The disclosure provides a method of treating a neurodegenerative disease or disorder comprising contacting an astrocyte in a subject having a neurodegenerative disease or disorder with an inhibitory nucleic acid the inhibits the expression of PTB, thereby differentiating the astrocyte to a neuron and treating the neurodegenerative disease or disorder. In one embodiment or a further embodiment of the foregoing, the inhibitory nucleic acid is delivered to a site in the central nervous system of brain of the subject associated with the neurodegenerative disease or disorder. In one embodiment or a further embodiment of the foregoing, the subject is a mammal. In one embodiment or a further embodiment of the foregoing, the mammal is a human. In one embodiment or a further embodiment of the foregoing, the neurodegenerative disease or disorder is selected from the group consisting of ischemic and hemorrhagic stroke, spinal cord injury, brain injury, Huntington's disease, Alzheimer's disease, Parkinson's disease, Schizophrenia, Autism, Ataxia, Amyotrophic Lateral Sclerosis, Lou Gehrig's Disease, Lyme Disease, Meningitis, Migraine, Motor Neuron Diseases, Neuropathy, pain, brain damage, brain dysfunction, spinal cord disorders, peripheral nervous system disorders, cranial nerve disorders, autonomic nervous system disorders, seizure disorders such as epilepsy, movement disorders such as Parkinson's disease, sleep disorders, headaches, lower back and neck pain, neuropathic pain, delirium and dementia such as Alzheimer's disease, dizziness and vertigo, stupor and coma, head injury, stroke, tumors of the nervous system, multiple sclerosis and other demyelinating diseases, infections of the brain or spinal cord, and prion diseases.

The disclosure also provides a method of treating a subject having a neurodegenerative disease or disorder comprising differentiating an astrocyte into a neuron and implanting the neuron into the subject at a site of neurodegeneration, wherein the astrocytes are converted to neurons by inhibiting the expression of PTB. In one embodiment or a further embodiment of the foregoing, the astrocytes are obtained from the subject at the site of the neurodegenerative disease or disorder and differentiated ex vivo.

The disclosure also provides a method for screening a drug or compound for activity in treating or inhibiting a neurodegenerative disease or disorder comprising obtaining an astrocyte from the subject with the neurodegenerative disease or disorder and differentiating the astrocyte to a neuronal cell by contacting the astrocyte with an inhibitory nucleic acid the inhibits PTB expression and contacting the neuronal cell with the drug or compound, and determining whether the drug or compound inhibits expression of any disease marker of the neurodegenerative disease or disorder.

In one embodiment or a further embodiment of the foregoing, the inhibitory nucleic acid comprises a sequence that is at least 80-100% identical to SEQ ID NO:1 or 2 and/or wherein T is U.

The disclosure also provide an antisense molecule comprising a sequence that is at least 98% identical to SEQ ID NO:2 and inhibits PTB expression and/or wherein T is U.

The disclosure also provides a vector comprising a sequence as set forth in SEQ ID NO:1 or 2, or a sequence that is at least 80-99% identical to said sequences and/or wherein T is U in said sequence (e.g., DNA or RNA) and wherein the vector inhibits PTB expression.

Disclosed herein, in certain embodiments, is a method of reprogramming a human non-neuronal cell to a mature neuron. In some embodiments, the method comprising: providing a human non-neuronal cell that expresses miR-9 or Brn2 at a level that is higher than that expressed in a human adult fibroblast; and contacting the cell with a composition comprising a cell-programming agent that suppresses expression or activity of PTB in the human non-neuronal cell, thereby reprogramming the human non-neuronal cell to a mature neuron.

In some embodiments, the human non-neuronal cell expresses miR-9 or Brn2 at a level that is at least two times higher than that expressed in a human adult fibroblast. In some embodiments, the human non-neuronal cell expresses miR-9 or Brn2 at a level that is at least ten times higher than that expressed in a human adult fibroblast. In some embodiments, the human non-neuronal cell expresses miR-9 and Brn2 at a level that is higher than that expressed in a human adult fibroblast.

Disclosed herein, in certain embodiments, is a method of reprogramming a human glial cell to a mature neuron, the method comprising: providing the human glial cell to be reprogrammed; and contacting the human glial cell with a composition comprising a cell-programming agent that suppresses expression or activity of PTB in the human glial cell for at least 1 day, thereby reprogramming the human glial cell to a mature neuron.

In some embodiments, the human glial cell is selected from the group consisting of: astrocyte, oligodendrocyte, ependymal cell, Schwan cell, microglia, and satellite cell. In some embodiments, the human glial cell is positive for GFAP (glial fibrillary acidic protein) or ALDH1L1 (Aldehyde Dehydrogenase 1 Family Member L1).

Disclosed herein, in certain embodiments, is a method of reprogramming an astrocyte to a mature neuron, the method comprising: providing the astrocyte to be reprogrammed; and contacting the astrocyte with a composition comprising a cell-programming agent that suppresses expression or activity of PTB in the astrocyte for at least 1 day, thereby reprogramming the astrocyte to a mature neuron.

In some embodiments, the astrocyte is a mouse astrocyte. In some embodiments, the method reprograms a plurality of mouse astrocytes, and wherein at least 60% of the mouse astrocytes are converted to mature neurons that are Tuj1 positive. In some embodiments, the method reprograms a plurality of mouse astrocytes, and wherein at least 40% of the mouse astrocytes are converted to mature neurons that are Map2 positive.

In some embodiments, the astrocyte is a human astrocyte. In some embodiments, the method reprograms a plurality of human astrocytes, in which at least 40%, at least 60%, or at least 80% of the human astrocytes are converted to mature neurons that are Tuj1 positive. In some embodiments, the method reprograms a plurality of human astrocytes, in which at least 20%, at least 40% or at least 60% of the human astrocytes are converted to mature neurons that are Map2 positive.

In some embodiments, the composition comprises a single cell-programming agent that specifically suppresses expression or activity of PTB.

Disclosed herein, in certain embodiments, is a method of reprogramming a human non-neuronal cell to a mature neuron, the method comprising: providing the human non-neuronal cell to be reprogrammed; and contacting the human non-neuronal cell with a composition comprising a single cell-programming agent that suppresses expression or activity of PTB in the human non-neuronal cell for at least 3 days, thereby reprogramming the human non-neuronal cell to a mature neuron.

Disclosed herein, in certain embodiments, is a method of reprogramming a human non-neuronal cell, the method comprising: providing the human non-neuronal cell to be reprogrammed; and contacting the human non-neuronal cell with a composition comprising a single cell-programming agent that yields a decrease in expression or activity of PTB in the human non-neuronal cell, and a decrease of expression or activity of nPTB after the expression or activity of PTB is decreased.

In some embodiments, an initial nPTB expression level increases to a high nPTB expression level as expression or activity of PTB is suppressed. In some embodiments, nPTB expression decreases from the high nPTB expression level to a low nPTB expression level that is higher than the initial nPTB expression level after expression or activity of PTB is suppressed. In some embodiments, the human non-neuronal cell expresses miR-9 or Brn2 at a level that is higher than that expressed in a human adult fibroblast. In some embodiments, the human non-neuronal cell expresses miR-9 and Brn2 at a level that is higher than that expressed in a human adult fibroblast.

In some embodiments, the method reprograms a plurality of the human non-neuronal cells, the human glial cells, or the astrocytes, in which at least 40% of the human non-neuronal cells, the human glial cells, or the astrocytes are reprogrammed to mature neurons that are characterized by expression of one or more neuronal markers selected from the group consisting of NeuN (neuronal nuclei antigen), Map2 (microtubule-associated protein 2), NSE (neuron specific enolase), 160 kDa neurofilament medium, 200 kDa neurofilament heavy, PDS-95 (postsynaptic density protein 95), Synapsin I, Synaptophysin, GAD67 (glutamate decarboxylase 67), GAD65 (glutamate decarboxylase 67), parvalbumin, DARPP32 (dopamine- and cAMP-regulated neuronal phosphoprotein 32), vGLUT1 (vesicular glutamate transporter 1), vGLUT2 (vesicular glutamate transporter 1), acetylcholine, and TH (tyrosine hydroxylase).

In some embodiments, the method reprograms a plurality of the human non-neuronal cells, the human glial cells, or the astrocytes, in which at least 20% of the human non-neuronal cells, the human glial cells, or the astrocytes are reprogrammed to functional neurons characterized in their abilities to establish action potential, synaptic connections, pre-synaptic neurotransmitter release, and/or post-synaptic response.

In some embodiments, the cell-programming agent is an anti-PTB inhibitor. In some embodiments, the anti-PTB inhibitor is an anti-PTB antisense oligonucleotide. In some embodiments, the anti-PTB inhibitor is selected from the group consisting of an anti-PTB shRNA, an anti-PTB miRNA, anti-PTB antisense oligonucleotide, an anti-PTB antibody, a small molecule inhibitor of PTB, a dominant negative PTB mutant, and a sponge polyribonucleotide containing polypyrimidine tract.

In some embodiments, the cell-programming agent suppresses the expression or activity of PTB for at least 5 days. In some embodiments, the cell-programming agent suppresses the expression or activity of PTB for at least 10 days. In some embodiments, the cell-programming agent suppresses the expression or activity of PTB for at least 15 days.

In some embodiments, the human non-neuronal cell, the human glial cell, or the astrocyte is cultured in a medium. In some embodiments, the medium comprises an agent selected from the group consisting of: an inhibitor of ALK5, an inhibitor of GSK3b, an activator of PKA, and any combinations thereof. In some embodiments, the activator ALK5 comprises SB431542. In some embodiments, the inhibitor GSK3b comprises CHIR99021. In some embodiments, the activator of PKA comprises dibutyryladenosine 3',5'-cyclic monophosphate (Db-cAMP). In some embodiments, the cell-programming agent is delivered in a lentiviral vector.

Disclosed herein, in certain embodiments, is a method of generating a functional neuron in vivo, comprising administering to a brain of a subject a composition comprising a cell-programming agent that suppresses expression or activity of PTB in an astrocyte in the brain, and allowing the astrocyte to reprogram into the functional neuron.

Disclosed herein, in certain embodiments, is a method of generating a functional neuron in vivo, comprising administering to a midbrain of a subject a composition comprising a cell-programming agent that suppresses expression or activity of PTB in a non-neuronal cell in the midbrain, and allowing the non-neuronal cell to reprogram into the functional neuron.

Disclosed herein, in certain embodiments, is a method of generating a dopaminergic neuron in vivo, comprising administering to a brain of a subject a composition comprising a cell-programming agent that suppresses expression or activity of PTB in a non-neuronal cell in the brain, and allowing the non-neuronal cell to reprogram into the dopaminergic neuron.

In some embodiments, the dopaminergic neuron expresses tyrosine hydroxylase (TH), dopamine transporter (DAT/SLC6A3), vesicular monoamine transporter 2 (VMAT2), engrailed homeobox 1 (En1), FoxA2, and/or LIM homeobox transcription factor 1 alpha (Lmx1a).

In some embodiments, the method reprograms a plurality of non-neuronal cells in the brain, and wherein at least 10% of the non-neuronal cells are converted to dopaminergic neurons. In some embodiments, the method reprograms a plurality of non-neuronal cells in the brain, and wherein at least 30% of the non-neuronal cells are converted to dopaminergic neurons.

In some embodiments, an axon terminal of the functional neuron or the dopaminergic neuron reaches striatum of the subject.

In some embodiments, the cell-programming agent is administered to substantia nigra of the subject.

In some embodiments, the subject is a human.

In some embodiments, the subject is a non-human animal.

Disclosed herein, in certain embodiments, is a method of generating a functional neuron in vivo, comprising administering to brain of a human subject a cell-programming agent that suppresses expression or activity of PTB in a non-neuronal cell in the brain, and allowing the non-neuronal cell to reprogram into the functional neuron.

In some embodiments, the non-neuron cell is a glial cell. In some embodiments, the glial cell is an astrocyte.

In some embodiments, the cell-programming agent is administered to midbrain, striatum, or cortex of the human subject. In some embodiments, the cell-programming agent is administered to substantia nigra of the human subject.

In some embodiments, the functional neuron is a dopaminergic neuron. In some embodiments, the functional neuron expresses tyrosine hydroxylase (TH), dopamine transporter (DAT), vesicular monoamine transporter 2 (VMAT2), engrailed homeobox 1 (En1), Forkhead Box A2 (FoxA2) and/or LIM homeobox transcription factor 1 alpha (Lmx1a).

In some embodiments, the functional neuron or the dopaminergic neuron exhibits presynaptic neurotransmitter. In some embodiments, the functional neuron or the dopaminergic neuron is integrated in existing neuronal circuitry in the brain.

In some embodiments, the method reprograms a plurality of the non-neuronal cells or the astrocytes in the brain, in which at least 30% of the non-neuronal cells or the astrocytes are reprogrammed into mature neurons that are characterized by expression of one or more neuronal markers selected from the group consisting of neuronal nuclei antigen (NeuN), microtubule-associated protein 2 (Map2), neuron specific enolase (NSE), 160 kDa neurofilament medium, 200 kDa neurofilament heavy, postsynaptic density protein 95 (PDS-95), Synapsin I, Synaptophysin, glutamate decarboxylase 67 (GAD67), glutamate decarboxylase 67 (GAD65), parvalbumin, dopamine- and cAMP-regulated neuronal phosphoprotein 32 (DARPP32), vesicular glutamate transporter 1 (vGLUT1), vesicular glutamate transporter 2 (vGLUT2), acetylcholine, and tyrosine hydroxylase (TH).

In some embodiments, the method reprograms a plurality of the non-neuronal cells or the astrocytes in the brain, in which at least 20% of the non-neuronal cells or the astrocytes are reprogrammed into functional neurons that are characterized in their abilities to establish action potential, synaptic connections, pre-synaptic neurotransmitter, and/or post-synaptic response.

In some embodiments, the cell-programming agent comprises an anti-PTB antisense oligonucleotide. In some embodiments, the cell-programming agent is selected from the group consisting of: an anti-PTB shRNA, an anti-PTB miRNA, anti-PTB antisense oligonucleotide, an anti-PTB antibody, a small molecule inhibitor of PTB, a dominant negative PTB mutant, a sponge polyribonucleotide containing polypyrimidine tract, and any combinations thereof.

In some embodiments, the cell-programming agent suppresses the expression or activity of PTB for at least 5 days. In some embodiments, the cell-programming agent suppresses the expression or activity of PTB for at least 10 days. In some embodiments, the cell-programming agent suppresses the expression or activity of PTB for at least 15 days. In some embodiments, the cell-programming agent is delivered in an AAV vector.

Disclosed herein, in certain embodiments, is a method of treating a neurological condition associated with degeneration of functional neurons in a brain region, comprising administering to the brain region of a subject in need thereof a composition comprising a cell-programming agent that suppresses expression or activity of PTB in a non-neuronal cell in the brain region, and allowing the non-neuronal cell to reprogram into a functional neuron, thereby replenishing the degenerated functional neurons in the brain region.

In some embodiments, the neurological condition is selected from the group consisting of: Parkinson's disease, Alzheimer's disease, Huntington's disease, Schizophrenia, depression, and drug addiction.

Disclosed herein, in certain embodiments, is a method of treating a neurological condition associated with degeneration of dopaminergic neurons in a brain region, comprising administering to the brain region of a subject in need thereof a composition comprising a cell-programming agent that suppresses expression or activity of PTB in a non-neuronal cell in the brain region, and allowing the non-neuronal cell to reprogram into a dopaminergic neuron, thereby replenishing degenerated dopaminergic neurons in the brain region.

Disclosed herein, in certain embodiments, is a method of restoring dopamine biogenesis in subject with a decreased amount of dopamine compared to a normal level, comprising administering to a brain region of the subject a composition comprising a cell-programming agent that suppresses expression or activity of PTB in a non-neuronal cell in the brain region, and allowing the non-neuronal cell to reprogram into a dopaminergic neuron, thereby restoring at least 50% of the decreased amount of dopamine.

In some embodiments, the non-neuronal cell is a glial cell. In some embodiments, the non-neuronal cell is an astrocyte.

In some embodiments, the cell-programming agent comprises an anti-PTB antisense oligonucleotide. In some embodiments, the single cell-programming agent is selected from the group consisting of: an anti-PTB shRNA, an anti-PTB miRNA, anti-PTB antisense oligonucleotide, an anti-PTB antibody, a small molecule inhibitor of PTB, a dominant negative PTB mutant, a sponge polyribonucleotide containing polypyrimidine tract, and any combinations thereof.

In some embodiments, the functional neuron or the dopaminergic neuron is integrated into existing neuronal circuitry in the brain region.

In some embodiments, the functional neuron or the dopaminergic neuron exhibits action potential, presynaptic neurotransmitter, and/or postsynaptic response.

In some embodiments, the cell-programming agent is administered to midbrain, striatum, or cortex of the subject. In some embodiments, the cell-programming agent is administered to substantia nigra of the subject.

In some embodiments, an axon terminal of the functional neuron or the dopaminergic neuron reaches striatum of the subject.

In some embodiments, the neurological disease is Parkinson's disease. In some embodiments, the administration of the cell-programming agent ameliorates one or more symptoms of Parkinson's disease. In some embodiments, the one or more symptoms of Parkinson's disease are selected from the group consisting of: tremor, stiffness, slowness, impaired balance, shuffling gait, postural instability, olfactory dysfunction, cognitive impairment, depression, sleep disorders, autonomic dysfunction, pain, and fatigue.

In some embodiments of the methods as provided herein, cell-programming agent comprises an antisense oligonucleotide conjugated with a cell-targeting moiety that is configured to suppress expression or activity of PTB in a target cell. In some embodiments, the cell-targeting moiety is configured to deliver the antisense oligonucleotide to the target cell. In some embodiments, the target cell comprises the non-neuronal cell, the glial cell, or the astrocyte. In some embodiments, the cell-target moiety comprises a polypeptide.

In some embodiments of the methods as provided herein, the cell-programming agent comprises a nucleic acid sequence that is at least 80%, at least 90%, or 100% identical to SEQ ID NO: 1 or 2.

Disclosed herein, in certain embodiments, is a pharmaceutical composition comprising a cell-programming agent in an amount effective to reprogram a mammalian non-neuronal cell to a mature neuron by suppressing expression or activity of PTB in the non-neuronal cell.

Disclosed herein, in certain embodiments, is a pharmaceutical composition as provided herein that is formulated for injection, inhalation, parenteral administration, intravenous administration, subcutaneous administration, intramuscular administration, intradermal administration, topical administration, or oral administration.

Disclosed herein, in certain embodiments, is an injectable composition comprising an antisense oligonucleotide configured to suppress expression or activity of PTB in a non-neuronal cell. In some embodiments, the non-neuronal cell is a glial cell. In some embodiments, the glial cell is an astrocyte. In some embodiments, the antisense oligonucleotide comprises a nucleic acid sequence that is at least 80%, at least 90%, or 100% identical to SEQ ID NO: 1 or 2.

Disclosed herein, in certain embodiments, is a composition comprising a lentiviral-shRNA construct configured to suppress expression or activity of PTB in a in a non-neuronal cell. In some embodiments, the non-neuronal cell is a glial cell. In some embodiments, the glial cell is an astrocyte. In some embodiments, the construct comprises a nucleic acid sequence that is at least 80%, at least 90%, or 100% identical to SEQ ID NO: 1 or 2.

Disclosed herein, in certain embodiments, is an injectable composition comprising an AAV-shRNA construct configured to suppress expression or activity of PTB in a non-neuronal cell. In some embodiments, the non-neuronal cell is a glial cell. In some embodiments, the glial cell is an astrocyte. In some embodiments, the construct comprises a nucleic acid sequence that is at least 80%, at least 90%, or 100% identical to SEQ ID NO: 1 or 2.

Disclosed herein, in certain embodiments, is a composition for converting a non-neuronal cell to a neuron, comprising an antisense oligonucleotide conjugated with a cell-targeting moiety configured to suppress expression or activity of PTB in the non-neuronal cell, wherein the cell-targeting moiety is configured to deliver the antisense oligonucleotide to the non-neuronal cell.

In some embodiments, the cell-targeting moiety comprises a polypeptide. In some embodiments, the cell-targeting moiety specifically is configured to specifically target the non-neuronal cell. In some embodiments, the non-neuronal cell is selected from the group consisting of: glial cell, adult primary fibroblast, embryonic fibroblast, epithelial cell, melanocyte, keratinocyte, adipocyte, blood cell, bone marrow stromal cell, Langerhans cell, muscle cell, rectal cell, and chondrocyte. In some embodiments, the non-neuronal cell is from a cell line selected from the group consisting of: glioblastoma cell, Hela cell line, NT2 cell line, ARPE19 cell line, and N2A cell line. In some embodiments, the non-neuronal cell is a glial cell. In some embodiments, the glial cell is selected from the group consisting of: astrocyte, oligodendrocyte, ependymal cell, Schwan cell, NG2 cell, and satellite cell. In some embodiments, the glial cell is an astrocyte. In some embodiments, the composition is for treating a neurological condition associated with degeneration of functional neurons in a brain region. In some embodiments, the neurological condition is selected from the group consisting of: Parkinson's disease, Alzheimer's disease, Huntington's disease, Schizophrenia, depression, and drug addiction. In some embodiments, the neurological condition is Parkinson's disease. In some embodiments, the antisense oligonucleotide comprises a nucleic acid sequence that is at least 80%, at least 90%, or 100% identical to SEQ ID NO: 1 or 2.

Disclosed herein, in certain embodiments, is an animal comprising a reprogrammed neuron in a brain region, wherein the reprogrammed neuron is made by any method as disclosed herein. In some embodiments, the animal is a mammal. In some embodiments, the animal is a human. In some embodiments, the animal is a rodent. In some embodiments, the animal is a pig.

Disclosed herein, in certain embodiments, is a brain tissue of any animal as disclosed herein comprising the reprogrammed neuron.

Disclosed herein, in certain embodiments, is a reprogrammed neuron made by one of the methods disclosed herein.

DESCRIPTION OF DRAWINGS

FIG. 5A shows that PTB knockdown-induced neurons from mouse astrocytes were immunopositive for pan-neuronal marker Tuj1 (red) and MAP2 (green). Mouse astrocytes infected with control virus (shCtrl) showed no positive staining of neuronal markers under same culture conditions. Right quantification based on 5 biological repeats. Scale bar: 100 um.

FIG. 5B shows the characterization of induced neurons by markers of mature neurons (NeuN, NSE) and markers of different neuronal subtypes, including markers of glutamatergic neurons (VGlut1), GABAergic neurons (GAD67) and dopaminergic neurons (TH). Scale bar: 30 um.

FIG. 5C shows quantification for subtypes of converted neurons from mouse astrocytes. Data from 4 biological repeats.

FIG. 5D shows electrophysiological analysis of induced neurons from mouse astrocytes, showing repetitive action potentials (left, 12 out of 18 examined cells showed the recorded activity) and large currents of voltage dependent sodium and potassium channels (middle, 13 out of 17 examined cells showed the recorded activity). After co-culture with rat astrocytes, spontaneous post-synaptic currents were also recorded (right, 10 out of 15 examined cells showed the recorded activity). Scale bar: 100 um.

FIG. 5E shows induced expression of Tuj1 (red) and MAP2 (green) by PTB knockdown in human astrocytes. Right panel shows quantification from 4 biological repeats.

FIG. 5F shows induced neurons from human astrocytes expressing markers of mature neurons (NeuN, NSE) and markers of different neural subtypes (VGlut1, GAD67 and TH). Scale bar: 40 um.

FIG. 5G shows quantification for subtypes of converted neurons from human astrocytes. Data from 5 biological repeats.

FIG. 5H shows electrophysiological analysis of induced neurons from human astrocytes, showing repetitive action potentials (left, 9 out of 11 examined cells showed the recorded activity), currents of voltage dependent sodium and potassium channels (middle, 17 out of 20 examined cells showed the recorded activity) and spontaneous post-synaptic currents (right, 13 out of 14 examined cells showed the recorded activity).

FIG. 5I shows graphs quantifying expression levels of SLC6A3 (left) and FoxA2 (right) measured by RT-qPCR in mouse cortical astrocytes before and after conversion to neurons with AAV-shPTB.

FIGS. 5J-K show exemplary images of induced dopaminergic neurons characterized by immunostaining for DAT (J) and VMAT2 (K). Scale bar: 20 um.

FIG. 5L shows quantification (based on three biological repeats) of the percentage of converted neurons that express DAP and VMAT2 in comparison with TH.

FIGS. 6A and 6C show spontaneous excitatory and inhibitory postsynaptic currents detected on mouse (FIG. 6A) and human (FIG. 6C) astrocytes after PTB knockdown-induced neuronal conversion, respectively, which were also demonstrated to be sequentially blocked by inhibitors against the excitatory (NBQX+APV) and inhibitory (PiTX) receptors.

FIGS. 6B and 6D show that mock mouse (FIG. 6B) and human astrocytes (FIG. 6D) did not show any neuronal electrophysiological properties, such as action potentials (top), currents of voltage-dependent channels (middle) and postsynaptic events (bottom), respectively.

FIG. 6E shows TH staining of shPTB-converted Tuj1-positive neurons from astrocytes derived from midbrain. Scale bar: 10 um.

FIG. 6F shows comparison of neuronal conversion efficiencies between astrocytes derived from cortex and midbrain, showing similar high percentage of Tuj1-positive neurons (left), but a significantly higher percentage of dopaminergic neurons converted from midbrain-derived astrocytes relative to that from cortex (right). ***p<0.001 (Student's t-test) based on three biological repeats.

FIG. 6G shows western blot results demonstrating the expression of a pan-neuronal marker (Tuj1) and two specific markers for dopaminergic neurons (TH, VMAT2) in astrocyte-derived neurons from cortex and midbrain.

FIGS. 7A-7K exemplify conversion of astrocytes into functional neurons by PTB down-regulation in mouse midbrain. (A) is a schematic illustration of the design of an AAV vector containing two loxP sites bracketing a stop signal followed by RFP and shRNA against PTB. (B) shows that empty vector-infected astrocytes showed GFAP positive staining but not NeuN staining (upper panels), and in contrast, most of astrocytes infected with shPTB-expressing vector were NeuN positive (lower panels), 10 weeks after infection. Quantified data from 3 mice are shown on the right. Scale bar: 30 um. (C) shows that converted neurons were immunopositive for multiple neuronal markers, including Tuj1, MAP2, NSE and PSD95. Scale bar: 10 um. (D) shows that a major population of converted neurons in the midbrain expressed TH. Right panel shows quantification for subgroups of converted dopaminergic neurons. Data were from 3 mice. Scale bar: 20 um. (E-G) show exemplary results suggestive of the specificity and efficiency of in situ converted dopaminergic neurons in different brain regions. (E) and (F) show immunostaining images of shPTB-induced mature neurons (NeuN) and dopaminergic neurons (TH) in midbrain, striatum and cortex. Arrowheads indicate several converted neuron cell bodies with overlapping signals for RFP and NeuN (A) or TH (B). Scale bar: 30 um. (G) shows quantification of the staining results in (E) and (F). Data were from three mice. Significant differences are indicated by the p-values from ANOVA with post-hoc Tukey test. (H) shows an exemplary patch clamp recording of converted neurons. The patched cell was labeled by Neurobiotin 488 filled in the recording pipette. Immunostaining after patch recording showed that the traced cell was TH positive. Scale bar: 20 um. (I-K) demonstrate that exemplary converted neurons on brain slices showed currents of voltage-dependent sodium and potassium channels (I, 11 out of 12 examined cells showed the recorded activity), repetitive action potentials (J, 9 out of 12 examined cells showed the recorded activity), and spontaneous post-synaptic currents (K, 9 out of 11 examined cells showed the recorded activity).

FIGS. 8A-8F show characterization of exemplary AAV-shPTB induced neuronal conversion in the mouse midbrain. (A) shows undetectable leakage of the LoxP-Stop-LoxP AAV expression unit in injected WT mice. RFP positive cells were rarely detected in the midbrain of wild type mouse (left) after injection of or AAV-Empty and AAV-shPTB virus, in comparison with GFAP-Cre transgenic mice that received the same viral injection (right). Scale bar: 150 um. (B) shows that RFP-positive cells were gradually converted to neurons in midbrain. The percentage of RFP-labeled NeuN positive cells was progressively increased from 3 to 10 weeks post-injection of AAV-shPTB. Scale bar: 50 um. (C) shows quantification of the data in (B) and other points that are not shown each based on 3 mice. (D) shows that NG2 cells were rarely detected around RFP-positive cells (left panel) whereas NG2-positive cells (right panel) were in general not surrounded by RFP-positive cells in the same slice of AAV-Empty transduced midbrain. Scale bar: 15 um. (E) shows immunostaining of glutamatergic neuron marker (VGluT2) and GABAergic neuron marker (GAD65) showed that different subtypes of converted neurons. Scale bar: 20 um. (F) shows immunostaining of the A9 dopaminergic neurons marker Girk2. Arrows indicate co-localization of Girk2 with RFP and TH stained signals. Scale bar: 20 um.

FIG. 8G shows immunostaining of the A10 dopaminergic neurons marker Calbindin. Arrows indicate co-localization of calbindin with RFP and TH signals. Star indicates a converted dopaminergic neuron (RFP and TH positive) that stained negatively for calbindin. Scale bar: 20 um.

FIG. 8H shows low magnification view of a substantia nigra injected with AAV-shPTB that also expresses a RFP for monitoring newly converted neurons, stained for TH in comparison with RFP-positive cells in this brain region. Scale bar: 100 um. These data are from unlesioned brain, showing a large number of endogenous TH-positive dopaminergic neurons (green). RFP-positive cells were detected within the substantia nigra (approximated by dashed line) as well as in surrounding regions.

FIG. 8I shows an amplified view of TH- and RFP-positive cell bodies in substantia nigra. A RFP and TH double positive cell body is highlighted by orthogonal views of z-stack images, which are attached on right and bottom of the main image in each panel. Arrowheads indicate a neuronal process positive for both TH and RFP. Scale bar: 10 um.

FIG. 8J shows quantification of total RFP-positive cells in comparison with converted dopaminergic neurons that express both RFP and TH in both substantia nigra and surrounding regions. Data are from three mice.

FIGS. 9A-9I show the characterization of projection of exemplary PTB knockdown-induced dopaminergic neurons from substantia nigra to striatum. (A) is an overview of RFP-positive fibers from exemplary converted neurons in mouse midbrain, showing three serial sections from dorsal to ventral. Top white arrow: septal nuclei; middle black arrow: nucleus accumbens; bottom yellow arrow: olfactory tubercle. (B) shows staining of converted cells for markers of dopaminergic neurons, including DAT (dopamine transporter), VMAT2 (vesicular monoamine transporter 2), Ent (engrailed homeobox 1) and Lmx1a (LIM homeobox transcription factor 1 alpha). Scale bar: 20 um. (C) shows TH and RFP positive cell bodies in the substantia nigra. Arrows indicate RFP and TH double positive cells. Scale bar: 30 um. (D) shows projection of RFP-positive fibers into striatum, some of those fibers were also stained positively for TH. Scale bar: 20 um (left); 10 um (right). (E) shows scheme for striatal injection of fluorescent retrograde axonal tracing beads into the mouse treated with AAV-shPTB earlier. (F) shows labeling of a TH/RFP-positive cell in substantia nigra with retrograde beads. Arrowhead indicates a beads-labeled converted cell and arrows point to a beads-labeled endogenous dopaminergic neuron (TH positive but RFP negative). Scale bar: 20 um. (G) shows a low magnification view of the striatum innervated by RFP-positive projections. Scale bar: 300 um. Inserted panels show the amplified views of RFP-positive projections in different regions. CPu: caudate-putamen; NAc: nucleus accumbens; Sept: septum; OT: olfactory tubercle. Scale bar: 15 um. (H) shows images of a fraction of RFP-positive fibers showed co-staining with TH (arrowheads), while others are TH-negative (arrows). Scale bar: 5 um. (I) shows quantification of densities of total RFP-positive fibers and RFP/TH-double positive fibers after transduction of AAV-shPTB in wild-type mouse brain. Data are based on images from three mice.

FIGS. 11A-11E exemplify reconstruction of the nigrostriatal pathway in a chemically-induced mouse PD model and rescue of the PD phenotype. (A) is a schematic of the experimental schedule for 6-OHDA-induced lesion in the substantia nigra (SN) followed by reprogramming with AAV-PTB and behavioral analysis. (B) shows induction of unilateral loss of TH-positive cell bodies in 6-OHDA-induced lesion in the midbrain (top, Scale bar: 500 um) and TH-stained fiber bundles in the striatum (bottom, Scale bar: 500 um). (D) shows the population of GFAP-positive astrocytes was dramatically increased in lesioned nigra. Scale bar: 50 um. (D) shows a comparison between control (top)

Figure 1:
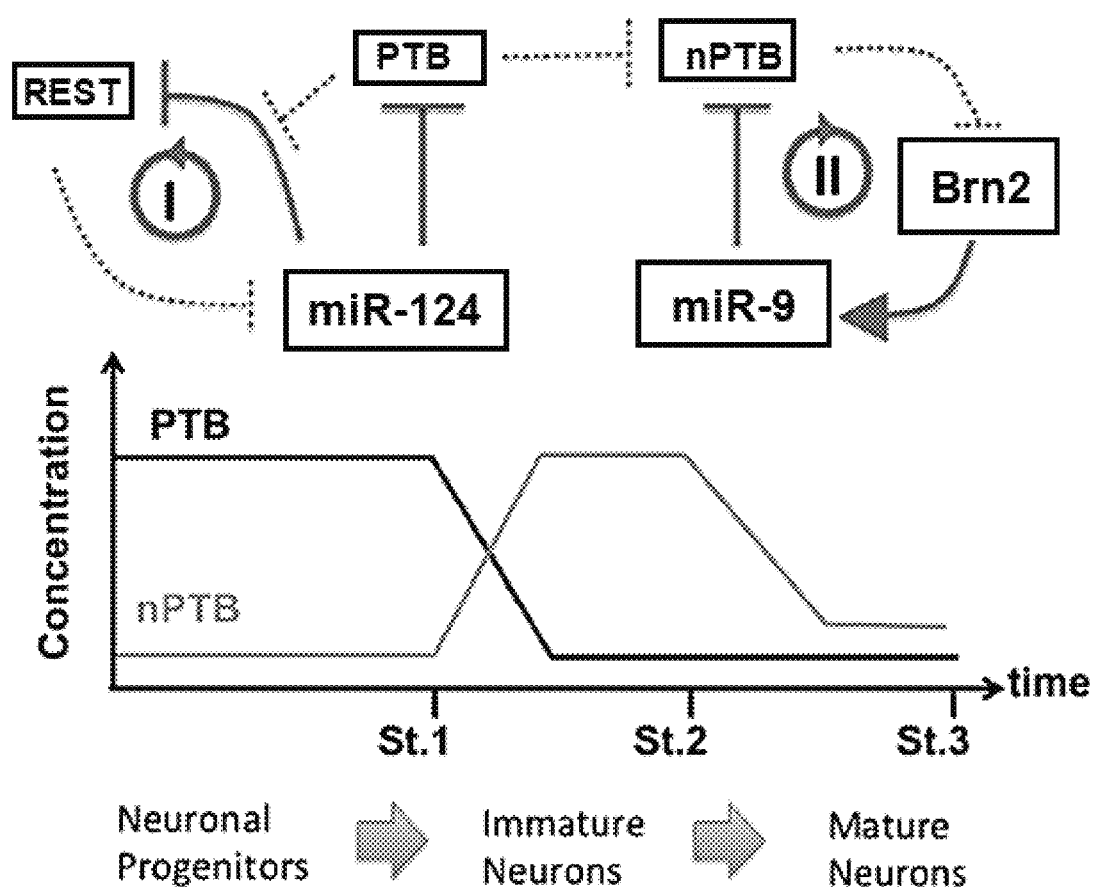
FIG. 1 is a schematic illustration of two consecutive regulatory loops controlled by PTB for neuronal induction and nPTB for neuronal maturation.

and 6-OHDA lesioned nigra (middle), demonstrating an increase in converted dopaminergic neurons (yellow, arrows) by AAV-shPTB (bottom), while stars indicate endogenous dopaminergic neurons (green). Scale bar: 50 um. (E) shows exemplary images of regenerated RFP and TH positive fibers in the striatum. Scale bar: 50 um (top); 10 um (bottom).

FIGS. 11F-11J show exemplary results demonstrating that shPTB-converted neurons replenished a significant fraction of lost dopaminergic neurons in the substantia nigra. (F) shows low magnification view of unlesioned substantia nigra stained for TH. Scale bar: 80 um. (G) shows the nigra lesioned with 6-OHDA and transduced with AAV-shPTB. Scale bar: 80 um. The nigra lesioned with 6-OHDA but treated with empty viral vector looked identical between lesioned but untreated nigra (not shown). (H) shows an enlarged view of RFP-positive cells co-expressing TH in substantia nigra. Scale bar: 10 um. Two RFP/TH-double positive cell bodies are highlighted by orthogonal views of z-stack images, attached on right and bottom of the main image in each panel. (I) shows images of RFP/TH-double positive processes (arrowheads) or RFP-positive, TH-negative processes (arrow) in nigra. Scale bar: 10 um. (J) shows quantification of dopaminergic neurons within an unlesioned side (blue), the remaining population of endogenous dopaminergic neurons within the lesioned side treated with empty vector (green), and converted RFP-positive dopaminergic neurons in the lesioned side (orange). Data are from two sets of images each from three mice treated with either AAV-shPTB or empty vector.

FIG. 11K shows graphs quantifying densities of total RFP-positive fibers and RFP/TH-double positive fibers in 6-OHDA lesioned brain after transduction with AAV-shPTB. Data are based on images from three mice.

FIG. 11L shows a graph quantifying optical densities of total TH-positive fibers in the striatum of unlesioned mice and lesioned mice transduced with AAV-shPTB, showing the restoration of TH-positive dopaminergic neurons in lesioned brain. Data are based on analysis of three mice in each group.

FIGS. 12A-12C demonstrate restoration of behavior to WT levels in 6-OHDA-treated, AAV-shPTB reprogrammed mice. (A) shows restoration of behavior in mock-treated, 6-OHDA-treated, AAV-shPTB reprogrammed mice. Rotation was induced by amphetamine (left, based on the data from 6 mice) or apomorphine (right, based on the data from 7 mice). (B) and (C) depict time course analysis of behavioral restoration in mock-treated, 6-OHDA treated, AAV-shPTB reprogrammed mice. Rotation was induced by apomorphine (B) and the percentage of ipsilateral touches (C) in unilateral lesioned mice was recorded. n=mice analyzed in each group. Statistical results represented as mean+/−SEM; significant differences are indicated by the p-values based on ANOVA with post-hoc Tukey test. * p<0.05; **p<0.01.

FIG. 13A shows a screen for efficient antisense oligonucleotides that target PTB. PTB levels were examined by western blot in mouse astrocytes treated with different ASOs. ASO 4 #was chosen for the rest of experiments.

FIG. 13B shows that an exemplary PTB-ASO induced neurons from mouse astrocytes, which were stained positively for Tuj1 and MAP2 (left), NSE and NeuN (middle), as well as the dopaminergic neuron marker TH (right). Mouse astrocytes treated with GFP-ASO showed no positive staining of any of the neuronal markers under same culture conditions (not shown). Scale bar: 20 um.

FIG. 13C shows that PTB-ASO, but not GFP-ASO, rescued the rotation behavior induced by apomorphine in 6-OHDA lesioned mice. Statistical results represented as mean+/−SEM; * p<0.01 based on unpaired Student's t test.

FIGS. 14A-14D show that an exemplary PTB-ASO induced neuronal conversion of astrocyte in mouse midbrain. (A) is a schematic of transgenic mice used to label and tracing astrocytes in vivo. (B) shows that in the midbrain of the double transgenic GFAP-CreER:Rosa-tdTomato mouse, none of tdTomato-labeled cells were stained positive for NeuN (left), but most of them were GFAP positive (right), 3 weeks after treatment of tamoxifen, Scale bar: 50 um. (C) shows that a portion of tdTomato-labeled cells became NeuN positive 8 weeks after injection of PTB-ASO in the midbrain. Scale bar: 20 um. (D) shows that an exemplary PTB-ASO converted neurons were stained positive for the dopaminergic neuron marker TH. Scale bar: 15 um.

FIG. 15A-F shows AAV-shPTB treatment significantly restored the striatal dopamine level. (A) shows a graph depicting dopamine levels in brain detected by HPLC after two different doses of "spike-in" dopamine" added within the range of dopamine in wild-type brain. (B) shows a standard curve generated by "spike-in" dopamine added to different levels. (C) and (D) depict comparison of striatal dopamine levels in two sides of the unlesioned brain (C) and reduction of striatal dopamine in response to unilateral 6-OHDA lesion (D). (E) shows significant restoration of striatal dopamine after injection of AAV-shPTB in ipsilateral nigra. (F) is a graph quantifying striatal dopamine levels under different conditions as indicated. n: the number of mice analyzed in each group. Significant differences are indicated by the p-values in ANOVA with post-hoc Tukey test.

FIG. 16A is schematic depiction of the chemogenetic approach to demonstrate converted neurons are directly responsible for the phenotypic recovery.

FIG. 16B is a graph quantifying the behavior results of the chemogenetic experiment, where cylinder test was conducted to show preferential ipsilateral touches in lesioned mice before and after injecting AAV-hM4Di-shPTB as well as treatment with CNO and 3 days after drug withdrawal. Unlesioned mice served as control. n=mice analyzed in each group.

FIGS. 17A-F depict reconstruction of the nigral-striatal pathway by converted dopaminergic neurons. (A) shows images of RFP-positive projections extended from nigra to striatum. Schematic figure shows the dorso-ventral level of horizontal section. Scale bar: 100 um. CPu, caudate-putamen; GP, globus pallidus; IC, internal capsule; SN, substantia nigra. (B)-(E) show higher magnification views of different brain regions. Scale bar: 25 um. (F) shows images of a portion of RFP-positive fibers co-stained with TH (arrowheads) in globus pallidus. Arrow indicates an endogenous dopaminergic fiber. Scale bar: 5 um.

DETAILED DESCRIPTION

As used herein and in the appended claims, the singular forms "a," "an," and "the" include plural referents unless the context clearly dictates otherwise. Thus, for example, reference to "an inhibitor" includes a plurality of inhibitors and reference to "the agent" includes reference to one or more agents and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications, patents, and patent applications mentioned herein are incorporated herein by reference in full for the purpose of describing and disclosing the methodologies, which are described in the publications, which might be used in connection with the description herein, as if each individual publication, patent, or patent application was specifically and individually indicated to be incorporated by reference. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

"Astrocyte" can refer to characteristic star-shaped glial cells in the brain and spinal cord. As would be clear to one skilled in the art, astrocytes can be characterized in their star shape, expression of markers like glial fibrillary acidic protein (GFAP) and aldehyde dehydrogenase 1 family member L1 (ALDH1L1), excitatory amino acid transporter 1/glutamate aspartate transporter (EAAT1/GLAST), glutamine synthetase, 5100 beta, or excitatory amino acid transporter 1/glutamate transporter 1 (EAAT2/GLT-1), participation of blood-brain barrier together with endothelial cells, transmitter uptake and release, regulation of ionic concentration in extracellular space, reaction to neuronal injury and participation in nervous system repair, and metabolic support of surrounding neurons. In certain embodiments of the present disclosure, an astrocyte can refer to a non-neuronal cell in a nervous system that expresses glial fibrillary acidic protein (GFAP), Aldehyde Dehydrogenase 1 Family Member L1 (ALDH1L1), or both. In certain embodiments, an astrocyte can refer to a non-neuronal cell in a nervous system that expresses a glial fibrillary acidic protein (GFAP) promoter-driven transgene (e.g., red fluorescent protein (RFP), Cre recombinase).

A "BRN2 transcription factor" or "Brain-2 transcription factor," also called "POU domain, class 3, transcription factor 2" ("POU3F2") or "Oct-7," can refer to a class III POU-domain transcription factor, having a DNA-binding POU domain that consists of an N-terminal POU-specific domain of about 75 amino acids and a C-terminal POU-homeo domain of about 60 amino acids, which are linked via a linker comprising a short a-helical fold, and which can be predominantly expressed in the central nervous system. BRN2 can be expressed in the central nervous system and can interact with the proneural basic-helix-loop-helix transcription factor Mashl to regulate aspects of neurogenesis, such as neuronal differentiation.

As used herein, the term "contacting" cells with a composition of the disclosure refers to placing the composition (e.g., compound, nucleic acid, viral vector etc.) in a location that will allow it to touch the cell in order to produce "contacted" cells. The contacting may be accomplished using any suitable method. For example, in one embodiment, contacting is by adding the compound to a culture of cells. Contacting may also be accomplished by injecting it or delivering the composition to a location within a body such that the composition "contacts" the cell type targeted.

As used herein, the term "differentiation", of "differentiate" or "coverting" of "inducing differentiation" are used interchangeably to refer to changing the default cell type (genotype and/or phenotype) to a non-default cell type (genotype and/or phenotype). Thus "inducing differentiation in an astrocyte cell" refers to inducing the cell to change its morphology from an astrocyte to a neuronal cell type (i.e., change in gene expression as determined by genetic analysis such as a microarray) and/or phenotype (i.e. change in expression of a protein.

As used herein, the term "glial cell" can generally refer to a type of supportive cell in the central nervous system (e.g., brain and spinal cord) and the peripheral nervous system. In some embodiments, unlike neurons, glial cells do not conduct electrical impulses or exhibit action potential. In some embodiments, glial cells do not transmit information with each other, or with neurons via synaptic connection or electrical signals. In a nervous system or in an in vitro culture system, glial cells can surround neurons and provide support for and insulation between neurons. Non-limiting examples of glial cells include oligodendrocytes, astrocytes, ependymal cells, Schwann cells, microglia, and satellite cells.

The terms "iRNA", "RNAi agent," "iRNA agent,", "RNA interference agent" as used interchangeably herein, refer to an agent that contains RNA, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of PTB in a cell, e.g., a cell within a subject, such as a mammalian subject. RNAi agents include, without limitation, "small interfering RNA (siRNA)", "endoribonuclease-prepared siRNA (e-siRNA)", "short hairpin RNA (shRNA)", and "small temporally regulated RNA (stRNA)"; "diced siRNA (d-siRNA)", and aptamers, oligonucleotides and other synthetic nucleic acids that comprise at least one uracil base. In some embodiments, such RNAi agents are delivered by a vector such as, but not limited to, a replication defective or replication competent viral vector (e.g., adenoviral vectors, lentiviral vectors, gammaretroviral vectors etc.).

A "microRNA" or "miRNA" refers to a non-coding nucleic acid (RNA) sequence that binds to at least partially complementary nucleic acid sequence (mRNAs) and negatively regulates the expression of the target mRNA at the post-transcriptional level. A microRNA is typically processed from a "precursor" miRNA having a double-stranded, hairpin loop structure to a "mature" form. Typically, a mature microRNA sequence is about 19-25 nucleotides in length.

"miR-9" is a short non-coding RNA gene involved in gene regulation and highly conserved from *Drosophila* and mouse to human. The mature ~21 nt miRNAs are processed from hairpin precursor sequences by the Dicer enzyme. miR-9 can be one of the most highly expressed microRNAs in developing and adult vertebrate brain. Key transcriptional regulators such as FoxG1, Hes1 or Tlx, can be direct targets of miR-9, placing it at the core of the gene network controlling the neuronal progenitor state.

As used herein, the term "neuron" or "neuronal cell" as used herein can have the ordinary meaning one skilled in the art would appreciate. In some embodiments, neuron can refer to an electrically excitable cell that can receive, process, and transmit information through electrical signals (e.g., membrane potential discharges) and chemical signals (e.g., synaptic transmission of neurotransmitters). As one skilled in the art would appreciate, the chemical signals (e.g., based on release and recognition of neurotransmitters) transduced between neurons can occur via specialized connections called synapses. As used herein, the term "mature neuron" can refer to a differentiated neuron. In some embodiments, a neuron is the to be a mature neuron if it expresses one or more markers of mature neurons, e.g., microtubule-associated protein 2 (MAP2) and Neuronal Nuclei (NeuN), neuron specific enolase (NSE), 160 kDa neurofilament medium, 200 kDa neurofilament heavy, post-synaptic density protein 95 (PDS-95), Synapsin I, Synaptophysin, glutamate decarboxylase 67 (GAD67), glutamate decarboxylase 67 (GAD65), parvalbumin, dopamine- and cAMP-regulated neuronal phosphoprotein 32 (DARPP32), vesicular glutamate transporter 1 (vGLUT1), vesicular glutamate transporter 2 (vGLUT2), acetylcholine, and tyrosine hydroxylase (TH). As used herein, the term "functional neuron" can refer to a neuron that is able to send or receive information through chemical or electrical signals. In some embodiments, a functional neuron exhibits one or more functional properties of a mature neuron that exists in a normal nervous system, including, but not limited to: excitability (e.g., ability to exhibit action potential, e.g., a rapid rise and subsequent fall in voltage or membrane potential across a cellular membrane), forming synaptic connections with other neurons, pre-synaptic neurotransmitter release, and post-synaptic response (e.g., excitatory postsynaptic current or inhibitory postsynaptic current). In some embodiments, a functional neuron is characterized in its expression of one or more markers of functional neurons, including, but not limited to, synapsin, synaptophysin, glutamate decarboxylase 67 (GAD67), glutamate decarboxylase 67 (GAD65), parvalbumin, dopamine- and cAMP-regulated neuronal phosphoprotein 32 (DARPP32), vesicular glutamate transporter 1 (vGLUT1), vesicular glutamate transporter 2 (vGLUT2), acetylcholine, tyrosine hydroxylase (TH), dopamine, vesicular GABA transporter (VGAT), and gamma-aminobutyric acid (GABA).

As used herein, the term "non-neuronal cell" can refer to any type of cell that is not a neuron. An exemplary non-neuronal cell is a cell that is of a cellular lineage other than a neuronal lineage (e.g., a hematopoietic lineage). In some embodiments, a non-neuronal cell is a cell of neuronal lineage but not a neuron, for example, a glial cell. In some embodiments, a non-neuronal cell is somatic cell that is not neuron, such as, but not limited to, glial cell, adult primary fibroblast, embryonic fibroblast, epithelial cell, melanocyte, keratinocyte, adipocyte, blood cell, bone marrow stromal cell, Langerhans cell, muscle cell, rectal cell, or chondrocyte. In some embodiments, a non-neuronal cell is from a non-neuronal cell line, such as, but not limited to, glioblastoma cell line, Hela cell line, NT2 cell line, ARPE19 cell line, or N2A cell line. "Cell lineage" or "lineage" can denote the developmental history of a tissue or organ from the fertilized embryo. "Neuronal lineage" can refer to the developmental history from a neural stem cell to a mature neuron, including the various stages along this process (as known as neurogenesis), such as, but not limited to, neural stem cells (neuroepithelial cells, radial glial cells), neural progenitors (e.g., intermediate neuronal precursors), neurons, astrocytes, oligodendrocytes, and microglia.

The terms "nucleic acid" and "polynucleotide" as used interchangeably herein can refer to deoxyribonucleotides or ribonucleotides and polymers thereof in either single- or double-stranded form. The term can encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, locked nucleic acids (LNAs), and peptide-nucleic acids (PNAs).

"Oligodendrocyte" can refer to a type of glial call that can create myelin sheath that surrounds a neuronal axon to provide support and insulation to axons in the central nervous system. Oligodendrocyte can also be characterized in their expression of PDGF receptor alpha (PDGFR-α), SOX10, neural/glial antigen 2 (NG2), Olig 1, 2, and 3, oligodendrocyte specific protein (OSP), Myelin basic protein (MBP), or myelin oligodendrocyte glycoprotein (MOG).

"Polypyrimidine tract binding protein" or "PTB" and its homolog neural PTB (nPTB) are both ubiquitous RNA-binding proteins. PTB can also be called polypyrimidine tract-binding protein 1, and in humans is encoded by the PTBP1 gene. PTBP1 gene belongs to the subfamily of ubiquitously expressed heterogeneous nuclear ribonucleoproteins (hnRNPs). The hnRNPs are RNA-binding proteins and they complex with heterogeneous nuclear RNA (hnRNA). These proteins are associated with pre-mRNAs in the nucleus and appear to influence pre-mRNA processing and other aspects of mRNA metabolism and transport. PTB can have four repeats of quasi-RNA recognition motif (RRM) domains that bind RNAs. Consistent with its widespread expression, PTB can contribute to the repression of a large number of alternative splicing events. PTB can recognize short RNA motifs, such as UCUU and UCUCU, located within a pyrimidine-rich context and often associated with the polypyrimidine tract upstream of the 3' splice site of both constitutive and alternative exons. In some cases, binding site for PTB can also include exonic sequences and sequences in introns downstream of regulated exons. In most alternative splicing systems regulated by PTB, repression can be achieved through the interaction of PTB with multiple PTB binding sites surrounding the alternative exon. In some cases, repression can involve a single PTB binding site. Splicing repression by PTB can occur by a direct competition between PTB and U2AF65, which in turn can preclude the assembly of the U2 snRNP on the branch point. In some cases, splicing repression by PTB can involve PTB binding sites located on both sides of alternative exons, and can result from cooperative interactions between PTB molecules that would loop out the RNA, thereby making the splice sites inaccessible to the splicing machinery. Splicing repression by PTB can also involve multimerization of PTB from a high-affinity binding site that can create a repressive wave that covers the alternative exon and prevents its recognition.

PTB can be widely expressed in non-neuronal cells, while nPTB can be restricted to neurons. PTB and nPTB can undergo a programmed switch during neuronal differentiation. For example, as illustrated in FIG. 1, during neuronal differentiation, PTB is gradually down-regulated at the neuronal induction stage, coincidentally or consequentially, nPTB level is gradually upregulated to a peak level. Later, when the neuronal differentiation enters into neuronal maturation stage, nPTB level experiences reduction after its initial rise and then returns to a relatively low level as compared to the its peak level during neuronal differentiation, when the cell develops into a mature neuron.

The sequences of PTB are known (see e.g., Romanelli et al. (2005) Gene, August 15:356:11-8; Robinson et al., PLoS One. 2008 Mar. 12; 3(3):e1801. doi:10.1371/journal.pone.0001801; Makeyev et al., Mol. Cell (2007) August 3; 27(3):435-48); thus, one of skill in the art can design and construct antisense, miRNA, siRNA molecules and the like to modulate, e.g., to decrease or inhibit, the expression of PTB; to practice the methods of this disclosure.

The terms "protein," "peptide," and "polypeptide" as used interchangeably can refer to an amino acid polymer or a set of two or more interacting or bound amino acid polymers.

The term "promoter," as used herein, can refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Promoters include constitutive and inducible promoters. A "constitutive" promoter is a promoter that can be active under most environmental and developmental conditions. An "inducible" promoter is a promoter that can be active under environmental or developmental regulation. The term "operably linked" can refer to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, the term "reprogramming" or "trans-differentiation" can refer to the generation of a cell of a certain lineage (e.g., a neuronal cell) from a different type of cell (e.g., a fibroblast cell) without an intermediate process of de-differentiating the cell into a cell exhibiting pluripotent stem cell characteristics. "Pluripotent" can refer to the ability of a cell to form all lineages of the body or soma (i.e., the embryo proper). Exemplary "pluripotent stem cells" can include embryonic stem cells and induced pluripotent stem cells.

The terms "subject" and "patient" as used interchangeably can refer to, except where indicated, mammals such as humans and non-human primates, as well as rabbits, rats, mice, goats, pigs, and other mammalian species. The term does not necessarily indicate that the subject has been diagnosed with a particular disease, but instead can refer to an individual under medical supervision. For example, mammalian species that benefit from the disclosed methods and composition include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo bison, horses, donkey, swine, sheep, and goats; exotic animals typically found in zoos such as bear, lions, tigers, panthers, elephants, hippopotamus, rhinoceros, giraffes antelopes, sloth, gazelles, zebras, wildebeests, prairie dogs, koala bears, kangaroo opossums, raccoons, pandas, hyena, seals, sea lions, elephant seals, otters, porpoises dolphins, and whales.

A "vector" is a nucleic acid that can be capable of transporting another nucleic acid into a cell. A vector can be capable of directing expression of a protein or proteins encoded by one or more genes, or a microRNA encoded by a polynucleotide, carried by the vector when it is present in the appropriate environment.

A "viral vector" is a viral-derived nucleic acid that can be capable of transporting another nucleic acid into a cell. A viral vector can be capable of directing expression of a protein or proteins encoded by one or more genes, or a microRNA encoded by a polynucleotide, carried by the vector when it is present in the appropriate environment. Examples of viral vectors include, but are not limited to, retroviral, adenoviral, lentiviral and adeno-associated viral vectors.

The disclosure provides composition and methods to convert or differentiate non-neuronal mammalian cells or astrocytes into functional neurons by knockdown of the Polypyrimidine Tract Binding protein (PTB). Some aspects of the disclosure provide methods of reprogramming a non-neuronal cell to a mature neuron. An exemplary method comprises: providing a non-neuronal cell, and contacting the non-neuronal cell with a composition comprising a cell-programming agent that suppresses expression or activity of PTB in the non-neuronal cell, thereby reprogramming the non-neuronal cell to a mature neuron. The methods and compositions not only convert cells in vitro but also directly in vivo in brain.

According to some embodiments of the disclosure, a single cell-programming agent that suppresses the expression or activity of PTB in a human non-neuronal cell can directly convert the non-neuronal cell into a mature neuron, when the human non-neuronal cell expresses miR-9 or Brn2 at a level that is higher than that expressed in a human adult fibroblast. In some embodiments of the disclosure, the direct conversion of a non-neuronal cell into a neuron by a single cell-programming agent can mean that the conversion of the non-neuronal cell into the neuron requires no other intervention than contacting with the single cell-programming agent.

An exemplary method comprises: providing a human non-neuronal cell that expresses miR-9 or Brn2 at a level that is higher than that expressed in a human adult fibroblast; and contacting the human non-neuronal cell with a composition comprising a cell-programming agent that suppresses expression or activity of PTB in the human non-neuronal cell, thereby reprogramming the human non-neuronal cell to a mature neuron.

According to some embodiments of the disclosure, human glial cell can express miR-9 or Brn2 at a level that is higher than that expressed in a human adult fibroblast. In another embodiment, the disclosure provides a method of reprogramming a human glial cell to a mature neuron. An exemplary method comprises: providing the human glial cell to be reprogrammed; and contacting the human glial cell with a composition comprising a cell-programming agent that suppresses the expression or activity of PTB in the human glial cell for at least 1 day, thereby reprogramming the human glial cell to a mature neuron.

In another embodiment, the disclosure provides a method of reprogramming an astrocyte to a mature neuron. An exemplary method comprises: providing the astrocyte to be reprogrammed; and contacting the astrocyte with a composition comprising a cell-programming agent that suppresses the expression or activity of PTB in the astrocyte for at least 1 day, thereby reprogramming the astrocyte to a mature neuron. In some embodiments, a single cell-programming agent that suppresses the expression or activity of PTB in an astrocyte can directly convert the astrocyte into a neuron.

According to the disclosure, in some cases, PTB reduction can induce a number of key neuronal differentiation factors. For example, without wishing to be bound to a certain theory, PTB and nPTB can be involved in two separate but intertwined loops, separately, that can be important in neuronal differentiation. As illustrated in FIG. 1, PTB can suppress a neuronal induction loop in which the microRNA miR-124 can inhibit the transcriptional repressor RE1-Silencing Transcription factor (REST), which in turn can block the induction of miR-124 and many neuronal-specific genes (loop I). During a normal neuronal differentiation process, PTB can be gradually down-regulated, and the PTB down-regulation can thus induce the expression of nPTB, which is part of a second loop for neuronal maturation that includes the transcription activator Brn2 and miR-9 (FIG. 1, loop II). As depicted in FIG. 1, in loop II, nPTB can inhibit Brn2 and consequentially can inhibit miR-9, and miR-9 in turn can inhibit nPTB.

According to some embodiments of the disclosure, the expression level of miR-9 or Brn2 in a non-neuronal cell can affect the conversion of the non-neuronal cell into a mature neuron by a cell-programming agent that suppresses the expression or activity of PTB in the non-neuronal cell. For example, a human adult fibroblast cell can have a low expression level of miR-9 and Brn2. In some embodiments, a single agent that suppresses the expression or activity of PTB in a human adult fibroblast cell can induce the human adult fibroblast cell to differentiate into a neuron-like cell, e.g., expression of Tuj1 protein, but not into a mature neuron, e.g., expression of NeuN protein or other markers of a mature neuron. Without wishing to be bound by a particular theory, the subject method and composition in some embodiments are particularly effective in creating a reinforcing feedback loop in molecular changes that direct the conversion of a non-neuronal cell into a neuron. Without wishing to be bound by a particular theory, when PTB expression or activity is initially downregulated by an exogenous anti-PTB agent, REST level can be downregulated, which can in turn lead to upregulation of miR-124 level. Without wishing to be bound by a particular theory, in some cases, as shown in FIG. 1, because miR-124 can target and inhibit the expression of PTB, the upregulated miR-124 can thus reinforce the inhibition of PTB in the cell; such a positive reinforcing effect can be long-lasting, even though in some cases, the anti-PTB agent, e.g., an antisense oligonucleotide against PTB, may be present and active merely temporarily in the cell.

According to some embodiments of the disclosure, a single cell-programming agent that suppresses the expression or activity of PTB in a human non-neuronal cell can directly convert the non-neuronal cell into a mature neuron, when the human non-neuronal cell expresses miR-9 or Brn2 at a level that is higher than that expressed in a human adult fibroblast. An exemplary human non-neuronal cell that can be used in the method provided herein expresses miR-9 or Brn2 at a level that is at least two times higher than that expressed in a human adult fibroblast. In some embodiments, the human non-neuronal cell expresses miR-9 or Brn2 at a level that is at least about 1.2 times, at least about 1.5 times, at least about 1.6 times, at least about 1.8 times, at least about 2 times, at least about 2.5 times, at least about 3 times, at least about 3.5 times, at least about 4 times, at least about 4.5 times, at least about 5 times, at least about 5.5 times, at least about 6 times, at least about 6.5 times, at least about 7 times, at least about 7.5 times, at least about 8 times, at least about 8.5 times, at least about 9 times, at least about 9.5 times, at least about 10 times, at least about 11 times, at least about 12 times, at least about 15 times, at least about 20 times, or at least about 50 times higher than that expressed in a human adult fibroblast. In some embodiments, the human non-neuronal cell expresses miR-9 or Brn2 at a level that is about 1.2 times, about 1.5 times, about 1.6 times, about 1.8 times, about 2 times, about 2.5 times, about 3 times, about 3.5 times, about 4 times, about 4.5 times, about 5 times, about 5.5 times, about 6 times, about 6.5 times, about 7 times, about 7.5 times, about 8 times, about 8.5 times, about 9 times, about 9.5 times, about 10 times, about 11 times, about 12 times, about 15 times, about 20 times, or about 50 times higher than that expressed in a human adult fibroblast.

In some embodiments, a single cell-programming agent that suppresses the expression or activity of PTB in a human non-neuronal cell can directly convert the non-neuronal cell into a mature neuron, when the human non-neuronal cell expresses both miR-9 and Brn2 at a level that is higher than that expressed in a human adult fibroblast. An exemplary human non-neuronal cell that can be used in the method as provided herein express both miR-9 and Brn2 at a level that is at least two times higher than that expressed in a human adult fibroblast. In some embodiments, the human non-neuronal cell expresses both miR-9 and Brn2 at a level that is at least about 1.2 times, at least about 1.5 times, at least about 1.6 times, at least about 1.8 times, at least about 2 times, at least about 2.5 times, at least about 3 times, at least about 3.5 times, at least about 4 times, at least about 4.5 times, at least about 5 times, at least about 5.5 times, at least about 6 times, at least about 6.5 times, at least about 7 times, at least about 7.5 times, at least about 8 times, at least about 8.5 times, at least about 9 times, at least about 9.5 times, at least about 10 times, at least about 11 times, at least about 12 times, at least about 15 times, at least about 20 times, or at least about 50 times higher than that expressed in a human adult fibroblast.

In some embodiments, a single cell-programming agent that suppresses the expression or activity of PTB in a human non-neuronal cell can directly convert the non-neuronal cell into a mature neuron, when the human non-neuronal cell expresses endogenous miR-9 or endogenous Brn2 at a level that is higher than that expressed in a human adult fibroblast. In some embodiments, no exogenous miR-9 is introduced into the human non-neuronal cell. In some embodiments, no exogenous Brn2 is introduced into the human non-neuronal cell.

In some embodiments, the expression level of miR-9 or Brn 2 in a non-neuronal cell can be assessed by any technique one skilled in the art would appreciate. For example, the expression level of miR-9 in a cell can be measured by reverse transcription (RT)-polymerase chain reaction (PCR), miRNA array, RNA sequencing (RNA-seq), and multiplex miRNA assays. Expression level of miR-9 can also be assayed by in situ methods like in situ hybridization. Expression level of Brn2 as a protein can be assayed by conventional techniques, like Western blot, enzyme-linked immunosorbent assay (ELISA), and immunostaining, or by other techniques, such as, but not limited to, protein microarray, and spectrometry methods (e.g., high-performance liquid chromatography (HPLC) and liquid chromatography-mass spectrometry (LC/MS)). In some embodiments, information on the expression level of miR-9 in a cell or a certain type of tissue/cells can be obtained by referring to publicly available databases for microRNAs, such as, but not limited to, Human MiRNA Expression Database (HMED), miRGator 3.0, miRmine, and PhenomiR. In some embodiments, information on the expression level of miR-9 in a cell or a certain type of tissue/cells can be obtained by referring to publicly available databases for protein expression, including, but not limited to, The Human Protein Atlas, GeMDBJ Proteomics, Human Proteinpedia, and Kahn Dynamic Proteomics Database.

According to certain embodiments of the disclosure, an exemplary method comprises providing a human non-neuronal cell to be reprogrammed; and contacting the human non-neuronal cell with a composition comprising a single cell-programming agent that yields a decrease in expression or activity of PTB in the human non-neuronal cell, and a decrease of expression or activity of nPTB after the expression or activity of PTB is decreased. In some embodiments, the cell-programming agent can lead to a sequential event as to the expression or activity levels of PTB and nPTB in a certain type of non-neuronal cell, e.g., human non-neuronal cell, e.g., human glial cell. In some embodiments, the direct effect of contacting with the cell-programming agent is a decrease of expression or activity of PTB in the non-neuronal cell. In some embodiments, in the non-neuronal cell, the decrease of expression or activity of PTB in the non-neuronal cell accompanies an initial increase of nPTB expression level in the non-neuronal cell. In some embodiments, an initial nPTB expression level increases to a high nPTB expression level as expression or activity of PTB is suppressed. In some embodiments, following the initial increase, nPTB expression decreases from the high nPTB expression level to a low nPTB expression level. In some embodiments, the low nPTB expression level is still higher than the initial nPTB expression level after expression or activity of PTB is suppressed. In some embodiments, the nPTB expression level decreases after the initial increase spontaneously without external intervention other than the cell-programming agent that suppresses the expression or activity of PTB. Without being bound to a certain theory, the subsequent decrease of nPTB expression level in the non-neuronal cell after PTB expression or activity is decreased by the cell-programming agent can be correlated with the direct conversion of the non-neuronal cell to a mature neuron by the cell-programming agent. According to some embodiments, a single cell-programming agent that suppresses the expression or activity of PTB does not induce the sequential event as described above in a human adult fibroblast cell, e.g., nPTB can experience the initial rise in expression level, but no subsequent decrease to a certain low level. In some embodiments, in a human astrocyte, a single cell-programming agent that suppresses the expression or activity of PTB in the human astrocyte leads to immediate decrease in expression or activity of PTB, an initial increase in expression level of nPTB, and a subsequent decrease in expression level of nPTB. In some embodiments, a single cell-programming agent that suppresses the expression or activity of PTB directly converts a human astrocyte to a mature neuron. In some embodiments, the expression level of miR-9 or Brn2 in the non-neuronal cell can be correlated with whether or not nPTB expression level in the non-neuronal decreases after the initial increases following PTB expression or activity is suppressed by a cell-programming agent. For instance, in human astrocyte, where miR-9 or Brn2 is expressed at a higher level than a human adult fibroblast, nPTB expression level in the non-neuronal decreases after the initial increases following PTB expression or activity is suppressed by a cell-programming agent, while in human adult fibroblast, as described above, in some cases, the subsequent decrease in nPTB expression level may not happen.

According to some embodiments of the disclosure, an exemplary non-neuronal cell that can be reprogrammed into a mature neuron in the method provided herein can include a glial cell, such as, but not limited, astrocyte, oligodendrocyte, ependymal cell, Schwan cell, NG2 cells, and satellite cell. In some embodiments, a glial cell can be a human glial cell, for instance, human astrocyte. In some embodiments, a glial cell can be a mouse glial cell. In some embodiments, a glial cell can be a glial cell from any other mammals, such as, but not limited to, non-human primate animals, pigs, dogs, donkeys, horses, rats, rabbits, and camels.

In some embodiments, a glial cell that can be used in the method as provided herein is a glial cell isolated from a brain. In some embodiments, a glial cell is a glial cell in a cell culture, for instance, divided from a parental glial cell. In some embodiments, a glial cell as provided herein is a glial cell differentiated from a different type of cell under external induction, for instance, differentiated in vitro from a neuronal stem cell in a culture medium containing differentiation factors, or differentiated from an induced pluripotent stem cell. In some other embodiments, a glial cell is a glial cell in a nervous system, for example, an astrocyte residing in a brain region.

In some embodiments, an astrocyte that can be used in the method as provided herein is a glial cell that is of a star-shape in brain or spinal cord. In some embodiments, an astrocyte expresses one or more of well-recognized astrocyte markers, including, but not limited to, glial fibrillary acidic protein (GFAP) and aldehyde dehydrogenase 1 family member L1 (ALDH1L1), excitatory amino acid transporter 1/glutamate aspartate transporter (EAAT1/GLAST), glutamine synthetase, S100 beta, or excitatory amino acid transporter 1/glutamate transporter 1 (EAAT2/GLT-1). In some embodiments, an astrocyte expresses glial fibrillary acidic protein (GFAP), Aldehyde Dehydrogenase 1 Family Member L1 (ALDH1L1), or both. In certain embodiments, an astrocyte is a non-neuronal cell in a nervous system that expresses a glial fibrillary acidic protein (GFAP) promoter-driven transgene (e.g., red fluorescent protein (RFP), Cre recombinase). In some embodiments, an astrocyte as described herein is not immunopositive for neuronal markers, e.g., Tuj1, NSE, NeuN, GAD67, VGluT1, or TH. In some embodiments, an astrocyte as described herein is not immunopositive for oligodendrocyte markers, e.g., Oligodendrocyte Transcription Factor 2, OLIG2. In some embodiments, an astrocyte as described herein is not immunopositive for microglia markers, e.g., transmembrane protein 119 (TMEM119), CD45, ionized calcium-binding adapter molecule 1 (Iba1), CD68, CD40, F4/80, or CD11 Antigen-Like Family Member B (CD11b). In some embodiments, an astrocyte as described herein is not immunopositive for NG2 cell markers (e.g., Neural/glial antigen 2, NG2). In some embodiments, an astrocyte as described herein is not immunopositive for neural progenitor markers, e.g., Nestin, CXCR4, Musashi, Notch-1, SRY-Box 1 (SOX1), SRY-Box 2 (SOX2), stage-specific embryonic antigen 1 (SSEA-1, also called CD15), or Vimentin. In some embodiments, an astrocyte as described herein is not immunopositive for pluripotency markers, e.g., NANOG, octamer-binding transcription factor 4 (Oct-4), SOX2, Kruppel Like Factor 4 (KLF4), SSEA-1, or stage-specific embryonic antigen 4 (SSEA-4). In some embodiments, an astrocyte as described herein is not immunopositive for fibroblast markers (e.g., Fibronectin).

Astrocytes can include different types or classifications. According the methods of the disclosure are applicable to different types of astrocytes. Non-limiting example of different types of astrocytes include type 1 astrocyte, which can be Ran2$^+$, GFAP$^+$, fibroblast growth factor receptor 3 positive (FGFR3$^+$), and A2B5$^-$. Type 1 astrocytes can arise from the tripotential glial restricted precursor cells (GRP). Type 1 astrocytes may not arise from the bipotential O2A/OPC (oligodendrocyte, type 2 astrocyte precursor) cells. Another non-limiting example includes type 2 astrocyte, which can be A2B5$^+$, GFAP$^+$, FGFR3$^-$, and Ran2$^-$. Type 2 astrocytes can develop in vitro from either tripotential GRP or from bipotential O2A cells or in vivo when these progenitor cells are transplanted into lesion sites. Astrocytes that can be used in the method provided herein can be further classified based their anatomic phenotypes, for instance, protoplasmic astrocytes that can be found in grey matter and have many branching processes whose end-feet envelop synapses; fibrous astrocyte that can be found in white matter and can have long thin unbranched processes whose end-feet envelop nodes of Ranvier. Astrocytes that can be used in the methods provided herein can also include GluT type and GluR type. GluT type astrocytes can express glutamate transporters (EAAT1/SLC1A3 and EAAT2/SLC1A2) and respond to synaptic release of glutamate by transporter currents, while GluR type astrocytes can express glutamate receptors (mostly mGluR and AMPA type) and respond to synaptic release of glutamate by channel-mediated currents and IP3-dependent Ca$^{2+}$ transients.

As provided herein, a cell-programming agent suppresses expression or activity of PTB by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the endogenous or native level. As provided herein, cell-programming agent suppresses expression or activity of PTB by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100% of the endogenous or native level. In some embodiments, a cell-programming agent as provided herein directly suppress the expression level of PTB, e.g., suppressing the transcription, translation, or protein stability of PTB. In some embodiments, a cell-programming agent as provided herein directly suppresses the activity of PTB, e.g., blocking the binding of PTB to its target molecules. In some embodiments, a cell-programming agent as provided herein directly effects on the expression or activity of PTB, without affecting other cellular signaling pathway. In some embodiments, a cell-programming agent as provided herein does not suppress the expression or activity of PTB through suppressing or upregulating the expression or activity level of another protein or microRNA, e.g., miR-124, miR-9, or Brn2.

As provided herein, a cell-programming agent that suppresses the expression or activity of PTB can be any type of reagent that suppresses or eliminates the protein expression or protein activity of PTB. In some embodiments, the cell-programming agent can be a small chemical molecule, interfering RNA, short hairpin RNA, microRNA, dominant negative PTB, sponge polynucleotide, ribozyme, antisense oligonucleotide, monoclonal antibody, or polyclonal antibody that is configured to suppress the expression or activity of PTB.

A small chemical molecule inhibitor of PTB can be an organic or inorganic chemical compound. As used herein, "small molecules" can refer to small organic or inorganic molecules of molecular weight below about 3,000 Daltons. The small molecules can be natural products or synthetic products. The small molecule inhibitor of PTB can have a structure that is based on an active fragment of PTB. For example, computer modeling methods known in the can be used to rationally design a molecule that has a structure similar to an active fragment of PTB, for example, the RNA-binding motifs (e.g., 1, 2, 3, 4, or more different RNA-binding motifs).

RNA interference can be useful for reducing expression level of target gene PTB. As provided herein, the methods can include use of RNA interference for suppressing expression of PTB in a non-neuronal cell. dsRNA molecules are believed to direct sequence-specific degradation of mRNA in cells of various types after first undergoing processing by an RNase E-like enzyme called DICER (Bernstein et al., Nature 409: 363, 2001) into smaller dsRNA molecules comprised of two 21 nt strands, each of which has a 5' phosphate group and a 3' hydroxyl, and includes a 19 nt region precisely complementary with the other strand, so that there is a 19 nt duplex region flanked by 2 nt-3' overhangs. RNAi can thus be mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides.

A short, interfering RNA (siRNA) that can be use in the methods provided herein can comprise an RNA duplex that can be approximately 19 basepairs long and optionally further comprise one or two single-stranded overhangs or loops, resulting in a total length of between approximately 21 and 23 nucleotides. A siRNA can comprise two RNA strands hybridized together, or can alternatively comprise a single RNA strand that includes a self-hybridizing portion. siRNAs can include one or more free strand ends, which can include phosphate and/or hydroxyl groups. siRNAs typically can include a portion that hybridizes under stringent conditions with a target transcript. One strand of the siRNA (or, the self-hybridizing portion of the siRNA) can be precisely complementary with a region of the target transcript (e.g., PTB mRNA transcript), meaning that the siRNA hybridizes to the target transcript without a single mismatch. In certain embodiments, perfect complementarity is not achieved. In some embodiments, the mismatches are located at or near the siRNA termini.

As used herein, siRNAs also include various RNA structures (e.g., short hairpin RNAs (shRNAs)) that can be processed in vivo to generate such molecules. shRNAs can include RNA strands containing two complementary elements that hybridize to one another to form a stem, a loop, and optionally an overhang, e.g., a 3' overhang. The stem can be approximately 19 bp long, the loop about 1-20, e.g., about 4-10, and about 6-8 nt long, and/or the overhang about 1-20, e.g., about 2-15 nt long. In certain embodiments, the stem can be minimally 19 nucleotides in length and can be up to approximately 29 nucleotides in length. Classical siRNAs as provided herein can trigger degradation of mRNAs to which they are targeted (e.g., PTB mRNA transcript), thereby also reducing the rate of protein synthesis. In some embodiments, certain siRNAs (e.g., microRNAs) that bind to the 3' UTR of PTB mRNA transcript can inhibit expression of a protein encoded by the template transcript by a mechanism related to but distinct from classic RNA interference, e.g., by reducing translation of the transcript rather than decreasing its stability. MicroRNAs can be between approximately 20 and 26 nucleotides in length, e.g., 22 nt in length. MicroRNAs can be used to destabilize target transcripts and/or block their translation (e.g., PTB expression).

A plasmid containing a DNA sequence encoding for a particular desired siRNA sequence is delivered into a target cell via transfection or virally-mediated infection. Once in the cell, the DNA sequence is continuously transcribed into RNA molecules that loop back on themselves and form hairpin structures through intramolecular base pairing. These hairpin structures, once processed by the cell, are equivalent to transfected siRNA molecules and are used by the cell to mediate RNAi of the desired protein. The use of shRNA has an advantage over siRNA transfection as the former can lead to stable, long-term inhibition of protein expression. Inhibition of protein expression by transfected siRNAs is a transient phenomenon that does not occur for times periods longer than several days. In some cases, this can be preferable and desired. In cases where longer periods of protein inhibition are necessary, shRNA-mediated inhibition is preferable. Short Hairpin RNAs (shRNA) can be comprised of stem-loop structures, which can be designed to contain a 5' flanking region, siRNA region segments, a loop region, a 3' siRNA region and a 3' flanking region. shRNAs can have effective knockdown of target sequences.

Sponge polynucleotides that have a base sequence complementary to part or all of target RNA transcript (e.g., PTB mRNA transcript) can be used in the method provided herein as well. For instance, sponge polynucleotide can contain polypyrimidine tract. Sponge polynucleotides can be used to "trap" PTB mRNA transcripts, thereby blocking them from being normally spliced, translated, or transported, so that the expression level of PTB protein can be reduced.

In some embodiments, the cell-programming agent can be a dominant-negative mutant that can inhibit an activity of PTB molecule. The dominant negative mutant can be a peptide or peptide mimetic that can inhibit an activity of PTB molecule, or a nucleic acid composition, in the form of a DNA vector or gene therapy vector, that expresses a dominant-negative polypeptide that can inhibit an activity of PTB. The dominant negative mutant can bind to a target RNA or ligand of PTB, affecting its target interaction. The dominant negative molecule can act, for example, by blocking protein-protein interactions or protein-RNA interactions.

Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, e.g., to induce or stabilize a secondary structure, e.g., a beta turn, gamma turn, beta sheet, alpha helix conformation, and the like. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester.

Another non-limiting example of cell-programming agent can be anti-PTB antibody. An anti-PTB antibody can be a polyclonal antibody or a monoclonal antibody that specifically binds to PTB. An anti-PTB antibody as used herein can bind to PTB at its active fragment or inactive fragment. In some configurations, an anti-PTB antibody that binds to the active fragment of PTB can block PTB from interacting with its functional targets (e.g., target RNA transcript) or partners (e.g., protein ligands), thereby inhibiting activity of PTB. In other configurations, an anti-PTB antibody that binds to the inactive fragment of PTB can induce PTB aggregation in some cases, thereby immobilizing PTB inside the cell, preventing it from relocating to interact with its targets or partners. In some cases, an anti-PTB antibody can also induce protein degradation of PTB as being bound to an antibody.

Antisense nucleic acids (e.g., DNA, RNA, modified DNA, or modified RNA) are generally single-stranded nucleic acids complementary to a portion of a target nucleic acid (e.g., a PTB mRNA transcript) and therefore able to bind to the target to form a duplex. An anti-PTB antisense nucleotide can be configured to suppress the expression or activity of PTB, e.g., in a cell. Antisense oligonucleotides (ASOs) can pair with a target mRNA to render the RNA a substrate for cleavage by the intranuclear enzyme RNase H. In some embodiments, antisense oligonucleotide can mediate target mRNA degradation for ~3 months in the nervous system, e.g., the rodent and non-human primate nervous system after injection into the cerebral spinal fluid. As provided herein, antisense oligonucleotide that can be used in the methods provided herein are typically oligonucleotides that range from 15 to 35 nucleotides in length but can range from 10 up to approximately 50 nucleotides in length. Binding can reduce or inhibit the function of the target PTB nucleic acid. For example, antisense oligonucleotides can block transcription when bound to genomic DNA (e.g., PTB gene), inhibit translation when bound to mRNA (e.g., PTB mRNA transcript), and/or lead to degradation of the nucleic acid. Reduction in expression of PTB can be achieved by the administration of antisense nucleic acids or peptide nucleic acids comprising sequences complementary to those of the mRNA that encodes the polypeptide. Antisense technology and its applications are well known in the art and are described in (Phillips, M. I. (ed.) Antisense Technology, Methods Enzymol., 313 and 314: 2000, and references mentioned therein. See also Crooke, S. "ANTISENSE DRUG TECHNOLOGY: PRINCIPLES, STRATEGIES, AND APPLICATIONS" (1st Edition) Marcel Dekker; and references cited therein.

In some embodiments, antisense oligonucleotide as provided herein can comprise locked nucleic acids (LNAs). In some embodiments, LNAs refer to a modified RNA nucleotide, in which the ribose moiety is modified with an extra bridge connecting the 2' oxygen and 4' carbon and the bridge "locks" the ribose in the 3'-endo (North) conformation. In some embodiments, LNAs are be mixed with DNA or RNA residues in the oligonucleotide whenever desired and hybridize with DNA or RNA according to Watson-Crick base-pairing rules. The locked ribose conformation can enhance base stacking and backbone pre-organization. Inclusion of LNAs in the oligonucleotide as provide herein, in some embodiments, increases the hybridization properties (melting temperature) of oligonucleotides. In some cases, inclusion of LNAs blocks translation of the target mRNA, but without inducing degradation of the target mRNA. Exemplary techniques and applications of using LNAs can be found in PCT/US2013/047157 and Campbell M A et al., *Chem. Soc. Rev.,* 40(12), 5680-9, which are incorporated herein by reference in their entireties.

Cell-programming agent as provided herein can also include ribozymes or deoxyribozymes that can catalyze the sequence-specific cleavage of RNA molecules. The cleavage site is determined by complementary pairing of nucleotides in the RNA or DNA enzyme with nucleotides in the target RNA (e.g., PTB mRNA transcript). Thus, RNA and DNA enzymes can be designed to cleave PTB mRNA transcript, thereby increasing its rate of degradation.

As provided herein, contacting the non-neuronal cell with a cell-programming agent can be performed in any appropriate manner, depending on the type of non-neuronal cell to be reprogrammed, the environment in which the non-neuronal cell resides, the type of cell-programming agent, and the desired cell reprogramming outcome. In some embodiments, cell-programming agent, such as small molecule inhibitor of PTB or antisense oligonucleotide, is applied to the non-neuronal cell directly, given that the cell-programming agent exhibits cell membrane penetration ability itself. In some embodiments, cell-programming agent, such as shRNA, antibody, or dominant negative mutant, is introduced in the form of nucleic acid vectors that express the desired cell-programming agent. In these configurations, non-viral transfection methods or viral transduction methods are utilized to introduce the cell-programming agent. Non-viral transfection can refer to all cell transfection methods that are not mediated through a virus. Non-limiting examples of non-viral transfection include electroporation, microinjection, calcium phosphate precipitation, transfection with cationic polymers, such as DEAE-dextran followed by polyethylene glycol, transfection with dendrimers, liposome mediated transfection ("lipofection"), microprojectile bombardment ("gene gun"), fugene, direct sonic loading, cell squeezing, optical transfection, protoplast fusion, impalefection, magnetofection, nucleofection, and any combination thereof. In some embodiments, the methods provided herein utilize viral vectors as appropriate medium for delivering the cell-programming agent to the non-neuronal cell. Examples of appropriate viral vectors can include adenoviral, lentiviral, adeno-associated viral (AAV), poliovirus, herpes simplex virus (HSV), or murine Maloney-based viral vectors. In some embodiments, the vector is an AAV vector. As provided herein, viral vector methods can include the use of either DNA or RNA viral vectors. In some embodiments, a cell-programming agent is administered in the form of AAV vector. In some embodiments, a cell-programming agent is administered in the form of lentiviral vector. For example, a cell-programming agent can be delivered to a non-neuronal cell using a lentivirus or adenovirus associated virus (AAV) to express shRNA against PTB.

According to some embodiments of the disclosure, methods provided herein comprise suppressing the expression or activity of PTB in a non-neuronal cell via a cell-programming agent of a sufficient amount for reprogramming the non-neuronal cell to a mature neuron. The sufficient amount of cell-programming agent can be determined empirically as one skilled in the art would readily appreciate. In some embodiments, the amount of cell-programming agent can be determined by any type of assay that examines the activity of the cell-programming agent in the non-neuronal cell. For example, when the cell-programming agent is configured to suppress the expression of PTB in the non-neuronal cell, the sufficient amount of the cell-programming agent can be determined by assessing the expression level of PTB in an exemplary non-neuronal cell after administration of the agent, e.g., by Western blot. In some embodiments, functional assays are utilized for assessing the activity of PTB after delivery of the cell-programming agent to an exemplary non-neuronal cell. In some embodiments, other functional assays, such as, immunostaining for neuronal markers, electrical recording for neuronal functional properties, that examine downstream neuronal properties are used to determine a sufficient amount of cell-programming agent. In some embodiments, the cell-programming agent is delivered in the form of a viral vector. A viral vector can comprises one or more copies of expression sequence coding for a cell-programming agent, e.g., shRNA, microRNA, dominant negative mutant, or antibody, such as, 1, 2, 3, 4, 5, 6, 7, 8, 9, 10, 20, 30, 50, or 100 copies. A viral vector can be tittered to any appropriate amount for administration, as one skilled in the art will be able to determine. For example, the titer as determined by PCR, RT-PCR, or other methods can be at least about $10^5$ viral particles/mL, at least about $10^6$ particles/mL, at least about $10^7$ particles/mL, at least about $10^8$ particles/mL, at least about $10^9$ particles/mL, at least about $10^{10}$ particles/mL, at least about $10^{11}$ particles/mL, at least about $10^{12}$ particles/mL, at least about $10^{13}$ particles/mL, at least about $10^{14}$ particles/mL, or at least about $10^{15}$ particles/mL. In some embodiments, the titer of viral vector to be administered is at least about $10^{10}$ viral particles/mL. In some embodiments, the cell-programming agent is antisense oligonucleotide, and the antisense oligonucleotide can be delivered at any effective amount as one skilled in the art will appreciate. In some embodiments, the antisense oligonucleotide is administered at least about 0.05 µg, at least about 0.075 µg, at least about 0.1 µg, at least about 0.125 µg, at least about 0.15 µg, at least about 0.175 µg, at least about 0.2 µg, at least about 0.225 µg, at least about 0.25 µg, at least about 0.275 µg, at least about 0.3 µg, at least about 0.325 µg, at least about 0.35 µg, at least about 0.375 µg, at least about 0.4 µg, at least about 0.425 µg, at least about 0.045 µg, at least about 0.475 µg, at least about 0.5 µg, at least about 0.6 µg, at least about 0.7 µg, at least about 0.8 µg, at least about 0.9 µg, at least about 1.0 µg, at least about 1.2 µg, at least about 1.25 µg, at least about 1.3 µg, at least about 1.4 µg, at least about 1.5 µg, at least about 1.6 µg, at least about 1.7 µg, at least about 1.8 µg, at least about 1.9 µg, at least about 2.0 µg, at least about 2.1 µg, at least about 2.2 µg, at least about 2.3 µg, at least about 2.4 µg, at least about 2.5 µg, at least about 2.75 µg, at least about 3 µg, at least about 4 µg, at least about 5 µg, at least about 6 µg, at least about 7 µg, at least about 8 µg, at least about 9 µg, or at least about 10 µg. In some embodiments, the antisense oligonucleotide is administered about 0.05 µg, about 0.075 µg, about 0.1 µg, about 0.125 µg, about 0.15 µg, about 0.175 µg, about 0.2 µg, about 0.225 µg, about 0.25 µg, about 0.275 µg, about 0.3 µg, about 0.325 µg, about 0.35 µg, about 0.375 µg, about 0.4 µg, about 0.425 µg, about 0.045 µg, about 0.475 µg, about 0.5 µg, about 0.6 µg, about 0.7 µg, about 0.8 µg, about 0.9 µg, about 1.0 µg, about 1.2 µg, about 1.25 µg, about 1.3 µg, about 1.4 µg, about 1.5 µg, about 1.6 µg, about 1.7 µg, about 1.8 µg, about 1.9 µg, about 2.0 µg, about 2.1 µg, about 2.2 µg, about 2.3 µg, about 2.4 µg, about 2.5 µg, about 2.75 µg, about 3 µg, about 4 µg, about 5 µg, about 6 µg, about 7 µg, about 8 µg, about 9 µg, or about 10 µg. In some cases, the antisense oligonucleotide is administered in vitro at about 0.075 to about 0.325 µg, about 0.1 to about 0.3 µg, or about 0.125 to about 0.25 µg. In some cases, the antisense oligonucleotide is administered in vivo at about 1 to about 10 µg, at about 1 to about 5 μg, at about 1 to about 3 μg, about 1.5 to about 2.5 μg, or about 1.75 to about 2.25 μg.

Methods provided herein can comprise suppressing the expression or activity of PTB in a non-neuronal cell for a certain period of time sufficient for reprogramming the non-neuronal cell to a mature neuron. In some embodiments, exemplary methods comprise contacting the non-neuronal cell with a cell-programming agent that suppresses the expression or activity of PTB in the non-neuronal cell for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 3 weeks, at least 4 weeks, at least 5 weeks, at least 2 months, at least 3 months, at least 4 months, or at least 5 months, thereby reprogramming the non-neuronal cell to a mature neuron. In some embodiments, exemplary methods comprise contacting the non-neuronal cell with a cell-programming agent that suppresses the expression or activity of PTB in the non-neuronal cell for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 3 weeks, about 4 weeks, about 5 weeks, about 2 months, about 3 months, about 4 months, or about 5 months, thereby reprogramming the non-neuronal cell to a mature neuron. In some embodiments, exemplary methods comprise contacting the non-neuronal cell with a cell-programming agent that suppresses the expression or activity of PTB in the non-neuronal cell for at most 2 days, at most 3 days, at most 4 days, at most 5 days, at most 6 days, at most 7 days, at most 8 days, at most 9 days, at most 10 days, at most 11 days, at most 12 days, at most 13 days, at most 14 days, at most 15 days, at most 3 weeks, at most 4 weeks, at most 5 weeks, at most 2 months, at most 3 months, at most 4 months, or at most 5 months, thereby reprogramming the non-neuronal cell to a mature neuron. In some configurations, the methods provided herein comprise administering the cell-programming agent for only once, e.g., adding the cell-programming agent to a cell culture comprising the non-neuronal cell, or delivering the cell-programming agent to a brain region comprising the non-neuronal cell, for only once, and the cell-programming agent can remain active as suppressing expression or activity of PTB in the non-neuronal cell for a desirable amount of time, e.g., for at least 1 day, at least 2 days, at least 4 days, or at last 10 days. For instance, when the cell-programming agent comprises an AAV vector expressing an anti-PTB shRNA, the design of the AAV vector can enable it to remain transcriptionally active for an extended period of time. In some embodiments, the methods provided herein comprise administering the cell-programming agent for more than once, e.g., for at least 2 times, at least 3 times, at least 4 times, at least 5 times, at least 6 times, at least 7 times, at least 8 times, at least 9 times, at least 10 times, at least 12 times, at least 15 times, at least 20 times or more.

As provided herein, a method can comprise reprogramming a non-neuronal cell to a neuron in vitro under appropriate culture conditions. One of ordinary skills in the art will appreciate that appropriate cell culture conditions can be chosen for promoting neuronal growth. In some embodiments, various factors can be provided in the culture medium for maintaining the survival of the non-neuronal cells, the cells undergoing reprogramming, and the reprogrammed neurons. Any known culture medium capable of supporting cell growth can be used and optimized for desirable outcomes. Culture medium can include HEM, DMEM, RPMI, F-12, or the like. Culture medium can contain supplements which can be important for cellular metabolism such as glutamine or other amino acids, vitamins, minerals or useful proteins such as transferrin and the like. Medium can also contain antibiotics to prevent contamination with yeast, bacteria and fungi such as penicillin, streptomycin, gentamicin and the like. In some cases, the medium can contain serum derived from bovine, equine, chicken and the like. An exemplary culture medium for astrocyte as a starting cell can include DMEM/F12, FBS, penicillin/streptomycin, B27, epidermal growth factor (EGF), and fibroblast growth factor 2 (FGF2). In some cases, a neuron differentiation medium is used during the reprogramming and/or maintaining the reprogramed neurons. In some cases, a neuron differentiation medium comprises an inhibitor of ALK5 (TGFβ type I receptor kinase), such as SB431542, A-77-01, ALK5 inhibitor II, RepSox, SB525334, GW788388, SD-208, LY215729, or LY364947. In some cases, a neuron differentiation medium comprises an inhibitor of GSK3b (glycogen synthase kinase 3 beta), such as CHIR99021, IM-12, TWS119, BIO, 3F8, AR-A014418, AT9283, or 2-Thio(3-iodobenzyl)-5-(1-pyridyl)-[1,3,4]-oxadiazole. In some cases, a neuron differentiation medium comprises an activator of PKA (protein kinase A), such as dibutyryl-cAMP (cyclic adenosine monophosphate), 8-bromo-cAMP, 8-CPT-cAMP, taxol, belinostat, or Sp-cAMPs. An exemplary neuronal differentiation medium includes a N3/basal medium, containing DMEM/F12, Neurobasal, insulin, transferring, sodium lenite, progesterone, putrescine, supplemented with B27, FBS, ChIR99021, SB431542 and Db-cAMP, and/or neurotrophic factors like BDNF, GDNF, NT3 and CNTF.

According to some embodiments of the present disclosure, the methods provided herein comprise reprogramming a plurality of non-neuronal cells into mature neurons at a high efficiency.

In some embodiments, the methods comprise reprogramming mouse astrocytes into mature neurons, and at least 60% of the mouse astrocytes are converted to mature neurons that are Tuj1 positive. In some embodiments, at least 40% of the mouse astrocytes are converted to mature neurons that are Map2 positive. In some embodiments, at least about 20%, at least about 25%, at least about 30%, at least about 35%, at least about 38%, at least about 40%, at least about 42%, at least about 44%, at least about 46%, at least about 48%, at least about 50%, at least about 52%, at least about 54%, at least about 56%, at least about 58%, at least about 60%, at least about 62%, at least about 64%, at least about 66%, at least about 68%, at least about 70%, at least about 72%, at least about 74%, at least about 76%, at least about 78%, at least about 80%, at least about 82%, at least about 84%, at least about 86%, at least about 88%, at least about 90%, at least about 92%, at least about 94%, at least about 96%, at least about 98%, at least about 99%, or 100% of the mouse astrocytes are converted to mature neurons that are positive for Tuj1 or Map2.

In some embodiments, the methods comprise reprogramming human astrocytes into mature neurons, and at least 40%, at least 60%, or at least 80% of the human astrocytes are converted to mature neurons that are Tuj1 positive. In some embodiments, at least 20%, at least 40% or at least 60% of the human astrocytes are converted to mature neurons that are Map2 positive. In some embodiments, at least about 20%, at least about 25%, at least about 30%, at least about 35%, at least about 38%, at least about 40%, at least about 42%, at least about 44%, at least about 46%, at least about 48%, at least about 50%, at least about 52%, at least about 54%, at least about 56%, at least about 58%, at least about 60%, at least about 62%, at least about 64%, at least about 66%, at least about 68%, at least about 70%, at least about 72%, at least about 74%, at least about 76%, at least about 78%, at least about 80%, at least about 82%, at least about 84%, at least about 86%, at least about 88%, at least about 90%, at least about 92%, at least about 94%, at least about 96%, at least about 98%, at least about 99%, or about 100% of the human astrocytes are converted to mature neurons that are positive for Tuj1 or Map2.

In some embodiments, the methods as provided herein comprise reprogramming a plurality of non-neuronal cells, e.g., human non-neuronal cells, e.g., human glial cells, or astrocytes, and at least about 20%, at least about 25%, at least about 30%, at least about 35%, at least about 38%, at least about 40%, at least about 42%, at least about 44%, at least about 46%, at least about 48%, at least about 50%, at least about 52%, at least about 54%, at least about 56%, at least about 58%, at least about 60%, at least about 62%, at least about 64%, at least about 66%, at least about 68%, at least about 70%, at least about 72%, at least about 74%, at least about 76%, at least about 78%, at least about 80%, at least about 82%, at least about 84%, at least about 86%, at least about 88%, at least about 90%, at least about 92%, at least about 94%, at least about 96%, at least about 98%, or at least about 99% of the non-neuronal cells, e.g., human non-neuronal cells, e.g., human glial cells, or astrocytes are reprogrammed to mature neurons. In some embodiments, the methods as provided herein reprogram about 20%, about 25%, about 30%, about 35%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, about 98%, about 99%, or about 100% of the non-neuronal cells, e.g., human non-neuronal cells, e.g., human glial cells, or astrocytes are reprogrammed to mature neurons.

In some embodiments, a mature neuron is characterized by its expression of one or more neuronal markers selected from the group consisting of NeuN (neuronal nuclei antigen), Map2 (microtubule-associated protein 2), NSE (neuron specific enolase), 160 kDa neurofilament medium, 200 kDa neurofilament heavy, PDS-95 (postsynaptic density protein 95), Synapsin I, Synaptophysin, GAD67 (glutamate decarboxylase 67), GAD65 (glutamate decarboxylase 67), parvalbumin, DARPP32 (dopamine- and cAMP-regulated neuronal phosphoprotein 32), vGLUT1 (vesicular glutamate transporter 1), vGLUT2 (vesicular glutamate transporter 1), acetylcholine, vesicular GABA transporter (VGAT), and gamma-aminobutyric acid (GABA), and TH (tyrosine hydroxylase). In some embodiments, at least 40% of the non-neuronal cells, e.g., human non-neuronal cells, e.g., human glial cells, or astrocytes are reprogrammed to mature neurons.

As one of ordinary skills in the art would readily appreciate, the expression of all those markers above can be assessed by any common techniques. For examples, immunostaining using antibodies against specific cell type markers as described herein can reveal whether or not the cell of interest expresses the corresponding cell type marker. Immunostaining under certain conditions can also uncover the subcellular distribution of the cell type marker, which can also be important for determining the developmental stage of the cell of interest. For instance, expression of Map2 can be found in various neurites (e.g., dendrites) in a postmitotic mature neuron, but absent in axon of the neuron. Expression of voltage-gated sodium channels (e.g., a subunits Nav1.1-1.9) and β subunits) can be another example, they can be clustered in a mature neuron at axon initial segment, where action potential can be initiated, and Node of Ranvier. In some embodiments, other techniques, such as, but not limited to, flow cytometry, mass spectrometry, in situ hybridization, RT-PCR, and microarray, can also be used for assessing expression of specific cell type markers as described herein.

Certain aspects of the present disclosure provide methods that comprise reprogramming a plurality of non-neuronal cells, and at least about 20%, at least about 25%, at least about 30%, at least about 35%, at least about 38%, at least about 40%, at least about 42%, at least about 44%, at least about 46%, at least about 48%, at least about 50%, at least about 52%, at least about 54%, at least about 56%, at least about 58%, at least about 60%, at least about 62%, at least about 64%, at least about 66%, at least about 68%, at least about 70%, at least about 72%, at least about 74%, at least about 76%, at least about 78%, at least about 80%, at least about 82%, at least about 84%, at least about 86%, at least about 88%, at least about 90%, at least about 92%, at least about 94%, at least about 96%, at least about 98%, or at least about 99% of the non-neuronal cells, e.g., human non-neuronal cells, e.g., human glial cells, or astrocytes are reprogrammed to functional neurons. In some embodiments, the methods provided herein reprogram at least 20% of the non-neuronal cells, e.g., human non-neuronal cells, e.g., human glial cells, or astrocytes are reprogrammed to functional neurons. In some embodiments, the methods provided herein reprogram about 20%, about 25%, about 30%, about 35%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, about 98%, about 99%, or about 100% of the non-neuronal cells, e.g., human non-neuronal cells, e.g., human glial cells, or astrocytes are reprogrammed to functional neurons.

In some embodiments, functional neurons are characterized in their ability to form neuronal network, to send and receive neuronal signals, or both. In some embodiments, functional neurons fire action potential. In some embodiments, functional neurons establish synaptic connections with other neurons. For instance, a functional neuron can be a postsynaptic neuron in a synapse, e.g., having its dendritic termini, e.g., dendritic spines, forming postsynaptic compartments in synapses with another neuron. For instance, a functional neuron can be a presynaptic neuron in a synapse, e.g., having axonal terminal forming presynaptic terminal in synapses with another neuron. Synapses a functional neuron can form with another neuron can include, but not limited to, axoaxonic, axodendritic, and axosomatic. Synapses a functional neuron can form with another neuron can be excitatory (e.g., glutamatergic), inhibitory (e.g., GABAergic), modulatory, or any combination thereof. In some embodiments, synapses a functional neuron forms with another neuron is glutamatergic, GABAergic, cholinergic, adrenergic, dopaminergic, or any other appropriate type. As a presynaptic neuron, a function neuron can release neurotransmitter such as, but not limited to, glutamate, GABA, acetylcholine, aspartate, D-serine, glycine, nitric oxide (NO), carbon monoxide (CO), hydrogen sulfide ($H_2S$), dopamine, norepinephrine (also known as noradrenaline), epinephrine (adrenaline), histamine, serotonin, phenethylamine, N-methylphenethylamine, tyramine, 3-iodothyronamine, octopamine, tryptamine, somatostatin, substance P, opioid peptides, adenosine triphosphate (ATP), adenosine, and anandamide. As a postsynaptic neuron, a functional neuron can elicit postsynaptic response to a neurotransmitter released by a presynaptic neuron into the synaptic cleft. The postsynaptic response a functional neuron as generated in the method provided herein can be either excitatory, inhibitory, or any combination thereof, depending on the type of neurotransmitter receptor the functional neuron expresses. In some embodiments, the functional neuron expresses ionic neurotransmitter receptors, e.g., ionic glutamate receptors and ionic GABA receptors. Ionic glutamate receptors can include, but not limited to, α-amino-3-hydroxy-5-methyl-4-isoxazolepropionic acid (AMPA)-type glutamate receptors (e.g., GluA1/GRIA1; GluA2/GRIA2; GluA3/GRIA3; GluA4/GRIA4), delta receptors (e.g., GluD1/GRID1; GluD2/GRID2), kainate receptors (e.g., GluK1/GRIK1; GluK2/GRIK2; GluK3/GRIK3; GluK4/GRIK4; GluK5/GRIK5) and N-methyl-D-aspartate (NMDA) receptors (e.g., GluN1/GRIN1; GluN2A/GRIN2A; GluN2B/GRIN2B; GluN2C/GRIN2C; GluN2D/GRIN2D; GluN3A/GRIN3A; GluN3B/GRIN3B). Ionic GABA receptors can include, but not limited to, $GABA_A$ receptor. In some embodiments, the functional neuron expresses metabolic neurotransmitter receptors, e.g., metabolic glutamate receptors (e.g., $mGluR_1$, $mGluR_5$, $mGluR_2$, $mGluR_3$, $mGluR_4$, $mGluR_6$, $mGluR_7$, $mGluR_8$), and metabolic GABA receptors (e.g., $GABA_B$ receptor). In some embodiments, the functional neuron expresses a type of dopamine receptor, either D1-like family dopamine receptor, e.g., D1 and D5 receptor (D1R and D5R), or D2-like family dopamine receptor, e.g., D2, D3, and D4 receptors (D2R, D3R, and D4R). In some embodiments, a functional neuron as provided herein forms electrical synapse with another neuron (e.g., gap junction). In some embodiments, a function neuron as provided herein forms either chemical or electrical synapse(s) with itself, as known as autapse.

The characteristics of a function neuron can be assessed by common techniques available to one skilled in the art. For example, the electrical properties of a functional neuron, such as, firing of action potential and postsynaptic response to neurotransmitter release can be examined by techniques such as patch clamp recording (e.g., current clamp and voltage clamp recordings), intracellular recording, and extracellular recordings (e.g., tetrode recording, single-wire recording, and filed potential recording). Specific properties of a functional neuron (e.g., expression of ion channels and resting membrane potential) can also be examined by patch clamp recording, where different variants of patch clamp recording can be applied for different purposes, such as cell-attached patch, inside-out patch, outside-out patch, whole-cell recording, perforated patch, loose patch. Assessment of postsynaptic response by electrical methods can be coupled with either electrical stimulation of presynaptic neurons, application of neurotransmitters or receptor agonists or antagonists. In some cases, AMPA-type glutamate receptor-mediated postsynaptic current can be assessed by AMPA receptor agonists, e.g., AMPA, or antagonists, e.g., 2,3-dihydroxy-6-nitro-7-sulfamoyl-benzoquinoxaline (NBQX) or 6-cyano-7-nitroquinoxaline-2,3-dione (CNQX). In some cases, NMDA-type glutamate receptor-mediated postsynaptic current can be assessed by NMDA receptor agonists, e.g., NMDA and glycine, or antagonists, e.g., AP5 and ketamine. In some embodiments, functional neurons are examined by techniques other than electrical approaches. For example, recent development of various fluorescent dyes or genetically encoded fluorescent proteins and imaging techniques can be utilized for monitoring electrical signals conveyed or transmitted by a functional neuron. In this context, calcium-dependent fluorescent dyes (e.g., calcium indicators), such as, but not limited to, fura-2, Indo-1, fluo-3, fluo-4, and Calcium Green-1, and calcium-dependent fluorescent proteins, such as, but not limited to, Cameleons, FIP-CBSM, Pericams, GCaMP, TN-L15, TN-humTnC, TN-XL, TN-XXL, and Twitch's, can be used to trace calcium influx and efflux as an indicator of neuronal membrane potential. Alternatively or additionally, voltage-sensitive dyes that can change their spectral properties in response to voltage changes can also be used for monitoring neuronal activities.

Neurotransmitter release can be an important aspect of a functional neuron. The methods provided herein can comprise reprogram a non-neuronal cell to a functional neuron that releases a certain type of neurotransmitter. In some embodiments, the functional neuron releases neurotransmitter such as, but not limited to, glutamate, GABA, acetylcholine, aspartate, D-serine, glycine, nitric oxide (NO), carbon monoxide (CO), hydrogen sulfide ($H_2S$), dopamine, norepinephrine (also known as noradrenaline), epinephrine (adrenaline), histamine, serotonin, phenethylamine, N-methylphenethylamine, tyramine, 3-iodothyronamine, octopamine, tryptamine, somatostatin, substance P, opioid peptides, adenosine triphosphate (ATP), adenosine, and anandamide. In some embodiments, the functional neuron releases dopamine as a major neurotransmitter. In some embodiments, the functional neuron releases more than one type of neurotransmitter. In some embodiments, the functional neuron releases neurotransmitter in response to an action potential. In some embodiments, the functional neuron releases neurotransmitter in response to graded electrical potential (e.g., membrane potential changes that do not exceed a threshold for eliciting an action potential). In some embodiments, the functional neuron exhibits neurotransmitter release at a basal level (e.g., spontaneous neurotransmitter release). Neurotransmitter release as described herein from a functional neuron can be assessed by various techniques that are available to one of ordinary skills in the art. In some embodiments, imaging approaches can be used for characterizing a functional neuron's neurotransmitter release, for instance, by imaging a genetically encoded fluorescent fusion molecule comprising a vesicular protein, one can monitor the process of synaptic vesicles being fused to presynaptic membrane.

Alternatively or additionally, other methods can be applied to directly monitor the level of a specific neurotransmitter. For example, HPLC probe can be used to measure the amount of dopamine in a culture dish or a brain region where a functional neuron projects its axon to. The level of dopamine as detected by HPLC can indicate the presynaptic activity of a functional neuron. In some embodiments, such assessment can be coupled with stimulation of the functional neuron, in order to change its membrane potential, e.g., to make it elicit action potential.

In an aspect, the present disclosure provides a method of generating a functional neuron in vivo. An exemplary method comprises administering to a region in the nervous system, e.g., brain or spinal cord, of a subject a composition comprising a cell-programming agent in a non-neuronal cell in the region in nervous system, e.g., brain or spinal cord, and allowing the non-neuronal cell to reprogram into the functional neuron. In some embodiments, the cell-programming agent suppresses the expression or activity of PTB. In some embodiments, the cell-programming agent does not comprise NeuroD1 protein, or an expression construct coding for NeuroD1.

According to some embodiments of the present disclosure, the methods provided herein comprise direct administration of a cell-programming agent into a region in the nervous system, e.g., brain or spinal cord, of a subject. In some embodiments, the cell-programming agent is delivered locally to a region in the nervous system. In one embodiment, a composition comprising a cell-programming agent, such as, but not limited to, a viral vector, an antisense oligonucleotide, a small molecule inhibitor, or an expression cassette is administered to the subject or organism by stereotaxic or convection enhanced delivery to a brain region. Using stereotaxic positioning system, one skilled in the art would be able to locate a specific brain region that is to be administered with the composition comprising the cell-programming agent. Such methods and devices can be readily used for the delivery of the composition as provided herein to a subject or organism. In another embodiment, a composition as provided herein is delivered systemically to a subject or to a region in nervous system, e.g., brain or spinal cord, of a subject, e.g., delivered to cerebrospinal fluid or cerebral ventricles, and the composition comprises one or more agents that are configured to relocate the cell-programming agent to a particular region in the nervous system or a particular type of cells in the nervous system of the subject.

In some embodiments, the cell-programming agent used in the methods provided herein comprises a virus that expresses an anti-PTB shRNA, anti-PTB microRNA, dominant negative PTB mutant, or a sponge polyribonucleotide containing polypyrimidine tract, and the methods comprise injection of the virus in a desired brain region stereotaxically. In some embodiments, the virus comprises adenovirus, lentivirus, adeno-associated virus (AAV), poliovirus, herpes simplex virus (HSV), or murine Maloney-based virus. The AAV that can be used in the methods provided herein can be any appropriate serotype of AAV, such as, but not limited to, AAV2, AAV5, AAV6, AAV7, and AAV8. In some embodiments, the methods comprise delivering an AAV2-based viral vector that expresses an agent that suppresses expression or activity of PTB in a non-neuronal cell in a region in nervous system, e.g., brain or spinal cord. In some embodiments, the cell-programming agent comprises a small molecule inhibitor of PTB.

In some embodiments, as described above, the methods provided herein comprise reprogramming a variety of non-neuronal cells to mature neurons. In some embodiments, the methods provided herein comprise administering to a region in the nervous system, e.g., brain or spinal cord, of a subject a composition comprising a cell-programming agent that suppresses the expression or activity of PTB in a variety of non-neuronal cells, such as, but not limited to, glial cells, e.g., astrocyte, oligodendrocyte, NG2 cell, satellite cell, or ependymal cell in the nervous system, and allowing the non-neuronal cell to reprogram into the functional neuron. In some embodiments, the methods provided herein comprise reprogramming astrocyte in a region in the nervous system, e.g., brain or spinal cord, of a subject into a functional neuron.

As discussed above, the methods provided herein can comprise reprogramming a non-neuronal cell in a specific brain region into a functional neuron. Exemplary brain regions that can be used in the methods provided herein can be in any of hindbrain, midbrain, or forebrain. In some embodiments, the methods provided herein comprise administering to a midbrain, striatum, or cortex of a subject a composition comprising a cell-programming agent that suppresses the expression or activity of PTB in a non-neuronal cell in the midbrain, and allowing the non-neuronal cell to reprogram into the functional neuron. In some embodiments, the methods provided herein comprise administering to midbrain of a subject a composition comprising a cell-programming agent that suppresses the expression or activity of PTB in a non-neuronal cell in the midbrain, and allowing the non-neuronal cell to reprogram into the functional neuron.

In some embodiments, the methods provided herein comprise reprogramming a non-neuronal cell into a functional neuron in a brain region, such as, but not limited to, medulla oblongata, medullary pyramids, olivary body, inferior olivary nucleus, rostral ventrolateral medulla, caudal ventrolateral medulla, solitary nucleus, respiratory center-respiratory groups, dorsal respiratory group, ventral respiratory group or apneustic centre, pre-botzinger complex, botzinger complex, retrotrapezoid nucleus, nucleus retrofacialis, nucleus retroambiguus, nucleus para-ambiguus, paramedian reticular nucleus, gigantocellular reticular nucleus, parafacial zone, cuneate nucleus, gracile nucleus, perihypoglossal nuclei, intercalated nucleus, prepositus nucleus, sublingual nucleus, area postrema, medullary cranial nerve nuclei, inferior salivatory nucleus, nucleus ambiguous, dorsal nucleus of vagus nerve, hypoglossal nucleus, metencephalon, pons, pontine nuclei, pontine cranial nerve nuclei, chief or pontine nucleus of the trigeminal nerve sensory nucleus, motor nucleus for the trigeminal nerve (v), abducens nucleus (vi), facial nerve nucleus (vii), vestibulocochlear nuclei (vestibular nuclei and cochlear nuclei) (viii), superior salivatory nucleus, pontine tegmentum, pontine micturition center (barrington's nucleus), locus coeruleus, pedunculopontine nucleus, laterodorsal tegmental nucleus, tegmental pontine reticular nucleus, parabrachial area, medial parabrachial nucleus, lateral parabrachial nucleus, subparabrachial nucleus (kolliker-fuse nucleus), pontine respiratory group, superior olivary complex, medial superior olive, lateral superior olive, medial nucleus of the trapezoid body, paramedian pontine reticular formation, parvocellular reticular nucleus, caudal pontine reticular nucleus, cerebellar peduncles, superior cerebellar peduncle, middle cerebellar peduncle, inferior cerebellar peduncle, fourth ventricle, cerebellum, cerebellar vermis, cerebellar hemispheres, anterior lobe, posterior lobe, flocculonodular lobe, cerebellar nuclei, fastigial nucleus, interposed nucleus, globose nucleus, emboliform nucleus, dentate nucleus, midbrain (mesencephalon), tectum, corpora quadrigemina, inferior colliculi, superior colliculi, pretectum, tegmentum, periaqueductal gray, rostral interstitial nucleus of medial longitudinal fasciculus, midbrain reticular formation, dorsal raphe nucleus, red nucleus, ventral tegmental area, parabrachial pigmented nucleus, paranigral nucleus, rostromedial tegmental nucleus, caudal linear nucleus, rostral linear nucleus of the raphe, interfascicular nucleus, substantia nigra, pars compacta, pars reticulata, interpeduncular nucleus, cerebral peduncle, crus cerebri, mesencephalic cranial nerve nuclei, oculomotor nucleus (iii), edinger-westphal nucleus, trochlear nucleus (iv), mesencephalic duct (cerebral aqueduct, aqueduct of sylvius), forebrain (prosencephalon), diencephalon, epithalamus, pineal body, habenular nuclei, stria medullaris, taenia thalami, third ventricle, subcommissural organ, thalamus, anterior nuclear group, anteroventral nucleus (a.k.a. ventral anterior nucleus), anterodorsal nucleus, anteromedial nucleus, medial nuclear group, medial dorsal nucleus, midline nuclear group, paratenial nucleus, reuniens nucleus, rhomboidal nucleus, intralaminar nuclear group, centromedian nucleus, parafascicular nucleus, paracentral nucleus, central lateral nucleus, lateral nuclear group, lateral dorsal nucleus, lateral posterior nucleus, pulvinar, ventral nuclear group, ventral anterior nucleus, ventral lateral nucleus, ventral posterior nucleus, ventral posterior lateral nucleus, ventral posterior medial nucleus, metathalamus, medial geniculate body, lateral geniculate body, thalamic reticular nucleus, hypothalamus (limbic system) (hpa axis), anterior, medial area, parts of preoptic area, medial preoptic nucleus, suprachiasmatic nucleus, paraventricular nucleus, supraoptic nucleus (mainly), anterior hypothalamic nucleus, lateral area, parts of preoptic area, lateral preoptic nucleus, anterior part of lateral nucleus, part of supraoptic nucleus, other nuclei of preoptic area, median preoptic nucleus, periventricular preoptic nucleus, tuberal, medial area, dorsomedial hypothalamic nucleus, ventromedial nucleus, arcuate nucleus, lateral area, tuberal part of lateral nucleus, lateral tuberal nuclei, posterior, medial area, mammillary nuclei, posterior nucleus, lateral area, posterior part of lateral nucleus, optic chiasm, subfornical organ, periventricular nucleus, pituitary stalk, tuber cinereum, tuberal nucleus, tuberomammillary nucleus, tuberal region, mammillary bodies, mammillary nucleus, subthalamus, subthalamic nucleus, zona incerta, pituitary gland, neurohypophysis, pars intermedia (intermediate lobe), adenohypophysis, frontal lobe, parietal lobe, occipital lobe, temporal lobe, cerebellum, brainstem, centrum semiovale, corona radiata, internal capsule, external capsule, extreme capsule, subcortical, hippocampus, dentate gyrus, cornu ammonis (CA fields), cornu ammonis area 1 (CA1), cornu ammonis area 2 (CA2), cornu ammonis area 3 (CA3), cornu ammonis area 4 (CA4), amygdala, central nucleus of amygdala, medial nucleus of amygdala, cortical and basomedial nuclei of amygdala, lateral and basolateral nuclei of amygdala, extended amygdala, stria terminalis, bed nucleus of the stria terminalis, claustrum, basal ganglia, striatum, dorsal striatum, putamen, caudate nucleus, ventral striatum, nucleus accumbens, olfactory tubercle, globus pallidus, ventral pallidum, subthalamic nucleus, basal forebrain, anterior perforated substance, substantia innominata, nucleus basalis, diagonal band of broca, septal nuclei, medial septal nuclei, lamina terminalis, vascular organ of lamina terminalis, rhinencephalon (paleopallium), olfactory bulb, olfactory tract, anterior olfactory nucleus, piriform cortex, anterior commissure, uncus, periamygdaloid cortex, cerebral cortex, frontal lobe, cortex, primary motor cortex (precentral gyrus, M1), supplementary motor cortex, premotor cortex, prefrontal cortex, orbitofrontal cortex, dorsolateral prefrontal cortex, gyri, superior frontal gyrus, middle frontal gyrus, inferior frontal gyrus, Brodmann areas 4, 6, 8, 9, 10, 11, 12, 24, 25, 32, 33, 44, 45, 46, and 47, parietal lobe, cortex, primary somatosensory cortex (S1), secondary somatosensory cortex (S2), posterior parietal cortex, gyri, postcentral gyrus (primary somesthetic area), precuneus, Brodmann areas 1, 2, 3, 5, 7, 23, 26, 29, 31, 39, and 40, occipital lobe, cortex, primary visual cortex (V1), v2, v3, v4, v5/mt, gyri, lateral occipital gyrus, cuneus, Brodmann areas 17 (V1, primary visual cortex); 18, and 19, temporal lobe, cortex, primary auditory cortex (A1), secondary auditory cortex (A2), inferior temporal cortex, posterior inferior temporal cortex, gyri, superior temporal gyrus, middle temporal gyrus, inferior temporal gyrus, entorhinal cortex, perirhinal cortex, parahippocampal gyrus, fusiform gyrus, Brodmann areas 20, 21, 22, 27, 34, 35, 36, 37, 38, 41, and 42, medial superior temporal area (MST), insular cortex, cingulate cortex, anterior cingulate, posterior cingulate, retrosplenial cortex, indusium griseum, subgenual area 25, and Brodmann areas 23, 24; 26, 29, 30 (retrosplenial areas); 31, and 32.

In one aspect, the present disclosure provides a method of generating a dopaminergic neuron in vivo. An exemplary method comprises administering to a brain of a subject a composition comprising a cell-programming agent that suppresses expression or activity of PTB in a non-neuronal cell in the brain, and allowing the non-neuronal cell to reprogram into the dopaminergic neuron. In some embodiments, the methods comprise administering the composition into midbrain of the subject, in order to generate the dopaminergic neuron. In some embodiments, the composition is administered into substantial nigra (SN). In some embodiments, the composition is administered to ventral tegmental area (VTA).

In some embodiments, the methods provided herein comprise administering to a region in the nervous system, e.g., brain or spinal cord, of a subject a composition comprising a cell-programming agent that suppresses the expression or activity of PTB in a non-neuronal cell in the region, and allowing the non-neuronal cell to reprogram into a functional neuron of a subtype that is predominant in the region. Without being bound to a particular theory, the methods provided herein can take advantage of local induction signals in a region, e.g., a specific brain region, when reprogramming a non-neuronal cell into a functional neuron in vivo. For example, dopamine neurons are clustered in midbrain regions, e.g., substantial nigra (SN), ventral tegmental area (VTA), or retrorubral field (RRF). Local neurons, non-neuronal cells, e.g., astrocytes, microglia, or both, or other local constituents of the midbrain can contribute to the subtype specification of the neuron that is generated from the non-neuronal cell under the induction of the cell-programming agent.

In some embodiments, the methods provided herein comprise administering to a brain region of a subject a composition comprising a cell-programming agent that suppresses the expression or activity of PTB in a plurality of non-neuronal cell in the brain region, and the methods further comprise reprogramming at least about 5%, at least about 10%, at least about 20%, at least about 25%, at least about 30%, at least about 35%, at least about 38%, at least about 40%, at least about 42%, at least about 44%, at least about 46%, at least about 48%, at least about 50%, at least about 52%, at least about 54%, at least about 56%, at least about 58%, at least about 60%, at least about 62%, at least about 64%, at least about 66%, at least about 68%, at least about 70%, at least about 72%, at least about 74%, at least about 76%, at least about 78%, at least about 80%, at least about 82%, at least about 84%, at least about 86%, at least about 88%, at least about 90%, at least about 92%, at least about 94%, at least about 96%, at least about 98%, or at least about 99% of the non-neuronal cells to dopaminergic neurons. In some embodiments, the methods provided herein comprise administering to a brain region of a subject a composition comprising a cell-programming agent that suppresses the expression or activity of PTB in a plurality of non-neuronal cell in the brain region, and at least about 5%, at least about 10%, at least about 20%, at least about 25%, at least about 30%, at least about 35%, at least about 38%, at least about 40%, at least about 42%, at least about 44%, at least about 46%, at least about 48%, at least about 50%, at least about 52%, at least about 54%, at least about 56%, at least about 58%, at least about 60%, at least about 62%, at least about 64%, at least about 66%, at least about 68%, at least about 70%, at least about 72%, at least about 74%, at least about 76%, at least about 78%, at least about 80%, at least about 82%, at least about 84%, at least about 86%, at least about 88%, at least about 90%, at least about 92%, at least about 94%, at least about 96%, at least about 98%, or at least about 99% of the functional neurons generated by the methods are dopaminergic. In some embodiments, the dopaminergic neuron generated in the methods provided herein expresses one or more markers of dopaminergic neurons, including, but not limited to, dopamine, tyrosine hydroxylase (TH), dopamine transporter (DAT), vesicular monoamine transporter 2 (VMAT2), engrailed homeobox 1 (En1), Nuclear receptor related-1 (Nurr1), G-protein-regulated inward-rectifier potassium channel 2 (Girk2), forkhead box A2 (FoxA2), orthodenticle homeobox 2 (OTX2) and/or LIM homeobox transcription factor 1 alpha (Lmx1a). In some embodiments, the dopamine neuron generated in the methods provided herein exhibit $I_h$ current, which can be mediated by Hyperpolarization-activated cyclic nucleotide-gated (HCN) channels. $I_h$ current can be characterized as a slowly activating, inward current, which can be activated by hyperpolarizing steps. For instance, under voltage clamp and the holding potential Vh is −40 mV, an inward slowly activating current can be triggered in a dopamine neuron, with a reversal potential close to −30 mV. The activation curve of $I_h$ current characteristic of a dopamine neuron generated in the methods provided herein can range from −50 to −120 mV with a mid-activation point of −84-1 mV. In some embodiments, the dopaminergic neurons generated in the methods provided herein have gene expression profile similar to a native dopaminergic neuron. In some embodiments, the dopaminergic neurons generated in the methods provided herein release dopamine as a neurotransmitter. A dopaminergic neuron generated in the methods provided herein can be of any subtype of dopaminergic neuron, including, but not limited to, A9 (e.g., immunopositive for Girk2), A10 (e.g., immunopositive for calbindin-D28k), A11, A12, A13, A16, Aaq, and telencephalic dopamine neurons.

According to some embodiments of the present disclosure, the methods provided herein comprise reprogramming a non-neuronal cell in a region in the nervous system, e.g., brain or spinal cord, of a subject to a functional neuron. In some embodiments, the functional neuron as discussed here is integrated into the neural network in the nervous system. As described herein, the reprogrammed functional neuron can form synaptic connections with local neurons, e.g., neurons that are adjacent to the reprogrammed functional neurons. For example, synaptic connections between the reprogrammed neuron and neighboring primary neuron (e.g., glutamatergic neurons), GABAergic interneurons, or other neighboring neurons (e.g., dopaminergic neuron, adrenergic neurons, or cholinergic neurons) can form as the reprogrammed neuron matures in vivo. Among these synaptic connections with local neurons, the reprogrammed functional neuron can be a presynaptic neuron, a postsynaptic neuron, or both. In some embodiments, the reprogrammed functional neuron sends axonal projections to remote brain regions. For example, a dopaminergic neuron in midbrain region that is generated according to some embodiments herein can project to the striatum, which is a regular target of native dopaminergic neurons from midbrain region. A dopaminergic neuron in midbrain region that is generated according to some embodiments herein can project to caudate putamen, nucleus accumbens, septal nucleus, olfactory tubercle, or any combinations thereof. A dopaminergic neuron in midbrain region that is generated according to some embodiments herein can project to brain regions where native dopaminergic neurons in midbrain region can project to. In some embodiments, a reprogrammed functional neuron can integrate itself into one or more existing neural pathways in the brain or spinal cord, for instance, but not limited to, superior longitudinal fasciculus, arcuate fasciculus, uncinate fasciculus, perforant pathway, thalamocortical radiations, corpus callosum, anterior commissure, amygdalofugal pathway, interthalamic adhesion, posterior commissure, habenular commissure, fornix, mammillotegmental fasciculus, incertohypothalamic pathway, cerebral peduncle, medial forebrain bundle, medial longitudinal fasciculus, myoclonic triangle, mesocortical pathway, mesolimbic pathway, nigrostriatal pathway, tuberoinfundibular pathway, extrapyramidal system, pyramidal tract, corticospinal tract or cerebrospinal fibers, lateral corticospinal tract, anterior corticospinal tract, corticopontine fibers, frontopontine fibers, temporopontine fibers, corticobulbar tract, corticomesencephalic tract, tectospinal tract, interstitiospinal tract, rubrospinal tract, rubro-olivary tract, olivocerebellar tract, olivospinal tract, vestibulospinal tract, lateral vestibulospinal tract, medial vestibulospinal tract, reticulospinal tract, lateral raphespinal tract, posterior column-medial lemniscus pathway, gracile fasciculus, cuneate fasciculus, medial lemniscus, spinothalamic tract, lateral spinothalamic tract, anterior spinothalamic tract, spinomesencephalic tract, spinocerebellar tract, spino-olivary tract, and spinoreticular tract. Without being bound to a certain theory, local cellular environment can be correlated with the projections of a functional neuron generated according to some embodiments of the present disclosure. For instance, a functional neuron generated in midbrain according to some embodiments of the methods provided herein can be affected by other cells in the local environment of midbrain, for instance the cells that release guidance signals for axonal growth of other native dopaminergic neurons, or the native dopaminergic neurons that project the common target brain regions.

In an aspect, the present disclosure provides a method of treating a neurological condition associated with degeneration of functional neurons in a region in the nervous system. An exemplary comprises administering to the region of the nervous system, e.g., brain or spinal, of a subject in need thereof a composition comprising a cell-programming agent that suppresses the expression or activity of PTB in a non-neuronal cell in the region, and allowing the non-neuronal cell to reprogram into a functional neuron, thereby replenishing the degenerated functional neurons in the region.

According to some embodiments of the present disclosure, methods provided herein comprise treating neurological conditions, including, but not limited to, Parkinson's disease, Alzheimer's disease, Huntington's disease, Schizophrenia, depression, and drug addiction. Applicable neurological conditions can also include disorders associated with neuronal loss in spinal cord, such as, but not limited to, Amyotrophic lateral sclerosis (ALS) and motor neuron disease. The methods provided herein can also find use in treating or ameliorating one or more symptoms of neurodegenerative diseases including, but not limited to, autosomal dominant cerebellar ataxia, autosomal recessive spastic ataxia of Charlevoix-Saguenay, Corticobasal degeneration, Corticobasal syndrome, Creutzfeldt-Jakob disease, fragile X-associated tremor/ataxia syndrome, frontotemporal dementia and parkinsonism linked to chromosome 17, Kufor-Rakeb syndrome, Lyme disease, Machado-Joseph disease, Niemann-Pick disease, pontocerebellar hypoplasia, Refsum disease, pyruvate dehydrogenase complex deficiency, Sandhoff disease, Shy-Drager syndrome, Tay-Sachs disease, and Wobbly hedgehog syndrome. As provided herein, "neurodegeneration" or its grammatical equivalents, can refer to the progressive loss of structure, function, or both of neurons, including death of neuron. Neurodegeneration can be due to any type of mechanisms. A neurological condition the methods provided herein are applicable to can be of any etiology. A neurological condition can be inherited or sporadic, can be due to genetic mutations, protein misfolding, oxidative stress, or environment exposures (e.g., toxins or drugs of abuse).

In some embodiments, the methods provided herein treat a neurological condition associated with degeneration of dopaminergic neurons in a brain region. In other embodiments, the methods provided herein treat a neurological condition associated with degeneration of any type of neurons, such as, but not limited to, glutamatergic neurons, GABAergic neurons, cholinergic neurons, adrenergic neurons, dopaminergic neurons, or any other appropriate type neurons that release neurotransmitter aspartate, D-serine, glycine, nitric oxide (NO), carbon monoxide (CO), hydrogen sulfide (H2S), norepinephrine (also known as noradrenaline), histamine, serotonin, phenethylamine, N-methylphenethylamine, tyramine, 3-iodothyronamine, octopamine, tryptamine, somatostatin, substance P, opioid peptides, adenosine triphosphate (ATP), adenosine, or anandamide. The methods provided herein can find use in treating a neurological condition associated with neuronal degeneration in any region, such as, but limited to, midbrain regions (e.g., substantial nigra or ventral tegmental area), forebrain regions, hindbrain regions, or spinal cord. The methods provided herein can comprise reprogramming non-neuronal cells to functional neurons in any appropriate region(s) in the nervous system in order to treat a neurological condition associated with neuronal degeneration.

Methods provided herein can find use in treating or ameliorating one or more symptoms associate with Parkinson's disease. Parkinson's disease is a neuro-degenerative disease with early prominent functional impairment or death of dopaminergic neurons in the substantia nigra pars compacta (SNpc). The resultant dopamine deficiency within the basal ganglia can lead to a movement disorder characterized by classical parkinsonian motor symptoms. Parkinson's disease can also be associated with numerous non-motor symptoms. One standard for diagnosis of Parkinson's disease can be the presence of SNpc degeneration and Lewy pathology at post-mortem pathological examination. Lewy pathology can include abnormal aggregates of α-synuclein protein, called Lewy bodies and Lewy neurites. Patients with Parkinson's disease can exhibit a number of symptoms, including motor symptoms and non-motor symptoms. Methods provided herein can treat or ameliorate one or more of these motor or non-motor symptoms associated with Parkinson's disease. Motor symptoms of Parkinson's disease (Parkinsonism symptoms) can include bradykinesia (slowness), stiffness, impaired balance, shuffling gait, and postural instability. Motor features in patients with Parkinson's disease can be heterogeneous, which has prompted attempts to classify subtypes of the disease, for instance, tremor-dominant Parkinson's disease (with a relative absence of other motor symptoms), non-tremor-dominant Parkinson's disease (which can include phenotypes described as akinetic-rigid syndrome and postural instability gait disorder), and an additional subgroup with a mixed or indeterminate phenotype with several motor symptoms of comparable severity. Non-motor symptoms of Parkinson's disease can include olfactory dysfunction, cognitive impairment, psychiatric symptoms (e.g., depression), sleep disorders, autonomic dysfunction, pain, and fatigue. These symptoms can be common in early Parkinson's disease. Non-motor features can also be frequently present in Parkinson's disease before the onset of the classical motor symptoms. This premotor or prodromal phase of the disease can be characterized by impaired olfaction, constipation, depression, excessive daytime sleepiness, and rapid eye movement sleep behavior disorder.

In some embodiments, methods provided herein mitigate or slow the progression of Parkinson's disease. Progression of Parkinson's disease can be characterized by worsening of motor features. As the disease advances, there can be an emergence of complications related to long-term symptomatic treatment, including motor and non-motor fluctuations, dyskinesia, and psychosis.

One pathological feature of Parkinson's disease can be loss of dopaminergic neurons within the substantial nigra, e.g., substantial nigra pars compacta (SNpc). According to some embodiments, methods provided herein replenish functional dopamine neuron in substantial nigra (e.g., SNpc) of a patient. Neuronal loss in Parkinson's disease can also occur in many other brain regions, including the locus ceruleus, nucleus basalis of Meynert, pedunculopontine nucleus, raphe nucleus, dorsal motor nucleus of the vagus, amygdala, and hypothalamus. In some embodiments, methods of treating or ameliorating one or more symptoms of Parkinson's disease in a subject as provided herein include reprogramming non-neuronal cells to functional neurons in brain regions experiencing neuronal loss in a patient with Parkinson's disease.

Methods provided herein can find use in treating Parkinson's disease of different etiology. For example, there can be Parkinson's disease as a result of one or more genetic mutations, such as, but not limited to, mutations in genes SNCA, LRRK2, VPS35, EIF4G1, DNAJC13, CHCHD2, Parkin, PINK1, DJ-1, ATP13A2, C9ORF72, FBXO7, PLA2G6, POLG1, SCA2, SCA3, SYNJ1, RAB39B, and possibly one or more genes affected in 22q11.2 microdeletion syndrome. Or there can be Parkinson's disease with no known genetic traits.

As provided herein, the one or more symptoms of Parkinson's disease the methods provided herein can ameliorate can include not only the motor symptoms and non-symptoms as described above, but also pathological features at other levels. For example, reduction in dopamine signaling in the brain of a patient with Parkinson's disease can be reversed or mitigated by methods provided herein by replenishing functional dopamine neurons, which can be integrated into the neural circuitry and reconstruct the dopamine neuron projections to appropriate brain regions, e.g., striatum.

In an aspect, the present disclosure also provides methods of restoring dopamine release in subject with a decreased amount of dopamine biogenesis compared to a normal level. An exemplary method comprises reprogramming a non-neuronal cell in a brain region of the subject, and allowing the non-neuronal cell to reprogram into a dopaminergic neuron, thereby restoring at least 50% of the decreased amount of dopamine. In some embodiments, the reprogramming is performed by administering to the brain region of the subject a composition comprising a cell-programming agent that suppresses the expression or activity of PTB in a non-neuronal cell in the brain region. In some embodiments, the methods provided herein restore at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 98% of the decreased amount of dopamine. In some embodiments, the methods provided herein restore about 20%, about 25%, about 30%, about 35%, about 40%, about 45%, about 50%, about 55%, about 60%, about 65%, about 70%, about 75%, about 80%, about 85%, about 90%, about 95%, about 98%, or about 100% of the decreased amount of dopamine. In some embodiments, the methods provided herein restore at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 98% of the decreased amount of dopamine. In some embodiments, the methods provided herein restore at least about 50% of the decreased amount of dopamine.

In one aspect, the present disclosure provides pharmaceutical compositions comprising a cell-programming agent in an amount effective to reprogram a mammalian non-neuronal cell to a mature neuron by suppressing the expression or activity of PTB in the non-neuronal cell. An exemplary pharmaceutical composition can further comprise a pharmaceutically acceptable carrier or excipient. As described above, a cell-programming agent as provided herein can be a small chemical molecule, interfering RNA, short hairpin RNA, microRNA, dominant negative mutant, ribozyme, antisense oligonucleotide, protein inhibitor, monoclonal antibody, a polyclonal antibody, a peptide, or any form of modified nucleic acid.

A pharmaceutical composition provided herein can include one or more carriers and excipients (including but not limited to buffers, carbohydrates, mannitol, proteins, peptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In another instance, the composition is substantially free of preservatives. In other embodiments, the composition contains at least one preservative. General methodology on pharmaceutical dosage forms can be found in Ansel et ah, Pharmaceutical Dosage Forms and Drug Delivery Systems (Lippencott Williams & Wilkins, Baltimore Md. (1999)). It will be recognized that, while any suitable carrier known to those of ordinary skill in the art can be employed to administer the pharmaceutical compositions described herein, the type of carrier can vary depending on the mode of administration. Suitable formulations and additional carriers are described in Remington "The Science and Practice of Pharmacy" (20th Ed., Lippincott Williams & Wilkins, Baltimore Md.), the teachings of which are incorporated by reference in their entirety herein. An exemplary pharmaceutical composition can be formulated for injection, inhalation, parenteral administration, intravenous administration, subcutaneous administration, intramuscular administration, intradermal administration, topical administration, or oral administration. As one of ordinary skills in the art will appreciate, pharmaceutical compositions can comprise any appropriate carrier or excipient, depending on the type of cell-programming agent and the administration route the composition is designed for. For example, a composition comprising a cell-programming agent as provided herein can be formulated for parenteral administration and can be presented in unit dose form in ampoules, pre-filled syringes, small volume infusion or in multi-dose containers with an added preservative. The composition can take such forms as suspensions, solutions, or emulsions in oily or aqueous vehicles, for example solutions in aqueous polyethylene glycol. For example, for injectable formulations, a vehicle can be chosen from those known in the art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of active agent in injection grade water, liposomes, and vehicles suitable for lipophilic substances and those known in the art. A composition as provided herein can further comprise additional agent besides a cell-programming agent and a pharmaceutically acceptable carrier or excipient. For example, additional agent can be provided for promoting neuronal survival purpose. Alternatively or additionally, additional agent can be provided for monitoring pharmacodynamics purpose. In some embodiments, a composition comprises additional agent as a penetration enhancer or for sustained release or controlled release of the active ingredient, e.g., cell-programming agent.

A composition provided herein can be administered to a subject in a dosage volume of about 0.0005, 0.001, 0.002, 0.005, 0.01, 0.02, 0.05, 0.1, 0.15, 0.2, 0.25, 0.3, 0.35, 0.4, 0.45, 0.5, 0.55, 0.6, 0.7, 0.8, 0.9, 1.0 mL, or more. The composition can be administered as a 1, 2, 3, 4, 5, 6, 7, 8, 9, 10, or more dose-course regimen. Sometimes, the composition can be administered as a 2, 3, or 4 dose-course regimen. Sometimes the composition can be administered as a 1 dose-course regimen.

The administration of the first dose and second dose of the 2 dose-course regimen can be separated by about 0 day, 1 day, 2 days, 5 days, 7 days, 14 days, 21 days, 30 days, 2 months, 4 months, 6 months, 9 months, 1 year, 1.5 years, 2 years, 3 years, 4 years, 5 years, 10 years, 20 years, or more. A composition described herein can be administered to a subject once a day, once a week, once two weeks, once a month, a year, twice a year, three times a year, every 1, 2, 3, 4, 5, 6, 7, 8, 9, 10, or more years. Sometimes, the composition can be administered to a subject every 2, 3, 4, 5, 6, 7, or more years. Sometimes, the composition can be administered to a subject once.

Some embodiments of the disclosure provide methods and compositions for cell or tissue transplantation. An exemplary method can comprise reprogramming a non-neuronal cell to a neuron in vitro, and transplanting the reprogrammed neuron into a brain region in a subject. In some embodiments, in vitro reprogramming can be performed according to the methods provided herein. An exemplary composition can comprise a neuron reprogrammed according to any embodiment of the methods provided herein.

In other embodiments, a method provided herein comprises reprogramming a non-neuronal cell to a neuron in vivo, and explanting the reprogrammed neuron. In some embodiments, the explant comprises a brain tissue comprising the reprogramed neuron. In some embodiments, the explant is transplanted into a brain region of a subject. As provided herein, the transplantation of neurons reprogrammed according to the methods provided herein can be used to replenish degenerated neurons in a subject suffering a condition associated with neuronal loss.

Some other aspects of the present disclosure relate to an animal that comprise neurons reprogrammed according to any embodiment of the methods provided herein. As provided herein, an animal can be any mammal. An animal can be a human. An animal can be a non-human primate, such as, but not limited, rhesus macaques, crab-eating macaques, stump-tailed macaques, pig-tailed macaques, squirrel monkeys, owl monkeys, baboons, chimpanzees, marmosets and spider monkeys. An animal can be a research animal, a genetically modified animal, or any other appropriate type of animal. For example, a mouse or rat can be provided that comprises one or more neurons reprogrammed according to an embodiment of the present disclosure. Also provided herein is a brain tissue (e.g., explant) of an animal that comprises one or more neurons reprogrammed according to any embodiment of the present disclosure. Such brain tissue can be live. In some embodiments, a brain tissue can be fixed by any appropriate fixative. A brain tissue can be used for transplantation, medical research, basic research, or any type of purposes.

The disclosure demonstrates that the method is applicable to disease models of neurodegeneration. For example, the disclosure shows that astrocyte-to-neuron conversion strategy can work in a chemical-induced Parkinson's disease model. The methods and compositions can convert astrocytes to neurons including dopaminergic, glutamatergic and GABAergic neurons, these neurons are able to form synapses in the brain, and remarkably, the converted neurons can efficiently reconstruct the lesioned nigrostriatal pathway to correct measurable Parkinson's phenotypes. The effectiveness of this method was demonstrated both in astrocytes in culture (human and mouse) as well as in vivo in a mouse Parkinson's disease model using a single dose of anti-PTB ASO. Not only that, the converted neurons can extend processes into the striatum. Therefore, this strategy has the potential to cure Parkinson's disease, which can also be applied to a wide range of neurodegenerative diseases (e.g., other neurological diseases associated with neuronal dysfunction). In some embodiments, the approach of the disclosure exploits the genetic foundation of a neuronal maturation program already present, but latent, in both mammalian astrocytes that progressively produce mature neurons once they are reprogrammed by PTB suppression. These findings provide a clinically feasible approach to generate neurons from local astrocytes in mammalian brain using a single dose of anti-PTB ASO or delivery of a vector comprising a siRNA. The phenotypes of PTB knockdown-induced neurons can be a function of the context in which they are produced and/or the astrocytes from which they are derived.

The disclosure demonstrates the potent conversion of astrocytes to neurons (e.g., dopamine neurons in the substantia nigra, a fraction of which send projections into the striatum, providing evidence for the reconstruction of the nigrostriatal dopamine pathway). More particularly, the disclosure shows that in a chemically-induced mouse Parkinson's disease (PD) model, the strategy efficiently can correct a PD phenotype, thus satisfying all five factors for in vivo reprogramming. The disclosure further shows that an antisense oligonucleotide (ASO) against PTB can also be effective in correcting the PD phenotype, suggesting the feasibility of a transient, hit-and-run strategy for treating PD and perhaps other neurodegenerative diseases.

The data provided herein show that PTB reduction in the mammalian brain can convert astrocytes to neurons (e.g., dopaminergic neurons capable of reconstituting the nigrostriatal pathway, as judged by the presence within the substantia nigra of newly converted neurons) and the reversal of behavioral deficits (e.g., in a chemically-induced PD model).

A "therapeutically effective amount" of a composition of the disclosure will vary according to factors such as the disease state, age, sex, and weight of the individual, and the ability of the composition to elicit a desired response in the individual. A therapeutically effective amount can also be one in which any toxic or detrimental effects of the composition are outweighed by the therapeutically beneficial effects. Without wishing to be bound by a particular theory, it is contemplated that, in some cases, a therapeutically effective amount of cell-programming agent as provided herein can be an amount of cell-programming agent that converts a certain proportion of astrocytes in a brain region that experiences neuronal loss, conversion of such proportion of astrocytes to functional neurons in the brain region is sufficient to ameliorate or treating the disease or condition associated with the neuronal loss in the brain region, and meanwhile, such proportion of astrocytes does not exceed a threshold level that can lead to aversive effects that can overweigh the beneficial effects brought by the neuronal conversion, for instance, due to excessive reduction in the number of astrocytes in the brain region as a direct consequence of the neuronal conversion.

The following examples are intended to illustrate but not limit the disclosure. While they are typical of those that might be used, other procedures known to those skilled in the art may alternatively be used.

EXAMPLES

Example 1. Expression of miR-9 and Brn2 in Astrocytes

Figure 2:
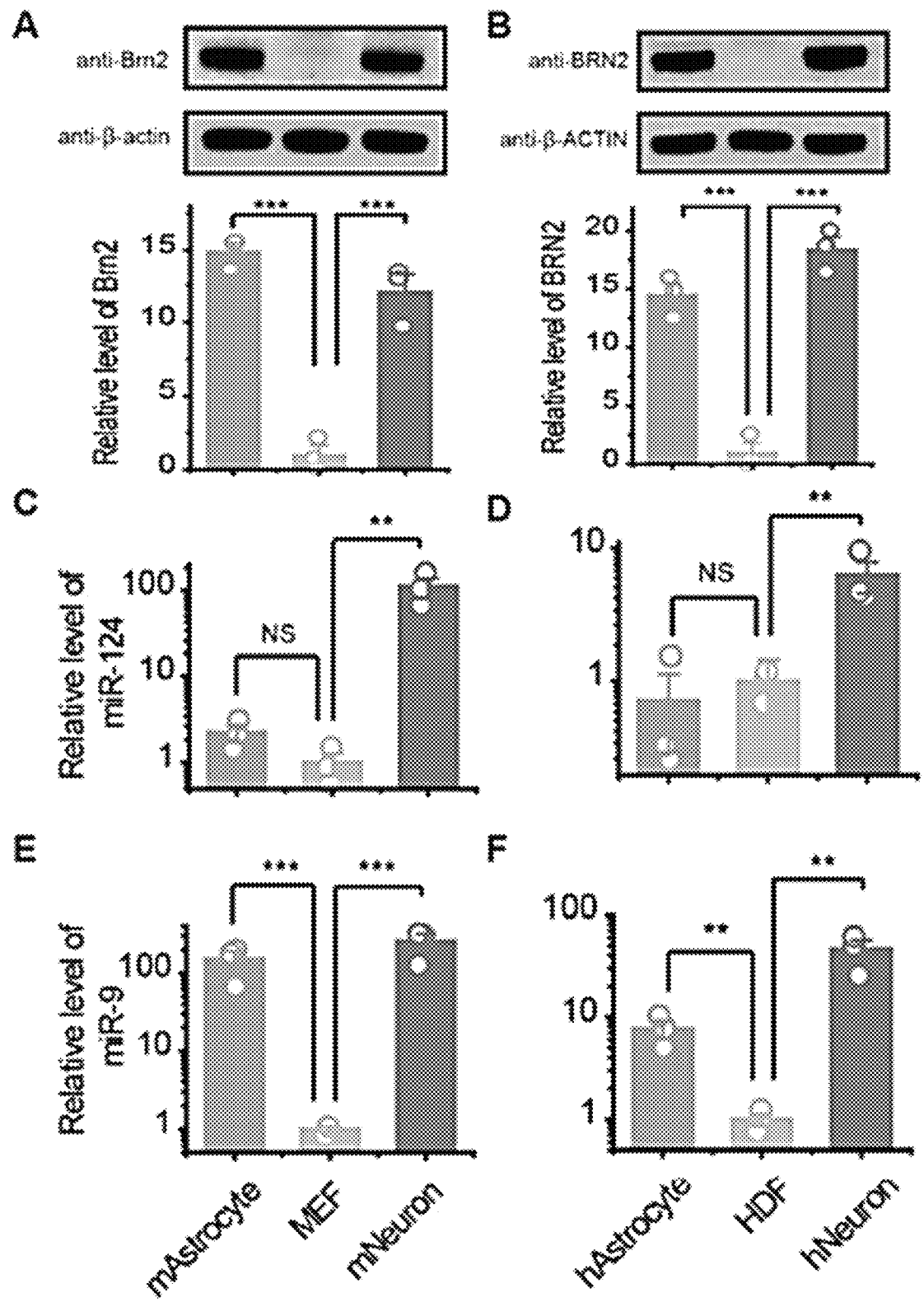
FIGS. 2A-F show expression levels of Brn2 by western blot and miR-124 and miR-9 by RT-qPCR in mouse astrocytes, mouse embryonic fibroblasts (MEFs) and mouse neurons (FIGS. 2A, 2C, and 2E) and in human astrocytes, human adult fibroblasts HDFs) and human neurons (FIGS. 2B, 2D and 2F). Statistical results are represented as mean±SEM; p<0.01, *p<0.001 based on ANOVA with post-hoc Turkey test (n=3 biological repeats).

PTB/nPTB-regulated gene expression programs were tested in mouse and human primary astrocytes. As demonstrated in FIGS. 2C-2F, miR-124 and miR-9 are both highly expressed in neurons, but not fibroblasts. In both human and mouse astrocytes, miR-124 was found to be present at low levels (FIGS. 2C and 2D), which may explain the high REST levels in this non-neuronal cell type and suggest a tight PTB-regulated loop in astrocytes. Unexpectedly, however, miR-9 was found to be highly expressed in both mouse and human astrocytes (FIGS. 2E and 2F). Brn2 followed the same expression pattern as miR-9, low in fibroblasts, but high in both astrocytes and neurons (FIGS. 2A and 2B). These observations are consistent with the notion that astrocytes and neurons may share common progenitors.

Figure 3:
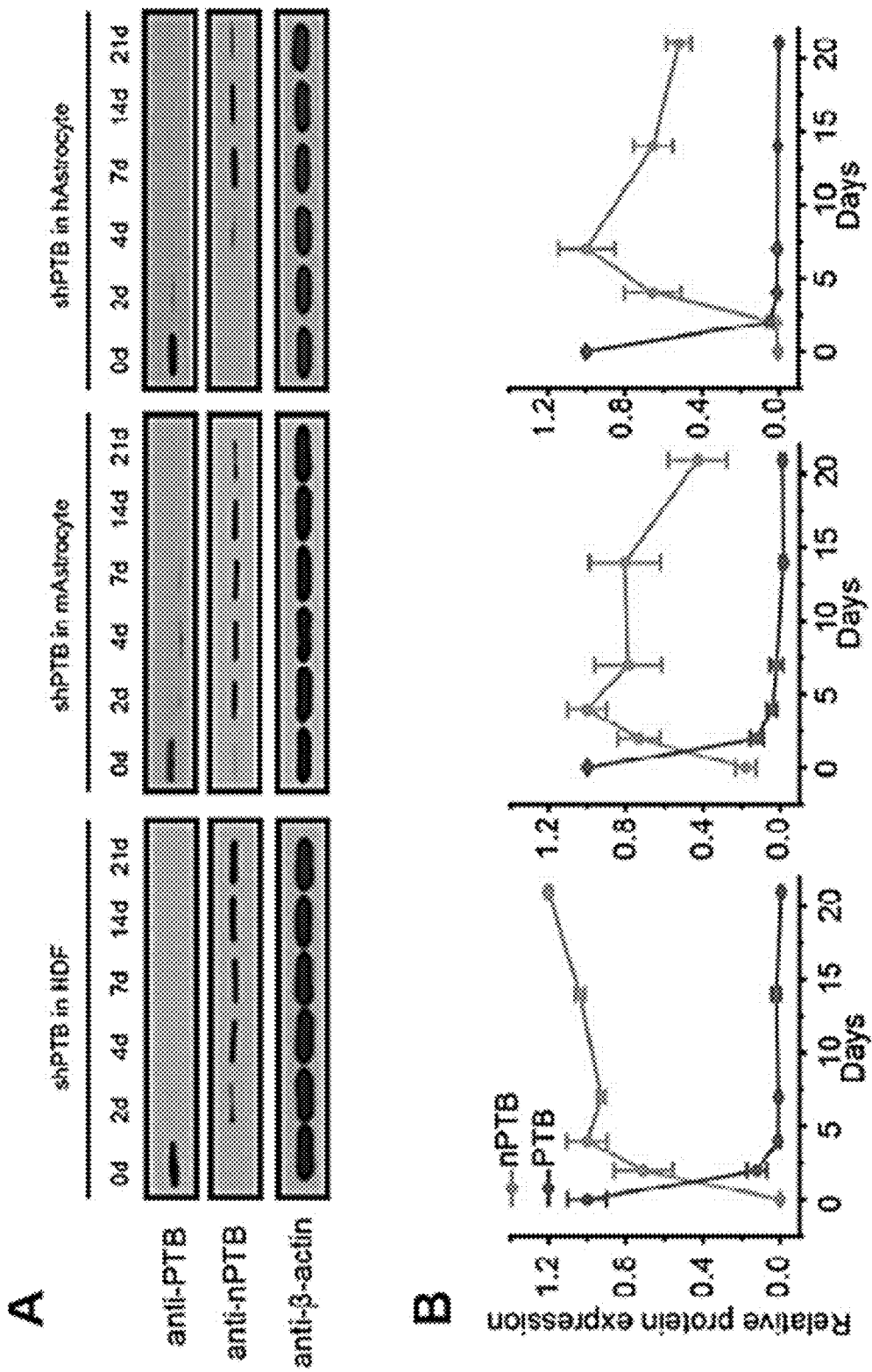
FIG. 3A shows time-course analysis of nPTB levels by western blot in response to PTB down-regulation in HDF (left), mouse (middle) and human astrocytes (right).
FIG. 3B shows quantifications of the data.

Example 2. Knockdown of PTB in Mouse and Human Astrocytes LED to nPTB Induction Followed by nPTB Decline It is recognized in the present disclosure that astrocytes already express factors that may be important for neuronal maturation (e.g. miR-9 and Brn2), the possibility was tested that PTB knockdown-induced nPTB is immediately counteracted by miR-9. In contrast to the PTB/nPTB expression profile in human fibroblasts, PTB knockdown was shown to lead to nPTB induction followed by nPTB decline in mouse and human astrocytes (FIGS. 3A and 3B). Therefore, by depleting PTB alone in astrocytes, the high levels of miR-9 can potentiate a stable reprogramming of astrocytes into mature neurons.

Figure 4:
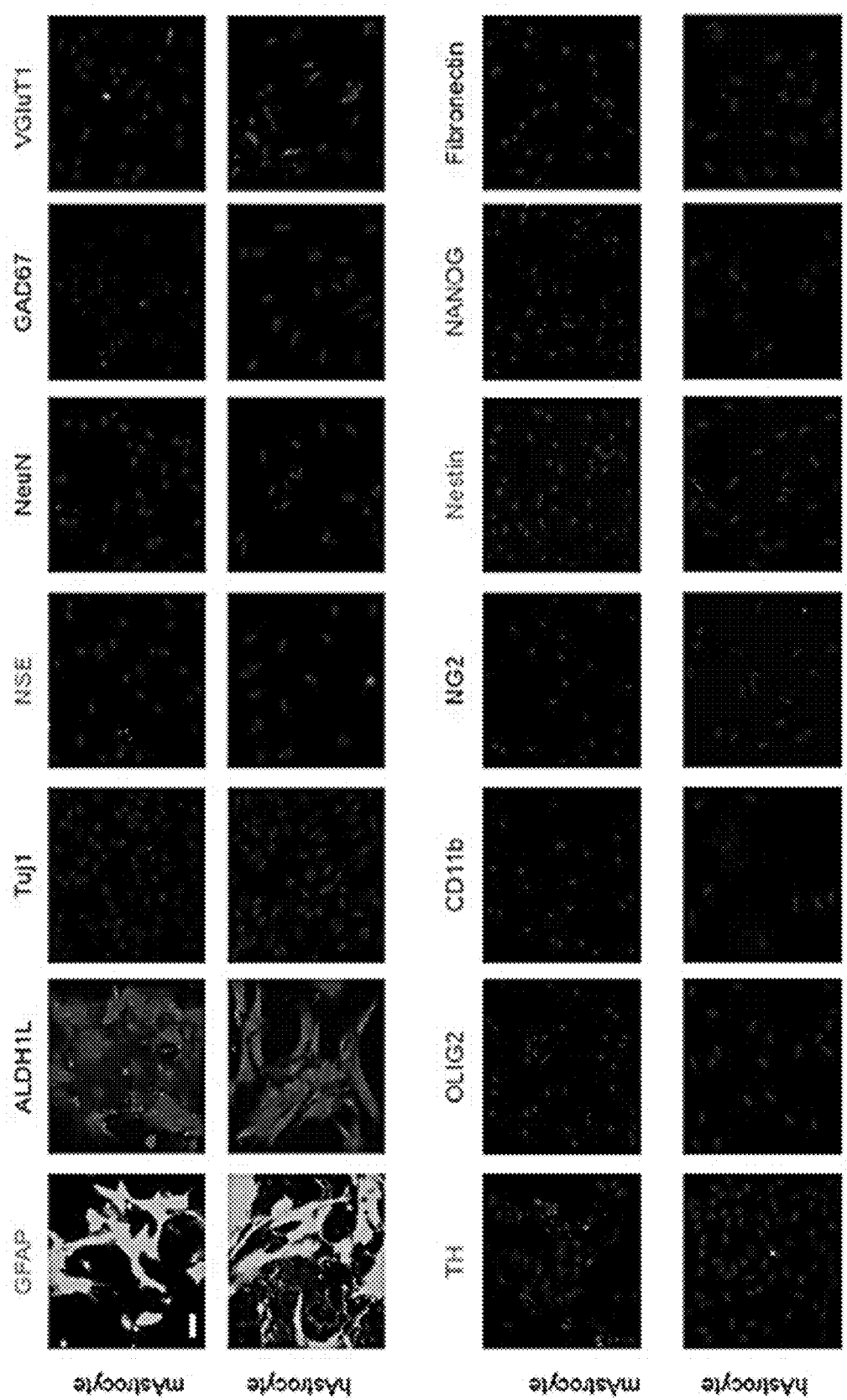
FIG. 4 shows the characterization of isolated mouse and human astrocytes: the majority of mouse and human astrocytes in the culture were immunopositive for astrocyte markers (GFAP and ALDH1L1), without detectable other cell types, as indicated by negative staining of neuronal markers (Tuj1, NSE, NeuN, GAD67, VGluT1, TH), oligodendrocyte marker (Oligodendrocyte Transcription Factor 2, OLIG2), Microglia marker (CD11 Antigen-Like Family Member B, CD11b), NG2 cell marker (Neural/glial antigen 2, NG2), neural progenitor marker (Nestin) pluripotency marker (NANOG) and fibroblast marker (Fibronectin). Scale bar: 30 um.

Example 3. Knock Down of PTB Efficiently Converted Astrocytes to Functional Neurons In Vitro To explore the possibility that PTB down-regulation would result in efficient conversion of astrocytes to mature neurons, mouse astrocytes were dissociated from cerebral cortex of postnatal day 4 to 5 (P4-5) pups and human fetal astrocytes were obtained from a commercial source (ScienCell). Cells from both sources expressed the expected astrocyte markers GFAP and ALDH1L1 without detectable contamination of neuronal cells, as indicated by absence of markers for neurons or neural crest progenitors (FIG. 4).

Mouse astrocytes were infected with a lentiviral vector expressing a small hairpin RNA against PTB (shPTB). Four weeks after transduction, ~50% of shPTB-treated cells maintained in standard neuronal differentiation medium containing a set of small molecules showed neuronal morphology and positive staining for the pan-neuronal marker Tuj1 and MAP2, while cells transduced with a control shRNA did not (FIG. 5A). The shPTB-induced neurons also expressed markers of mature neurons, including NeuN and a Neuron Specific Enolase (NSE) (FIG. 5B). To define the types of converted neurons, markers for glutamatergic neurons (VGlut1), GABAergic neurons (GAD67), dopaminergic neurons (tyrosine hydroxylase, TH), and others (FIG. 5C) were examined. The majority of induced neurons were either glutamatergic or GABAergic, with a few (1 to 2%) Tuj-1 positive cells expressing the dopaminergic marker (TH) (FIG. 5C). The expression of additional dopaminergic markers, such as SLC6A3 and FoxA2 by RT-qPCR as well as DAT and VMAT2, was examined by immunostaining, and their induction was observed at low efficiency (FIGS. 5I-L). None of the induced neurons expressed detectable cholinergic or serotonergic markers, including choline acetyltransferase or tryptophan hydroxylase.

To test the functionality of PTB knockdown-converted cells, patch clamp recordings were performed 5-6 weeks after shPTB expression. Most patched cells showed currents of voltage-gated sodium/potassium channels and repetitive action potential firing, indicative of neuronal activities of these converted cells (FIG. 5D). Furthermore, when co-culturing converted neurons with freshly isolated GFP-marked rat astrocytes, spontaneous postsynaptic events of varying frequencies were detected (FIG. 5D). These neuronal activities likely reflected the responses to synaptic inputs from both glutamatergic and GABAergic neurons, because 2,3-dihydroxy-6-nitro-7-sulfamoyl-benzo[f]quinoxaline-2,3-dione (NBQX) plus D(-)-2-amino-5-phosphonovaleric acid (APV) (antagonists of glutamatergic channel receptors) and Picrotoxin (PiTX, antagonist of GABAA channel receptors) could sequentially block the signals (FIG. 6A). No neuronal electrophysiological properties were detected in patch clamp recording of cells transduced with the control shRNA (FIG. 6B).

Human astrocytes appeared to be even more efficiently reprogrammed than mouse astrocytes. Four weeks after transduction with the shPTB lentiviral vector, nearly quantitative astrocyte-to-neuron conversion was observed with ~90% of the cells marked by neuron specific β-tubulin recognized by the Tuj1 antibody (FIG. 5E). Converted neurons expressed NeuN and NSE (FIG. 5F), and as with mouse astrocytes, human astrocytes were largely converted to glutamatergic or GABAergic neurons, with a small percent (1 to 2%) expressing detectable levels of TH (FIG. 5H). It is noted that, under the experimental conditions, compared with mouse astrocytes, the conversion efficiency was higher with human astrocytes, while the relative percentages of GAD67 and VGlut1 neuron subtypes were lower, perhaps indicating higher diversification of human astrocyte-derived neurons. Electrophysiological studies demonstrated currents carried by voltage-gated channels and repetitive action potentials in the vast majority of neurons 5-6 weeks after depletion of PTB, and when co-cultured with rat astrocytes, most human astrocyte-converted neurons also exhibited spontaneous postsynaptic events (FIG. 5H). These postsynaptic activities could be sequentially blocked NBQX+APV and PiTX (FIG. 6C) and no neuronal electrophysiological properties were detected in patch clamp recording of cells transduced with the control shRNA (FIG. 6D). These data demonstrate that both mouse and human astrocytes can be efficiently converted to functional neurons in a single step through down-regulating PTB.

Example 4. Knock Down of PTB Induced Direct Conversion of Astrocytes into Neurons in Mouse Midbrain An AAV-based strategy was designed by using AAV serotype 2 vector to express shPTB for in vivo delivery (FIG. 7A). To enable lineage tracing of converted neurons, a red fluorescence protein (RFP) gene was placed 5' to shPTB. A LoxP-Stop-LoxP unit was inserted 5' to RFP to allow for conditional expression of both RFP and shPTB. RFP positive cells were virtually absent 10 weeks after injecting this AAV-shPTB vector into the midbrain of wild-type (WT) mice (FIG. 8A). In contrast, when the same AAV vector was injected into the brain of transgenic mice that express the Cre recombinase under the astrocyte-specific GFAP promoter, both RFP and shPTB were selectively expressed in astrocytes (see below).

AAV-shPTB was injected into one side of substantia nigra of GFAP-Cre mice between P30 and P40, a developmental stage when astrocytes are known to have already lost their neurosphere-generating potential in the midbrain. As a negative control, similar injections were performed with a vector encoding only RFP (AAV-Empty). In the AAV-Empty injected group, as expected, most RFP positive cells were GFAP positive, but NeuN negative, indicating that none of transduced astrocytes were converted to neurons (FIG. 7B, top left two panels). In contrast, by 3 weeks post-injection of AAV-shPTB, while most transduced cells remained GFAP positive and had typical astrocytic morphology, ~20% of RFP positive cells started to express the mature neuron marker NeuN and the percentage of these RFP-labeled NeuN positive cells increased dramatically by 5 weeks (FIGS. 8B and 8C). By 10 weeks, >80% RFP-positive cells became NeuN positive and no longer expressed detectable GFAP (FIG. 7B, bottom left two panels, quantified on the right). These data indicate that RFP-positive cells were gradually converted to neurons in the midbrain.

The converted neurons were examined by immunostaining with a series of neuronal markers, including Tuj1, MAP2, NSE and PSD-95. Most of the converted neurons expressed all four of these markers 10 weeks after the AAV-shPTB delivery (FIG. 7C). Staining for PSD-95, a membrane-associated guanylate kinase present in the postsynaptic membrane, showed the typical punctate pattern in NeuN/RFP-double positive cells. Notably, in contrast to the results for in vitro astrocyte-to-neurons conversion (see FIG. 5C), a substantial portion of RFP-positive neurons (30 to 35%) were stained positively for tyrosine hydroxylase (TH), a typical marker of dopaminergic neurons (FIG. 7D), whereas glutamatergic and GABAergic neurons were detectable at relatively lower levels (FIG. 8E). Most of the converted cells also expressed Girk2, a marker of A9 dopaminergic neurons (FIG. 8F), while a minor population was positively stained for calbindin-D28k, a marker of A10 dopaminergic neurons (FIG. 8G). These findings suggest regional specificity in trans-differentiation of astrocytes into different neuronal subtypes.

To further explore the region specificity in neuronal subtype induction, conversion of astrocytes from cortex was compared versus midbrain in vitro. It was found that midbrain-derived astrocytes converted at a much higher efficiency (8 to 10%) into TH-positive neurons when compared to cortex-derived astrocytes (with only a 1-2% conversion), as determined both by immunostaining and immunoblotting (FIGS. 6E-G). These data are consistent with the present disclosure's recognition that, in certain instances, astrocytes from different brain regions can exhibit different gene expression programs, suggesting the presence of regionally distinct types of astrocytes in the brain.

The subtypes of neurons converted from astrocytes from different parts of mouse brain were then investigated. It was found that midbrain astrocytes, but not those from cortex or striatum were efficiently trans-differentiated into TH-positive neurons in vivo, although all were converted to NeuN-positive neuron in a similarly high (~80%) efficiency (FIGS. 7E-G). The near absence of astrocyte-derived TH-positive neurons in the striatum is striking, as this is the region innervated by the axons of nigral dopaminergic neurons. The higher percentage of astrocyte-derived TH-positive neurons converted in vivo (~35%) compared to that in vitro (~10%) suggests that local environmental cues may further enhance converted neurons to develop into specific subtypes in different brain regions. These findings are in line with the present disclosure's recognition that astrocytes from midbrain, but not other brain regions, promote differentiation from neuronal stem cells to dopaminergic neurons.

Example 5. Astrocyte-Converted Neurons were Functional as Characterized in Brain Slices To functionally characterize astrocyte-converted neurons in situ, electrophysiological studies were performed on brain slices 5-6 weeks after transduction with AAV-shPTB. RFP-positive neurons were injected the fluorescent dye Neurobiotin 488 to mark cells from which patch clamp recordings were taken, and the dopaminergic subtype of patched cells was confirmed by TH staining after recording (FIG. 7H). Typical voltage-dependent currents of Na+ and K+ channels were detected (FIG. 7I). These neurons also showed the capability to fire repetitive action potentials (FIG. 7J) and exhibited spontaneous postsynaptic currents (FIG. 7K). These data suggest that astrocyte-converted TH-positive neurons are functional and suggest that they are incorporated into neural circuits.

Figure 9G:
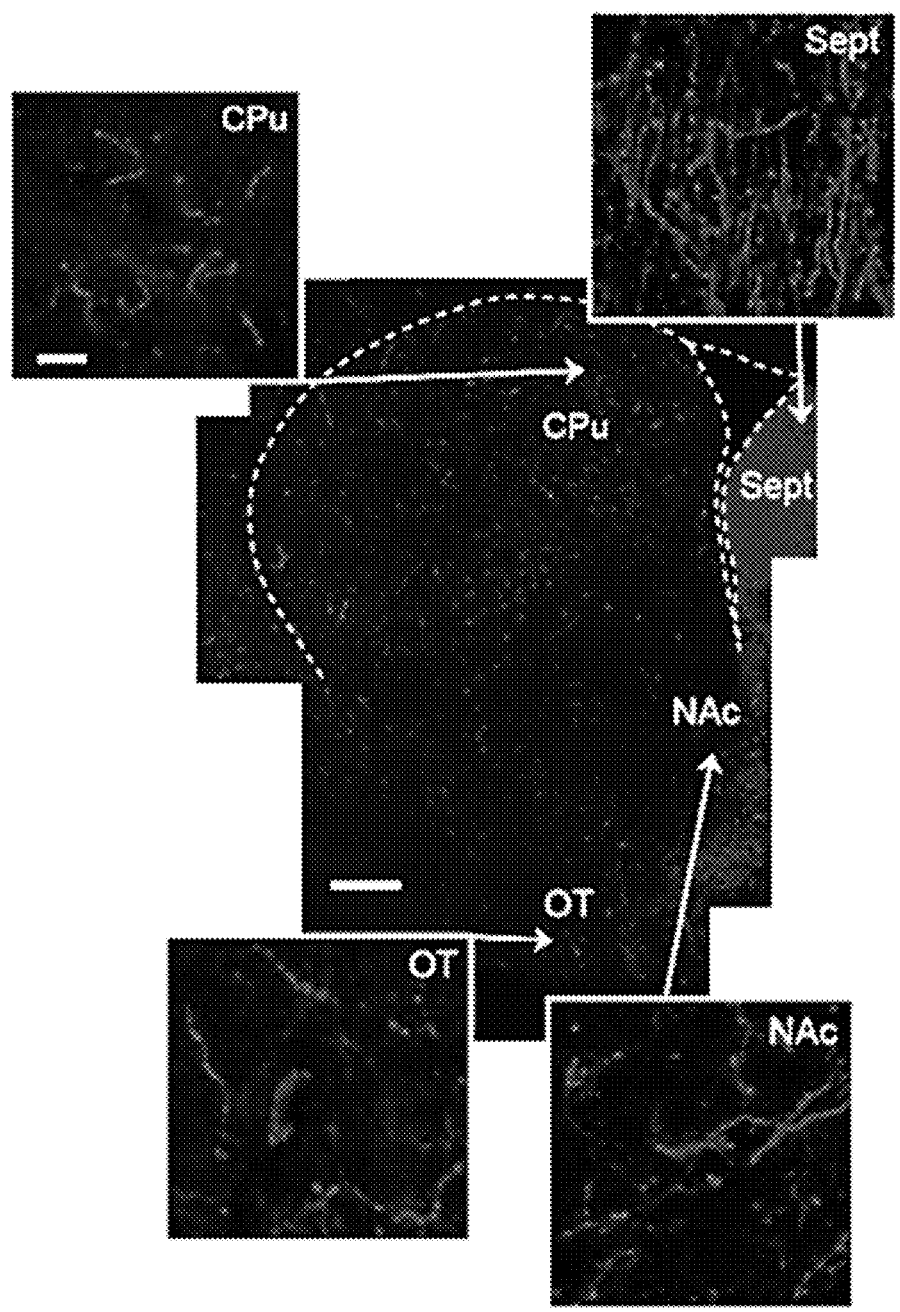
Figure 10:
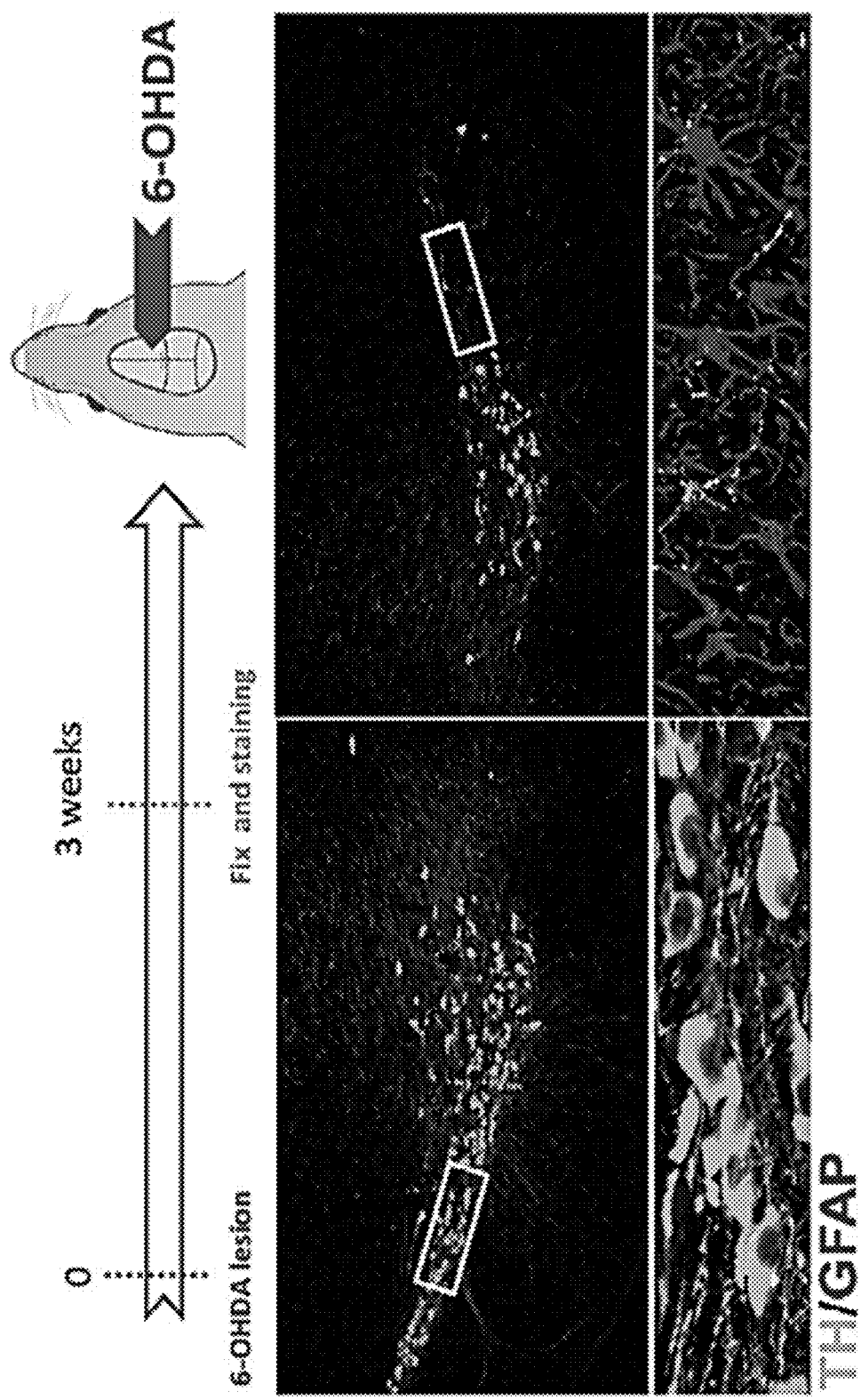
FIG. 10 illustrates construction of a mouse model of Parkinson's disease. Top panel shows a timeline of injection of 6-OHDA into substantial nigra of a mouse followed by fixation and staining of the mouse brain. Bottom fluorescent images show immunostaining results of striatum from a mouse that received no 6-OHDA injection (left) and striatum from a mouse that received 6-OHDA injection (right). Comparison between left and right images demonstrates loss of TH-positive fiber bundle and increase in GFAP-positive astrocytes along the lesioned fiber bundle after 6-OHDA injection.

Example 6. Integration of Midbrain Astrocyte-Derived Neurons into the Nigrostriatal Pathway Quantitative analysis revealed that ~4000 total RFP-positive cells gave rise to ~1300 TH-positive neurons within substantia nigra (FIGS. 8H-J). Subtype specificities of these reprogrammed neurons were further confirmed by immunostaining for the dopamine transporter (DAT), the vesicular monoamine transporter 2 (VMAT2), as well as specific markers for midbrain dopaminergic neurons, such as engrailed homeobox 1 (En1) and LIM homeobox transcription factor 1 alpha (Lmx1a) on brain slices (FIG. 9B). While RFP-positive cell bodies were only present in the substantia nigra, RFP-positive fibers were detected in the caudate-putamen as well as other target fields, including nucleus accumbens, septum and the olfactory tubercle (FIGS. 9A and 9G), as observed in earlier studies in which the mouse midbrain was grafted with neuronal stem cells. A fraction of these fibers were also TH-positive (FIG. 9H). Quantification of fiber density revealed that RFP/TH-double positive processes were mainly distributed in the caudate-putamen (CPu) and nucleus accumbens (NAc) regions of the striatum (FIG. 9I), despite the presence of a lot more (~3-fold) RFP-positive fibers in septum (Sept) (see also FIG. 9G). These data support the possibility that environmental cue in the nigrostriatal pathway impact the pattern of innervation by astrocyte-converted neurons.

To further demonstrate that axons of newly converted neurons extended to the striatum, fluorescent retrograde axonal tracing beads were injected into the caudate putamen of mice 10 weeks after the AAV-shPTB delivery (FIG. 9E). One day after injecting retrobeads, both endogenous TH-positive cells and converted TH/RFP-double positive cells within the substantia nigra were detected that were retrogradely labeled with green beads (arrows in FIG. 9F). Taken together, these data demonstrate that injection of AAV-shPTB into midbrain astrocytes can result in reprogramming and conversion into functional dopaminergic neurons.

Example 7. Replenishing Lost Dopaminergic Neurons in the Nigrostriatal Pathway

The numbers of astrocytes converted to dopaminergic neurons and the relatively robust growth of their axons to striatum suggested that PTB-mediated astrocyte-converted neurons might be able to reconstitute an injured nigrostriatal pathway. To explore this possibility, degeneration of dopaminergic neurons was induced through unilateral injection of 6-hydroxydopamine (6-OHDA), a dopamine analog toxic to dopaminergic neurons, into the medial forebrain bundle (FIG. 11A). As expected, one month after 6-OHDA injection, unilateral loss of TH-positive cell bodies was observed in the midbrain and striatal denervation (FIG. 11B). Accompanying the loss of dopaminergic neurons in the lesioned nigra was a dramatically increased population of GFAP-positive astrocytes (FIG. 11C), indicative of an expected reactive astrocytic response.

One month after unilateral lesion with 6-OHDA, AAV-shPTB or AAV-Empty was injected into the midbrain. Examination of the lesioned substantia nigra 10 weeks after injection o AAV-shPTB, but not AAV-Empty, showed an increased number of TH-positive neurons, a fraction of which were also RFP-positive (FIGS. 11D-I). Neuronal counting revealed that the initial ~4500 TH-positive neuronal cell bodies seen in the unlesioned substantia nigra were reduced more than 90% (to ~400) in the lesioned side.

Importantly, AAV-PTB administration induced ~1000 new RFP/TH-double positive neurons (FIG. 11J), thereby restoring TH-positive neurons to ~⅓ of the initial number.

A substantial amount of RFP-positive fibers were also detected in the striatum and along the nigrostriatal pathway, a fraction of which was also positive for TH (FIG. 11E, FIGS. 17A-F). Quantitative analysis of fiber density indicated that 6-OHDA reduced TH-positive fibers to ~15% of the initial level, with AAV-PTB restoring TH-positive fibers to ~40% of wild-type levels detected in the unlesioned side (FIG. 11L). By quantifying RFP-positive and RFP/TH-double positive fibers in different striatum regions, it was determined that the caudate-putamen (CPu) region contained the highest proportion of RFP/TH-double positive fibers (FIG. 11K). Although a similar, partially reconstituted nigrostriatal pathway has been achieved with transplantation of stem cell-derived dopaminergic neurons in mouse brain, these data show that, without any additional treatment to specify neuronal subtypes, AAV-shPTB can induce new neurons converted from endogenous midbrain astrocytes to replenish lost dopaminergic neurons.

Example 8. Reversal of Parkinson Disease Phenotype by Direct Reprogramming in Midbrain To determine the ability of the reconstituted nigrostriatal pathway to restore circuit function, it was examined whether or not AAV-shPTB transduced mice would show improved motor function following unilateral 6-OHDA lesion. Three standard behavior tests were performed, two based on drug-induced rotation and the third on spontaneous motor activities. Both contralateral rotations induced by apomorphine and ipsilateral rotation triggered by amphetamine were markedly increased following 6-OHDA induced lesion. Remarkably, both of these phenotypes were restored to nearly wild-type levels 3 months after AAV-shPTB treatment, while no significant corrections were recorded in AAV-Empty transduced mice (FIG. 12A). The time course of apomorphine-induced rotations with the same set of mice showed progressive phenotypic recovery in 2 to 3 months (FIG. 12B).

To examine spontaneous motor activity, the cylinder test was performed to score limb use bias. Unlesioned mice used both limbs with relatively equal frequency, while unilaterally lesioned mice showed preferential ipsilateral touches, indicating disabled contralateral forelimb function. In AAV-shPTB transduced mice, a dramatic, time-dependent improvement for forelimb use was observed, reaching wild-type levels of performance by 3 months post treatment, while AAV-Empty transduced mice failed to show any improvement (FIG. 12C).

To test if the reprogrammed neurons were directly responsible for the restoration of normal motor function, a chemogenetic approach was taken by expressing the inhibitory hM4Di receptor (in place of RFP in the AAV-shPTB vector) in the converted neurons (FIG. 16A). It is well established that the action potential of neurons expressing the hM4Di receptor is potently inhibited by clozapine-N-oxide (CNO), a drug that is metabolized within 1 to 2 days after injection. The restoration of motor performance in 6-OHDA-treated mice, as measured with the cylinder assay, was eliminated after intraperitoneal injection of CNO, with the phenotype re-appearing within 40 min of injection. Injection of CNO into unlesioned mice had no effect. Remarkably, and correlating with metabolism of the drug, the motor phenotype again disappeared within 3 days (FIG. 16B). These results demonstrated that the astrocyte-converted neurons can be directly responsible for motor recovery.

Example 9. Restoration of Striatal Dopamine in Reprogrammed Brain

Extracts from the striatum were prepared for HPLC analysis of dopamine in both unlesioned sides in comparison with the lesioned side with or without AAV-shPTB mediated astrocyte conversion. To identify the dopamine signal, known amounts in the range of normal dopamine levels were spiked in to the striatum lysate. It was shown the signal was linearly correlated with the amount added (FIGS. 15A and 15B). Next, the levels of dopamine were measured in the striatum under different conditions, and showed effective ablation of dopamine in 6-OHDA lesioned mice, but significant restoration of dopamine in AVV-shPTB reprogrammed mice (FIGS. 15C-15F). Quantification of the results based on 3 independent experiments demonstrated that relative to the unlesioned striatum, the level of dopamine was elevated from ~25% in the lesioned striatum to 65% upon AAV-shPTB treatment (FIG. 6F). This ~40% net gain in dopamine biogenesis is within the range of 30 to 35% recovery of RFP/TH-double positive cell bodies in nigra and processes in striatum, suggesting that AAV-shPTB reprogrammed neurons can be responsible for the observed phenotypic recovery.

Example 10. Antisense Oligonucleotide Against PTB mRNA Induced Neuronal Conversion and Rescued Chemically Induced Parkinson's Disease Phenotype Five 21-nucleotidebase antisense oligonucleotide (ASO) targeting PTB (PTB-ASO) that contained a phosphorothioate backbone (to increase overall stability and aid with delivery) with a 3' fluorescein (to allow tracing of the injected ASO) was synthesized. An ASO targeting GFP (GFP-ASO) was also synthesized as a negative control. Three of the PTB-ASOs, but not GFP-ASO, was effective in reducing PTB expression upon transfection into isolated mouse astrocytes (FIG. 13A). Five weeks after introduction of PTB-ASO of the PTB-ASO with the highest targeting efficiency (#4), mouse astrocytes cultured in standard neuronal differentiation medium showed synthesis of a series of neuronal markers, including Tuj1, MAP2, NSE and NeuN, while astrocytes transfected with the control ASO did not (FIG. 13B), and thus converted neurons remained healthy neuronal morphology for at least 3 months, the longest period that was tested (data not shown). Similar to the AAV-shPTB viral vector, a small fraction of converted neurons were dopaminergic, as indicated by positive TH staining (FIG. 13B).

The PTB-ASO was shown to induce neuronal conversion in vivo in the midbrain of mice, which carry both the GFAP-CreER™ transgene (inducible by treatment with tamoxifen) and a tdTomato encoding transgene (integrated at the Rosa26 locus) whose expression is permanently activated by the action of the Cre recombinase. Treatment of the resultant doubly transgenic mice with tamoxifen induced Cre to activate TdTomato in astrocytes of these mice. Cre was systematically induced at postnatal day 35 (P35) (FIG. 14A), and 3 weeks later, ASOs were unilaterally sterotactically injected into the substantia nigra of these mice. Without injecting ASOs, all tdTomato-labeled cells were NeuN negative, while most of those cells were GFAP positive (FIG. 14B). However, by 2 months after PTB-ASO injection, a portion of tdTomato-labeled cells became NeuN positive (FIG. 14C), some of which were also TH positive (FIG. 14D). Significantly, 6-OHDA-treated mice injected with the PTB-ASO showed apomorphine-induced rotations that were dramatically reduced by 3 months post treatment, whereas the control GFP-ASO showed no rescue effects (FIG. 13C). These findings potentiate the possibility of treating neurodegenerative disorders, including PD, with oligonucleotide-based (ASO or RNAi) therapeutics.

Example 11. Materials and Methods

This example describes several methods utilized for Examples 1-10.

Vectors and Virus Production

To build the lentiviral vector to express shPTB in mouse astrocytes, the target sequence (5'-GGGTGAA-GATCCTGTTCAATA-3'; SEQ ID NO: 1) was shuttled to the pLKO.1-Hygromycin vector (Addgene, #24150). For human astrocytes, a similar vector containing target sequence (5'-GCGTGAAGATCCTGTTCAATA-3'; SEQ ID NO: 2) was used. Viral particles were packaged in Lenti-X 293T cells (Clontech) with two package plasmids: pCMV-VSV-G (Addgene, #8454) and pCMV-dR8.2 dvpr (Addgene, #8455). Viral particles were concentrated by ultracentrifugation on a Beckman XL-90 centrifuge with SW-28 rotor.

To construct AAV vectors, the same target sequence against mouse PTB was first inserted into the pTRIPZ-RFP vector between EcoR I and Xho I sites. The segment containing RFP and shRNA was next sub-cloned to replace CaMP3.0 in AAV-CMV-LOX-STOP-LOX-mG-CaMP3.0 vector (Addgene, #50022) by using Asc I. To construct a control vector, a similar segment containing only RFP was cloned into the AAV-CMV-LOX-STOP-LOX-mG-CaMP3.0 vector. The resulting vectors were referred to as AAV-shPTB or AAV-Empty. The AAV-hM4Di-shPTB vector was constructed by replacing RFP in AAV-shPTB with the cDNA of hM4Di, which was sub-cloned from pAAV-CBA-DIO-hM4Di-mCherry vector (Addgene, #81008).

Viral particles of AAV2 were packaged in transfected 293T cells with other two plasmids: pAAV-RC and pAAV-Helper (Agilent Genomics). After harvest, viral particles were purified with heparin column (GE HEALTHCARE BIOSCIENCES) and then concentrated with Ultra-4 centrifugal filter units (Amicon, 100,000 molecular weight cutoff). Titers of viral particles were determined by qPCR to be $>1\times10^{12}$ particles/ml.

Synthesis of Antisense Oligonucleotides

Antisense oligonucleotides were synthesized from Integrated DNA Technologies. The sequence of ASO targeting mouse PTB (ASO-mPTB) was 5'-GGGTGAA-GATCCTGTTCAATA-3' (SEQ ID NO: 1). An ASO targeting Turbo GFP (5'-GTTGGTGCTCTTCATCTTGTT-3') (SEQ ID NO: 3) was synthesized as a control. The backbones of all ASOs contain phosphorothioate modifications. Fluorescein (FAM) was attached to 3' end of those ASOs for fluorescence detection.

Western Blot and RT-PCR

For analysis by western blotting, cells were lysed in 1×SDS loading buffer, and after quantification, bromophenol blue was added to a final concentration of 0.1%. 25~30 ug of total proteins were resolved in 10% Nupage Bis-Tris gel and probed with following antibodies: Rabbit anti-PTBP1 (kindly provided by Douglas Black, 1:3000), Mouse anti-PTBP2 (Santa Cruz, sc-376316, 1:1000), Mouse anti-beta actin (Sigma, A2228, 1:10000), Rabbit anti-Tuj1 (Covance, MRB-435P, 1:10000), Rabbit anti-Brn2 (Cell Signaling, 12137, 1:1000), Chicken anti-TH (Aves lab, TYH, 1:1000) and Rabbit anti-VMAT2 (Proteintech, 20873-1-AP, 1:500).

For RT-qPCR analysis, RNA was extract with Trizol (Life Technology) and 10 ug/ml of Glycogen was used to enhance precipitation of small RNAs. Total RNA was first treated with DNase I (Promega) followed by reverse transcription with miScript II RT Kit (QIAGEN, 218160). RT-qPCR was performed using the miScript SYBR Green PCR Kit (QIAGEN, 218073) on a step-one plus PCR machine (Applied Biosystems). The primers used were U6-F: 5'-ACGCAAAT-TCGTGAAGCGTT-3' (SEQ ID NO: 4); miR-124-F: 5'-TAAGGCACGCGGTGAATGCC-3' (SEQ ID NO: 5); and miR-9-F: 5'-GCGCTCTTTGGTTATCTAGCTGTATG-3' (SEQ ID NO: 6).

Cell Culture and Trans-Differentiation In Vitro

Mouse astrocytes were isolated from postnatal (P4~P5) pups. The cortical tissue was dissected from whole brain and incubated with Trypsin before plating onto dishes coated with Poly-D-lysine (Sigma). Isolated astrocytes were cultured in DMEM (GIBCO) plus 10% fetal bovine serum (FBS) and penicillin/streptomycin (GIBCO). Dishes were carefully shaken daily to eliminate non-astrocytic cells. After reaching ~90% confluence, astrocytes were disassociated with Accutase (Innovative Cell Technologies) followed by centrifugation for 3 min at 800 rpm, and then cultured in medium containing DMEM/F12 (GIBCO), 10% FBS (GIBCO), penicillin/streptomycin (GIBCO), B27 (GIBCO), 10 ng/ml epidermal growth factor (EGF, PeproTech), and 10 ng/ml fibroblast growth factor 2 (FGF2, PeproTech).

To induce trans-differentiation in vitro, mouse astrocytes were re-suspended with astrocyte culture medium containing the lentivirus that targets mouse PTB, and then plated on Matrigel Matrix (Corning)-coated coverslips (12 mm). After 24 hrs, cells were selected with hygromycin B (100 ug/ml, Invitrogen) in fresh astrocyte culture medium for 72 hrs. The medium was next switched to the N3/basal medium (1:1 mix of DMEM/F12 and Neurobasal, 25 µg/ml insulin, 50 µg/ml transferring, 30 nM sodium selenite, 20 nM progesterone, 100 nM putrescine) supplemented with 0.4% B27, 2% FBS, a cocktail of 3 small molecules (1 uM ChIR99021, 10 uM SB431542 and 1 mM Db-cAMP), and neurotrophic factors (BDNF, GDNF, NT3 and CNTF, all in 10 ng/ml). The medium was half-changed every the other day. To measure synaptic currents, converted cells after 6 weeks were added with fresh GFP-labeled rat astrocytes, and after further 3 to 4 weeks of co-culture, patch-clamp recordings were performed.

Human astrocytes were purchased from a commercial source (ScienCell). Cells were grown in Astrocyte Medium (ScienCell) and sub-cultured until reaching ~80% confluence. For trans-differentiation in vitro, cultured human astrocytes were first disassociated with Trypsin; re-suspended in Astrocyte Medium containing the lentivirus that targets human PTB; and plated on Matrigel Matrix-coated coverslips. After 24 hrs, cells were selected with hygromycin B (100 ug/ml, Invitrogen) for 72 hrs. The medium was switched to the N3/basal medium supplemented with 0.4% B27, 2% FBS and neurotrophic factors (BDNF, GDNF, NT3 and CNTF, all in 10 ng/ml). To measure synaptic currents, converted cells after 3 weeks were added with fresh GFP-labeled rat astrocytes, and after further 2 to 3 weeks of co-culture, patch-clamp recordings were performed.

Immunocytochemistry.

Cultured cells grown on glass slides were fixed with 4% Paraformaldehyde (Affymetrix) for 15 min at room temperature followed by permeabilization with 0.1% Triton X-100 in PBS for 15 min on ice. After washing twice with PBS, cells were blocked in PBS containing 3% BSA for 1 hr at room temperature. The fixed cells were incubated with primary antibodies overnight at 4° C. in PBS containing 3% BSA. After washing twice with PBS, the cells were incubated with secondary antibodies conjugated to Alexa Fluor 488, Alexa 546, Alexa 594 or Alexa 647 (1:500, Molecular Probes) for 1 hr. 300 nM DAPI in PBS was applied to the cells for 20 min at room temperature to label nuclei. After additional washing three times with PBS, Fluoromount-G mounting media was applied onto the glass slides, and images were examined and recorded under Olympus FluoView FV1000.

For staining brain sections, mice were sacrificed with CO2 and immediately perfused, first with 15-20 mL saline (0.9% NaCl) and then with 15 mL 4% paraformaldehyde (PFA) in PBS to fix tissues. Whole brains were extracted and fixed in 4% PFA overnight at 4° C., and then cut to 14~18 um sections by a cryostat (Leica). Before staining, brain sections were incubated with sodium citrate buffer (10 mM Sodium citrate, 0.05% Tween 20, pH 6.0) for 15 min at 95° C. for antigen retrieval. The slides were next treated with 5% normal donkey serum and 0.3% Triton X-100 in PBS for 1 hr at room temperature. The rest of steps were performed as on cultured cells.

The following primary antibodies were used: Rabbit anti-Tuj1 (Covance, MRB-435P, 1:1,000), Mouse anti-Tuj1 (Covance, MMS-435P, 1:1,000), Mouse anti-MAP2 (Milipore, MAB3418, 1:1000), Mouse anti-NeuN (Milipore, MAB377, 1:200), Chicken anti-NSE (Ayes lab, NSE, 1:1000), Rabbit anti-VGlut1 (Synaptic Systems, 135-303, 1:200), Rabbit anti-GAD67 (Cell Signaling, 63080, 1:200), Chicken anti-TH (Aves lab, TYH, 1:1000), Rabbit anti-PSD95 (Cell Signaling, 3450, 1:200), Rabbit anti-DAT (Bioss, bs-1714R, 1:100), Goat anti-VMAT2 (Everest biotech, EB06558, 1:100), Rabbit anti-En1 (Abgent, AP7278a, 1:100), Rabbit anti-Lmx1a (ProSci, 7087, 1:100), Rabbit anti-GFAP (Cell Signaling, 12389, 1:200), Chicken anti-GFAP (Aves lab, GFAP, 1:100), Rabbit anti-ALDH1L1 (EnCor Biotechnology, RPCA-ALDH1L1, 1:2000), Mouse anti-OLIG2 (Santa Cruz, sc-293163, 1:100), Chicken anti-CD11b (Aves lab, MAC, 1:1000), Mouse anti-NG2 (Santa Cruz, sc-53389, 1:100), Mouse anti-Nestin (Cell Signaling, 4760, 1:200), Mouse anti-NANOG (Santa Cruz, sc-293121, 1:100), Mouse anti-Fibronectin (DSHB, 1H9, 1:500), Rabbit anti-GAD65 (Cell Signaling, 5843, 1:50), Rabbit anti-VGlut2 (Bioss, bs-9686R, 1:100), Rabbit anti Girk2 (Proteintech, 21647-1-AP, 1:100), Rabbit anti Calbindin D28K (Proteintech, 14479-1-AP, 1:100) and Mouse anti-RFP (ThermoFisher, MA5-15257, 1:200).

Quantification of Neuronal Cell Body and Fiber Density.

Coronal sections across the midbrain were sampled at intervals of 120-140 um for immunostaining of TH and RFP. The total numbers (Nt) of cell types of interest were calculated using the formula of Nt=Ns*(St/Ss) in which Ns is the number of neurons counted, St is the total number of sections in the brain region, and Ss is the number of sections sampled, as previously described. RFP-positive and RFP/TH-double positive fibers were quantified using a previously published method. Three coronal sections (A/P+1.3, +1.0 and +0.70) were selected from each brain for analysis. For each selected section, three randomly chosen areas were captured from one section of z-stack images at intervals of 1 μm using a 60× oil-immersion objective. A sphere (diameter: 14 μm) was then generated as a probe to measure fiber density within the whole z-stack. Each fiber crossing the surface of sphere was given one score. The optical density of striatal TH fibers was determined from same sections. The digitalized image of sampled section was captured with a 10× objective and analyzed by Image-J 1.47v (Wayne Rasband, Bethesda, Md.).

Electrophysiology.

Patch clamp recordings were performed with Axopatch-1D amplifiers or Axopatch 200B amplifier (Axon Instruments) connecting to a Digidata1440A interface (Axon Instruments). Data were acquired with pClamp 10.0 or Igor 4.04 software and analyzed with MatLab v2009b. For converted neurons from mouse astrocytes in vitro, small molecules were removed from medium 1 week before patch clamp recording. Both cultured mouse and human cells were first incubated with oxygenated (95% $O_2$/5% $CO_2$) artificial cerebrospinal fluid (150 mM NaCl, 5 mM KCl, 1 mM $CaCl_2$, 2 mM $MgCl_2$, 10 mM glucose, 10 mM HEPES, pH 7.4) at 37° C. for 30 min and whole-cell patch clamp was performed on selected cells.

For recording activities of converted neurons in vivo, cortical slices (300 μm) were prepared 6-8 weeks after injections of AAV vectors. The slices were cut with a vibratome in oxygenized (95% $O_2$/5% $CO_2$) dissection buffer (110.0 mM choline chloride, 25.0 mM $NaHCO_3$, 1.25 mM $NaH_2PO_4$, 2.5 mM KCl, 0.5 mM $CaCl_2$, 7.0 mM $MgCl_2$, 25.0 mM glucose, 11.6 mM ascorbic acid, 3.1 mM pyruvic acid) at 4° C. followed by incubation in oxygenated ACSF (124 mM NaCl, 3 mM KCl, 1.2 mM $NaH_2PO_4$, 26 mM $NaHCO_3$, 2.4 mM $CaCl_2$, 1.3 mM $MgSO_4$, 10 mM dextrose and 5 mM HEPES; pH 7.4) at room temperature for 1 hr before experiments.

Patch pipettes (5-8 MΩ) solution contained 150 mM KCl, 5 mM NaCl, 1 mM $MgCl_2$, 2 mM ethylene glycol tetra acetic acid (EGTA)-Na, and 10 mM Hepes pH 7.2. For voltage-clamp experiments, the membrane potential was typically held at −75 mV. The following concentrations of channel blockers were used: PiTX: 50 uM; NBQX: 20 uM; APV: 50 uM. All of these blockers were bath-applied following dilution into the external solution from concentrated stock solutions. All experiments were performed at room temperature.

Construction of Mouse Models.

The GFAP-Cre transgenic mouse (B6.Cg-Tg(Gfap-cre)77.6Mvs/2J) was used in AAV-shPTB induced in vivo reprogramming experiments. For testing the effect of ASOs in vivo, the GFAP-CreER™ mouse (B6.Cg-Tg(GFAP-cre/ERT2)505Fmv/J) was crossed with the Rosa-tdTomato mouse (B6.Cg-Gt(ROSA)26Sortm14(CAG-tdTomato)Hze/J). The offsprings of these double GFAP-CreER'; Rosa-tdTomato transgenic mice aged postnatal 35 days were injected with tamoxifen (dissolved in corn oil at a concentration of 20 mg/ml) via intraperitoneal injection once every 24 hrs for a total of 5 consecutive days. The dose of each injection was 75 mg/kg. Two weeks after tamoxifen application, PTB-ASO or control ASO was injected into the substantia nigra of those mice to investigate ASO-induced in vivo reprogramming and behavior benefits. All transgenic mice were purchased from The Jackson Laboratory.

Ipsilateral Lesion with 6-OHDA and Stereotaxic Injections.

Adult WT and GFAP-Cre mice at the age of postnatal day 40 were used to perform surgery to induce lesion. Animals were first anaesthetized with a mix of ketamine (80-100 mg/kg) and xylazine (8-10 mg/kg) and then placed in a stereotaxic mouse frame. Before injecting 6-hydroxydopamine (6-OHDA, Sigma), mice were first treated with a mix of desipramine (25 mg/kg) and pargyline (5 mg/kg). 6-OHDA was dissolved in 0.02% ice-cold ascorbate/saline solution at a concentration of 15 mg/ml and used within 3 hrs. The toxic solution was injected into the medial forebrain bundle (MFB) at the following coordinates (relative to bregma): anterior-posterior (A/P)=−1.2 mm; medio-lateral (M/L)=−1.3 mm and dorso-ventral (D/V)=−4.75 mm (from the dura). Injections were applied in a 5 ul Hamilton syringe with a 33 G needle at the speed of 0.1 ul/min for 3 min before slowly removing the needle. Cleaning and suturing of the wound were performed after lesion.

AAV vectors or ASOs were injected into the substantia nigra ~30 days after 6-OHDA induced lesion. 4 ul of AAV vectors or 2 ul of ASOs (1 ug/ul) were injected into lesioned nigra at the following coordinates A/P=−3.0 mm; M/L=−1.2 mm and D/V=−4.5 mm. Injections were made using same syringe and needle, at a rate of 0.5 ul/min for 3 min before slowly removing the needle.

Retrograde Tracing.

For retrograde tracing of nigrostriatal pathway, GFAP-Cre mice with or without 6-OHDA induced lesion were first injected with AAV-shPTB vectors. 3 months after the AAV delivery, green Retrobeads IX (Lumafluor, Naples, Fla.) were unilaterally injected at two sites into the striatum on the same side of AAV injection, using following two coordinates: A/P=+0.5 mm, M/L=+2.0 mm, D/V=+3.0 mm and A/P=+1.2 mm, M/L=+2.0 mm, D/V=+3.0 mm. ~2 ul of beads were injected. After 24 hrs, animals were sacrificed and immediately perfused. Their brains were fixed with 4% PFA for sectioning and immunostaining.

Measurement of Striatal Dopamine.

Dopamine levels in mouse striatum were measured by Reverse-phase High-performance Liquid Chromatography (HPLC). The HPLC analysis was performed using an Agilent 1260 Infinity HPLC system with an Agilent Zorbax SB-C18 semi-prep column (ID 9.4×250 mm, 5 μm, 80 Å) using a water/methanol gradient containing 0.1% formic acid. Each substance is characterized by retention time and 260 nm absorbance under Variable Wavelength Detector (VWD), as previously described. The striatal samples were directly prepared from brain tissue. Briefly, striatal dissection was carried out immediately after euthanization of the mouse. After homogenized in 200 μL of 0.1M hydrochloric acid with a squisher, the sample was centrifuged (12,000×g, 10 min, 4° C.). The resulting supernatant was filtered by a 0.2 um Nanosep MF centrifugal device and then applied to HPLC analysis.

Behavioral Testing.

All behavioral tests were carried out 21-28 days after 6-OHDA induced lesion or 2, 3, and 5 months after the delivery of AAV vectors or ASOs. For rotation test, apomorphine-induced rotations in mice were recorded after intraperitoneal injection of apomorphine (Sigma, 0.5 mg/kg) under a live video system. Mice were injected with apomorphine (0.5 mg/kg) on two separate days prior to performing the rotation test (for example, if the test was to be performed on Friday, the mouse would be first injected on Monday and Wednesday), which aimed to prevent a 'wind-up' effect that could obscure the final results. Rotation was measured 5 min following the injection for 10 min periods as previously described and only full-body turns were counted. Data are expressed as net contralateral turns per min. For cylinder test, mice were individually placed into a glass cylinder (diameter 19 cm, height 25 cm), with mirrors placed behind for a full view of all touches, as described. Mice were recorded under a live video system for 5 min. No habituation of the mice to the cylinder was performed before the recording. A frame-by-frame video player (KMPlayer version 4.0.7.1) was used for scoring. Only wall touches independently with the ipsilateral or the contralateral forelimb were counted. Simultaneous wall touches (touched executed with both paws at the same time) were not included in the analysis. Data are expressed as a percentage of ipsilateral touches in total touches.

For chemogenetic experiment, cylinder tests were carried out 21-28 days after 6-OHDA induced lesion and 2 months after the delivery of AAV-hM4Di-shPTB. In the later test, animal was firstly injected with saline to record the baseline of recovery. Subsequent recording was performed 40 min after Intraperitoneal injection of CNO (Biomol International, 4 mg/kg) or 72 hrs after metabolism of the drug.

Example 12. Protein or Nucleic Acid Sequences

TABLE 1

Protein or nucleic acid sequences

| Name | Sequence (5' to 3') | SEQ ID NO |
| --- | --- | --- |
| Target sequence of mouse PTB | GGGTGAAGATCCTGTTCAATA | 1 |
| Target sequence of human PTB | GCGTGAAGATCCTGTTCAATA | 2 |
| ASO targeting Turbo GFP | GTTGGTGCTCTTCATCTTGTT | 3 |
| U6-F primer | ACGCAAATTCGTGAAGCGTT | 4 |
| miR-124-F primer | TAAGGCACGCGGTGAATGCC | 5 |
| miR-9-F primer | GCGCTCTTTGGTTATCTAGCTGTATG | 6 |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

What is claimed is:

1. A method of reprogramming a human glial cell to a mature neuron, comprising:
   injecting a single composition into a midbrain comprising the human glial cell, wherein the single composition comprises an antisense nucleic acid sequence that:
   (i) has between 15 and 35 nucleotides;
   (ii) binds a gene encoding polypyrimidine-tract-binding protein (PTB); and
   (iii) is effective to suppress expression or activity of the PTB in the human glial cell, wherein, prior to the injecting, the human glial cell exhibits Brn2 or miR-9 level that is higher than that of a human adult fibroblast, and
   wherein the injecting the single composition is sufficient to effect an increased expression level of neural polypyrimidine-tract-binding protein (nPTB) and subsequently a decreased expression level of the nPTB in the human glial cell, thereby promoting the reprogramming of the human glial cell to the mature neuron.

2. The method of claim 1, wherein the human glial cell exhibits the expression level of the Brn2 or the miR-9 that is at least 1.2 times higher than that of the human adult fibroblast.

3. The method of claim 2, wherein the human glial cell exhibits the expression level of the Brn2 or the miR-9 that is at least 5 times higher than that of the human adult fibroblast.

4. The method of claim 3, wherein the human glial cell exhibits the expression level of the Brn2 or the miR-9 that is at least 10 times higher than that of the human adult fibroblast.

5. The method of claim 1, wherein the antisense nucleic acid sequence is an antisense oligonucleotide.

6. The method of claim 5, wherein the antisense oligonucleotide is identical to the nucleotide sequence of SEQ ID NO: 1.

7. The method of claim 5, wherein the antisense oligonucleotide is identical to the nucleotide sequence of SEQ ID NO: 2.

8. The method of claim 1, wherein the single composition comprises a viral vector encoding the antisense nucleic acid sequence.

9. The method of claim 1, wherein the midbrain is lesioned, and wherein the contact effects restoration of at least a portion of a function of the lesioned brained region.

10. The method of claim 1, wherein the contact effects at least 20% increase in dopamine level in the midbrain.

11. The method of claim 1, wherein the human glial cell exhibits the expression levels of the Brn2 that is higher than that of the human adult fibroblast.

12. The method of claim 1, wherein the human glial cell exhibits the expression levels of the miR-9 that is higher than that of the human adult fibroblast.

13. The method of claim 1, wherein prior to the injecting, the human glial cell exhibits the expression levels of Brn2 and miR-9 that are higher than those of the human adult fibroblast.

14. The method of claim 1, wherein the single composition is injected into substantia nigra of the midbrain.

15. The method of claim 1, wherein the antisense nucleic acid sequence exhibits complementarity to a region of the gene.

* * * * *